(12) United States Patent
Thelemann et al.

(10) Patent No.: US 11,666,595 B2
(45) Date of Patent: Jun. 6, 2023

(54) ANTISENSE OLIGONUCLEOTIDES FOR INHIBITION OF PD-L1 EXPRESSION AND TREATING CANCER

(71) Applicant: Secarna Pharmaceuticals GmbH & Co. KG, Marburg (DE)

(72) Inventors: Tamara Thelemann, Munich (DE); Frank Jaschinski, Puchheim (DE); Richard Klar, Munich (DE)

(73) Assignee: Secarna Pharmaceuticals GmbH & Co. KG, Marburg (DE)

(*) Notice: Subject to any disclaimer, the term of this patent is extended or adjusted under 35 U.S.C. 154(b) by 0 days.

(21) Appl. No.: 16/340,318

(22) PCT Filed: Oct. 6, 2017

(86) PCT No.: PCT/EP2017/075511
§ 371 (c)(1),
(2) Date: Apr. 8, 2019

(87) PCT Pub. No.: WO2018/065589
PCT Pub. Date: Apr. 12, 2018

(65) Prior Publication Data
US 2020/0009181 A1    Jan. 9, 2020

(30) Foreign Application Priority Data
Oct. 7, 2016 (EP) .................... 16002166

(51) Int. Cl.
*A61K 31/7125* (2006.01)
*C12N 15/113* (2010.01)

(52) U.S. Cl.
CPC ........ *A61K 31/7125* (2013.01); *C12N 15/113* (2013.01); *C12N 2310/11* (2013.01); *C12N 2310/315* (2013.01); *C12N 2310/3231* (2013.01); *C12N 2310/341* (2013.01)

(58) Field of Classification Search
CPC .............. A61K 31/7125; C12N 15/113; C12N 2310/11; C12N 2310/315; C12N 2310/3231; C12N 2310/341; C12N 2310/346; C12N 15/1138
See application file for complete search history.

(56) References Cited

U.S. PATENT DOCUMENTS

| | | | |
|---|---|---|---|
| 4,309,404 A | 1/1982 | DeNeale et al. | |
| 4,309,406 A | 1/1982 | Guley et al. | |
| 4,556,552 A | 12/1985 | Porter et al. | |
| 4,704,295 A | 11/1987 | Porter et al. | |
| 7,622,453 B2 | 11/2009 | Frieden et al. | |
| 8,563,528 B2 | 10/2013 | Straarup et al. | |
| 2007/0172476 A1 | 7/2007 | Ueda et al. | |
| 2018/0371465 A1* | 12/2018 | Hinkle | G01N 33/574 |

FOREIGN PATENT DOCUMENTS

| | | |
|---|---|---|
| JP | 2004515214 A | 5/2004 |
| JP | 2010514791 A | 5/2010 |
| JP | 2013523162 A | 6/2013 |
| WO | 2001077384 A2 | 10/2001 |
| WO | 2005116204 A1 | 12/2005 |
| WO | 2006042237 A2 | 4/2006 |
| WO | 2007109797 A2 | 9/2007 |
| WO | 2011127180 A1 | 10/2011 |
| WO | 2014154843 A1 | 10/2014 |
| WO | 2015181343 A2 | 12/2015 |
| WO | 2016057933 A1 | 4/2016 |
| WO | 2016138278 A2 | 9/2016 |
| WO | 2017100587 A1 | 6/2017 |
| WO | 2017157899 A1 | 9/2017 |
| WO | 2018065589 A1 | 4/2018 |

OTHER PUBLICATIONS

Grünweller et al (Nucl. Acids Res. 31(12): 3185-3193, 2003) (Year: 2003).*
Burel et al (Nucl. Acids Res. 44(5): 2093-2109, 2016 (published Nov. 8, 2015)) (Year: 2015).*
Kurreck (Nucl. Acids Res. 30(9): 1911-1918, 2002) (Year: 2002).*
Zhang, Y., et al., "Down-Modulation of Cancer Targets Using Locked Nucleic Acid (LNA)-Based Antisense Oligonucleotides Without Transfection," Gene Therapy, 18, 306-333, 2011.
Stein, C.A., et al., "Efficient Gene Silencing by Delivery of Locked Nucleic Acid Antisense Oligonucleotides, Unassisted by Trnsfection Reagents", Nucleic Acid Research, vol. 38, No. 1, e3, 2010, doi:10.1093/nar/gkp841.
Mazanet, M.M. et al., "B7-H1 Is Expressed by Human Endothelial Cells and Suppresses T Cell Cytokine Synthesis", The Journal of Immunology, Oct. 1, 2002, vol. 169, Issue 7, pp. 3581-3588. doi: 10.4049/jimmunol.169.7.3581.
Sun et al., "CD39/ENTPD1 Expression by CD4+Foxp3+ Regulatory T Cells Promotes Hepatic Metastatic Tumor Growth in Mice", Gastoenterology 2010; 139:1030-1040.
Michaud et al., "Subversion of the chemotherapy-induced anticancer immune response by the ecto-ATPase CD39", OncoImmunology 1:3, 392-394; 2012.
Hagedorn et al., "Locked nucleic acid: modality, diversity, and drug discovery", Drug Discovery Today, vol. 23, No. 1, Jan. 2018, pp. 101-114.
Papargyri et al., "Chemical Diversity of Locked Nucleic Acid-Modified Antisense Oligonucleotides Allows Optimization of Pharmaceutical Properties", Molecular Therapy: Nucleic Acids, vol. 19, Mar. 2020, pp. 706-720.

* cited by examiner

*Primary Examiner* — Richard A Schnizer
(74) *Attorney, Agent, or Firm* — Verrill Dana, LLP

(57) ABSTRACT

The present invention relates to a novel approach for treating cancer, which is based on targeting PD-L1 mRNA. The invention is directed to oligonucleotides comprising 10 to 20 modified or unmodified nucleotides complementary to specifically selected regions of the PD-L1.

5 Claims, 13 Drawing Sheets

Specification includes a Sequence Listing.

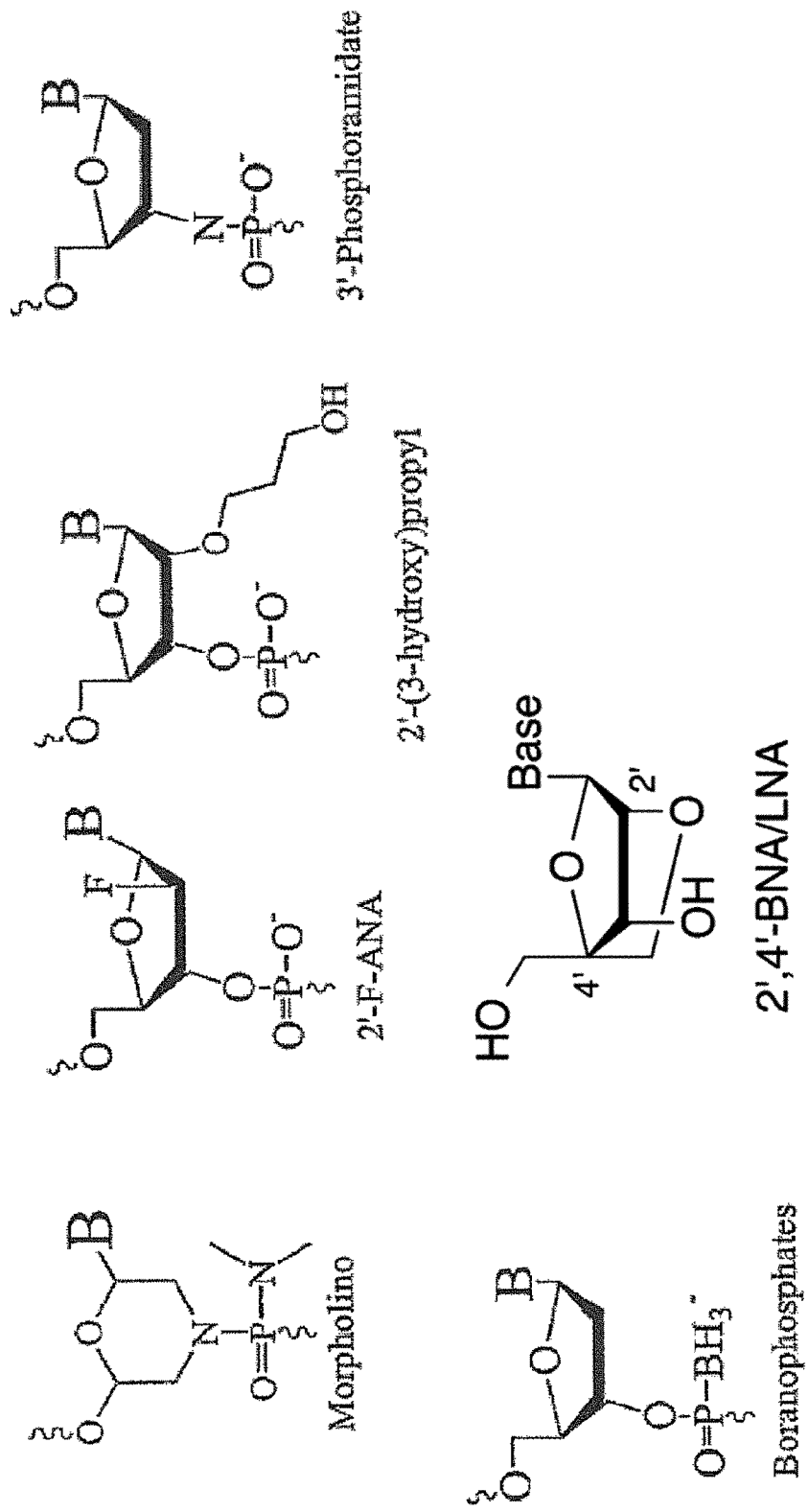
Figure 5 (contd.):

Figure 5 (contd.):
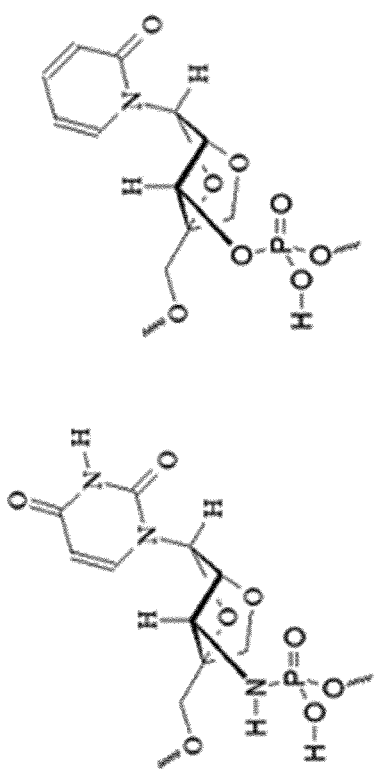
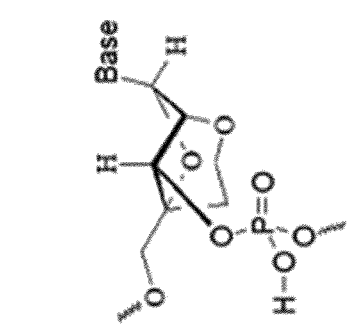
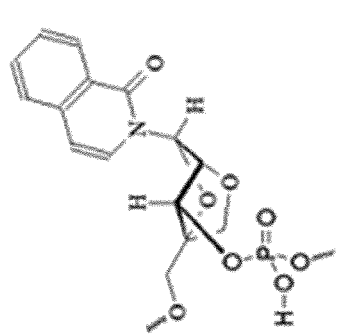
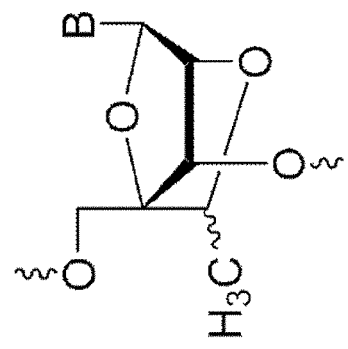

A)

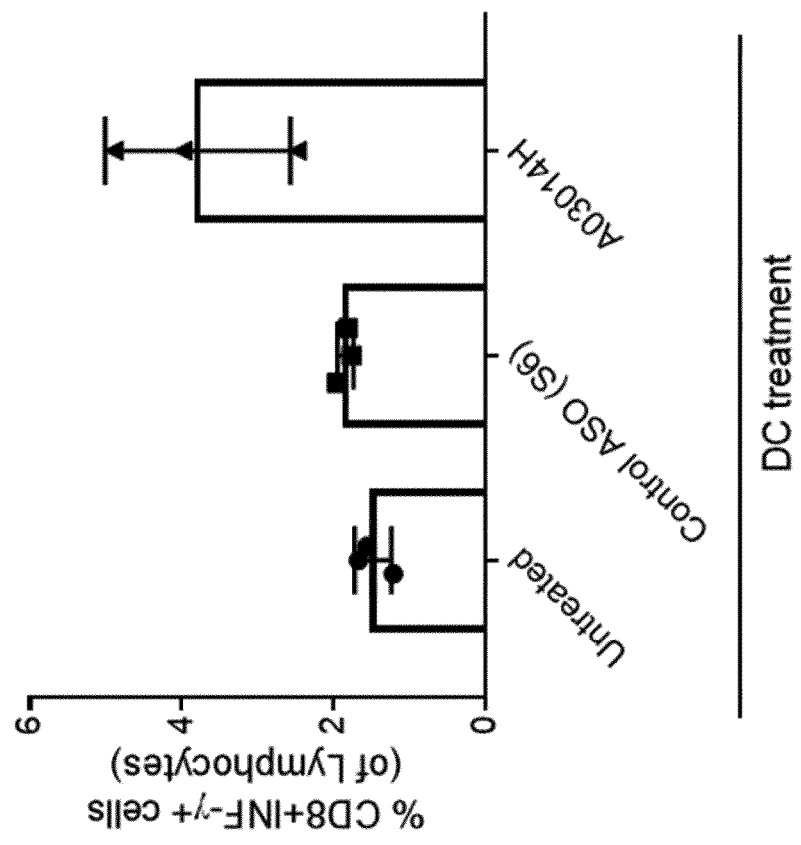
Figure 8 (contd.):

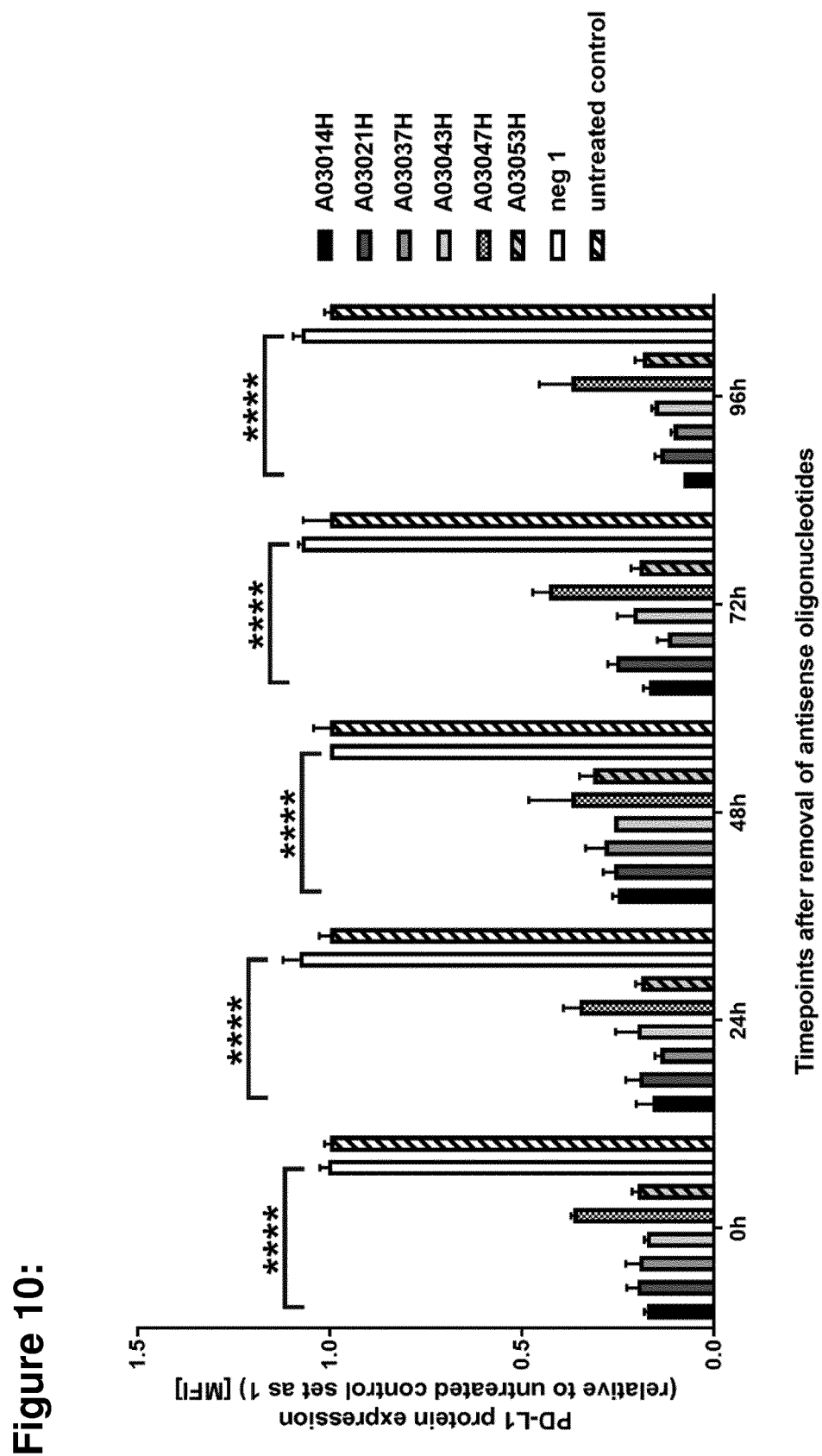

ANTISENSE OLIGONUCLEOTIDES FOR INHIBITION OF PD-L1 EXPRESSION AND TREATING CANCER

FIELD OF THE INVENTION

The present invention relates to a novel approach for treating a tumor, which is based on targeting PD-L1 mRNA. The invention is directed to oligonucleotides comprising 10 to 20 modified or unmodified nucleotides complementary to specifically selected regions of PD-L1 mRNA.

BACKGROUND OF THE INVENTION

During the last decades of cancer research it became obvious that the immune system is indispensable to initiate and release an effective anti-tumor response. Therefore it needs to be integrated in common cancer therapies. However, cancer cells developed mechanisms to circumvent anti-tumor immune responses, e.g. by downregulating HLA molecules leading to impaired antigen presentation, by the secretion of inhibitory soluble mediators such as IL-10 or adenosine, or by expressing T cell inhibitory ligands.

The most prominent inhibitory ligands expressed on the surface of antigen presenting cells and cancer cells are Programmed death-ligand 1 and 2 (PD-L1/PD-L2). Programmed death-ligand 1 (PD-L1) also known as cluster of differentiation 274 (CD274) or B7 homolog 1 (B7-H1) is a protein that is encoded in humans by the CD274 gene. While PD-L2 (B7-DC or CD273) is expressed primarily on professional antigen presenting cells (such as B cells and dendritic cells), PD-L1 is expressed on non-lymphoid cells, such as parenchymal cells, virus-infected cells and tumor cells, as well as on other immune cells.

The two ligands interact with their receptor Programmed death-1 (PD-1), expressed on several immune cells, such as activated T cells, B cells, natural killer cells and myeloid cells in the periphery. The initial role of the interaction between the negative receptor PD-1 and its ligands is thought to regulate the threshold of antigen responses of T cells and B cells in the periphery. Activation of PD-1 by its ligands during infection or inflammation in normal tissue is critically important in maintaining homeostasis of immune response to prevent autoimmunity. Their interaction in tumor microenvironments, however, provides an immune escape for tumor cells by dephosphorylating key proteins downstream of the T cell receptor after antigen encounter, mainly in the late phase of an immune response mediating exhaustion or anergy of effector T cells. Engagement of PD-1 by its ligands during antigen recognition induces cross linkage of the antigen-receptor complex with PD-1. This mediates phosphorylation of the tyrosine residue in the immunoreceptor tyrosine-based switch motif (ITSM) leading to the recruitment of tyrosine phosphatases that dephosphorylate and inactivate proximal effector molecules such as Zap70 in T cells. These molecular mechanisms lead to decreased TCR signaling which in turn drives reduced proliferation and cytokine production of effector T cells.

Deficiency of PD-1 in mice renders them resistant to viral infection and induces the suppression of tumor growth and metastasis in different tumor models. Thus, blocking PD-1/PD-L1 interactions can result in therapeutic benefit in tumor-bearing mice, as it leads to improved tumor cell killing by cytotoxic T cells. In addition, deficient PD-1 expression in mice results in loss of peripheral tolerance and the subsequent development of autoimmune diseases such as lupus-like glomerulonephritis, arthritis, hepatitis or cardiomyopathy.

In humans, genetic alterations of the PD-1 encoding gene (PDCD1) is associated with increased susceptibility towards several autoimmune diseases, such as systemic lupus erythematosus, type 1 diabetes, multiple sclerosis, rheumatoid arthritis, Grave's disease and ankylosing spondylitis. However, distinct from other negative immune regulators, PD-1 deficiency specifically and only affects antigen-specific autoimmune responses whereas deficiency of other negative regulators results in systemic, non-antigen-specific autoimmune phenotypes.

Until present, the blockade of PD-1/PD-L1 interactions by monoclonal antibodies or by genetic manipulation of PD-1 expression led to enhanced tumor eradication. Furthermore, clinical data suggest that enhanced PD-L1 expression in tumors correlates with poorer survival prognosis of different cancer patients. These results led to the development of several different fully humanized monoclonal antibodies targeting either PD-1 or PD-L1. Application of those antibodies showed positive response rates in humans in clinical trials of e.g. non-small-cell lung cancer, melanoma, renal cell carcinoma, and Hodgkin lymphoma with drug-related adverse events in a subset of patients. Nonetheless, therapeutic blockade of the PD-1 pathway is the most powerful target for immunological anti-tumor therapies in the clinics at present.

However, a large proportion of cancer patients (>70%) do not respond well to therapeutic blockade of PD-1 using monoclonal antibody therapies. These data suggest the importance of accessing combinatorial therapies using agents to block additional negative or to activate positive regulators that might have additive and/or synergistic effects in order to improve antitumor immunotherapies. The application of antisense oligonucleotides targeting PD-L1 expression on mRNA level in combination with therapies that target other known negative (e.g. LAG-3; TIM-3; 2B4; CD160) or positive (e.g. CD137; CD40) immune-regulatory pathways could provide better therapeutic efficacy than targeting the PD-1 pathway alone.

Several studies indicate the presence of an immune inhibitory soluble form of PD-L1 (sPD-L1) in sera of cancer patients, correlating with disease severity and a negative patient survival outcome. Thus, it is very likely that the soluble form of PD-L1 cannot be fully captured by conventional monoclonal antibodies directed against PD-L1 on a systemic level.

Furthermore, antibodies are huge in molecular size and therefore might not reach targets expressed on dense and packed tissues as it is the case for many different tumors.

Thus, while targeting PD-L1 appears to be a promising approach to develop and improve novel immunotherapies against different cancers, no satisfactory solution for achieving that has yet been found. Hence, there is still a high scientific and medical need for therapeutic agents, which reduce or inhibit PD-L1 expression and/or activity.

Based on experiences with similar signaling interactions, it appeared to be likely that tumor cells are more accessible to be targeted by inhibition of gene expression, e.g. by antisense oligonucleotides. Thus, the inhibition of target expression could be a more promising approach to develop and improve novel immunotherapies against different cancers than conventional antibody therapies. Currently two competing technologies are predominantly used for specific suppression of mRNA expression: Antisense oligonucleotides and si RNA.

Due to its double stranded nature, siRNA does not cross the cell membrane by itself and delivery systems are required for its activity in vitro and in vivo. While delivery systems for siRNA exist that efficiently deliver siRNA to liver cells in vivo, there is currently no system that can deliver siRNA in vivo to extra-hepatic tissues such as tumors with sufficient efficacy. Therefore siRNA approaches to target PD-L1 are currently limited to ex vivo approaches, for example for the generation of dendritic cell-based tumor vaccines.

For antisense oligonucleotides efficacy in cell culture is typically determined after transfection using transfection reagents or electroporation. Antisense approaches directed against PD-L1 are described, for example, in WO 2006/042237 or WO 2016/057933, or in Mazanet et al., J. Immunol. 169 (2002) 3581-3588.

It was recently discovered that antisense oligonucleotides that are modified by so called $3^{rd}$ generation chemistries, such as 2',4'-LNA (see, for example, WO 2014/154843 A1) or constrained ethyl bridged nucleic acids (c-ET), can enter cells in vitro and in vivo without a delivery system to achieve target downregulation.

Additionally, double-stranded RNA molecules (see WO 2011/127180) and so-called "3rd generation antisense compounds", which comprise two antisense constructs linked via their 5' ends (see WO 2016/138278), have been tested as PD-L1 inhibitors.

However, in approaches described in the prior art only moderate target suppression levels were achieved and relatively high concentrations of oligonucleotides were required for efficient target suppression. For example, in U.S. Pat. No. 8,563,528 a concentration of 10 µM resulted in a target inhibition of just 70%. $IC_{50}$ values for $3^{rd}$ generation oligonucleotides without transfection reagent typically range between 300 and 600 nM (Zhang et al. Gene Therapy (2011) 18, 326-333).

After systemic administration in vivo, only relatively low oligonucleotide concentrations can be achieved in relevant target tissues. Therefore antisense oligonucleotides that reach high maximal target suppression at low concentration would clearly result in an enhanced therapeutic effect.

Furthermore, in the case of gene silencing using LNA-modified antisense molecules, it has been observed that after removal of the antisense constructs, the target protein expression level rapidly raised again, and reached 50% of baseline expression in 24 h, and 100% in 72 h (see Stein et al., Nucleic Acids Res. 38 (2010) e3 [doi:10.1093/nar/gkp841]).

Thus, while targeting PD-L1 appears to be a promising approach to develop and improve novel immunotherapies against different cancers, no satisfactory solution for achieving that has yet been found. Hence, there is still a high scientific and medical need for therapeutic agents, which efficiently reduce or inhibit PD-L1 expression and/or activity, in particular for a prolonged period of time.

SUMMARY OF THE INVENTION

Despite the suboptimal results obtained with the approaches described in the prior art that suppress disease causing targets with antisense approaches, the present inventors surprisingly identified that certain specific antisense constructs were able to achieve the inhibition of the expression of PD-L1 relative to untreated control in HDLM-2 cells by at least 80%, with several candidates achieving inhibition of more than 85%, of more than 90%, or of more than 95%, and/or relative to untreated control in U-87MG cells by at least 50%, with several candidates achieving inhibition of more than 75%, more particularly of more than 80%. $IC_{50}$ values in HDLM-2 cells were below 100 nM for several candidates or even below 20 nM for selected candidates. Most importantly, the inhibition of PD-L1 expression continued after removal of the anti-PD-L1 constructs, in particular for at least 96 h.

Thus, in a first aspect, the present invention relates to an oligonucleotide consisting of from 10 to 20 nucleotides, particularly from 13 to 18 nucleotides, wherein the sequence of said oligonucleotide corresponds to the antisense strand of the PD-L1 nucleic acid coding sequence of SEQ ID NO. 115, wherein one or more nucleotide(s) of the oligonucleotide is/are optionally modified, and wherein said oligonucleotide inhibits the expression of PD-L1 relative to untreated control in HDLM-2 cells by at least 80%.

In a second aspect, the present invention relates to a pharmaceutical composition comprising the oligonucleotide according to the present invention.

In a third aspect, the present invention relates to the oligonucleotides or the pharmaceutical composition according to the present invention for use in a method of preventing and/or treating a disease or disorder selected from the list of: a malignant tumor and a benign tumor.

BRIEF DESCRIPTION OF THE DRAWINGS

FIG. 10 shows the analysis of PD-L1 protein expression by flow cytometry in HDLM-2 cells 1, 2, 3 and 4 days after removal of selected oligonucleotides. PD-L1 protein expression is depicted as mean fluorescence intensity (MFI) and was calculated by subtracting the MFI of PD-L1 by the MFI of unspecific isotype control. Relative expression compared to untreated control cells (set as 1) is depicted. PD-L1 expression was analyzed in duplicates for each condition (specific staining and isotype control). Data were analyzed using Two-tailed student's t-test, P≤0.0001 (****).

DETAILED DESCRIPTION OF THE INVENTION

Thus, in a first aspect, the present invention relates to an oligonucleotide consisting of from 10 to 20 nucleotides, particularly from 13 to 18 nucleotides, wherein the sequence of said oligonucleotide corresponds to the antisense strand of the PD-L1 nucleic acid coding sequence of SEQ ID NO. 115 (Table 15), wherein one or more nucleotide(s) of the oligonucleotide is/are optionally modified, and wherein said oligonucleotide inhibits the expression of PD-L1 relative to untreated control in HDLM-2 cells by at least 80%.

In particular embodiments of the present invention, said oligonucleotide inhibits the expression of PD-L1 relative to untreated control in HDLM-2 cells by at least 85%, more particularly by at least 90%, and most particularly by at least 95%.

In particular such embodiments, said oligonucleotide inhibits the expression of PD-L1 relative to untreated control in HDLM-2 cells for at least 24 h after removal of said oligonucleotide, in particular for at least 48 h, for at least 72 h, or in particular for at least 96 h.

In particular embodiments of the present invention, one or more nucleotide(s) in said oligonucleotide are modified.

Figure 5:
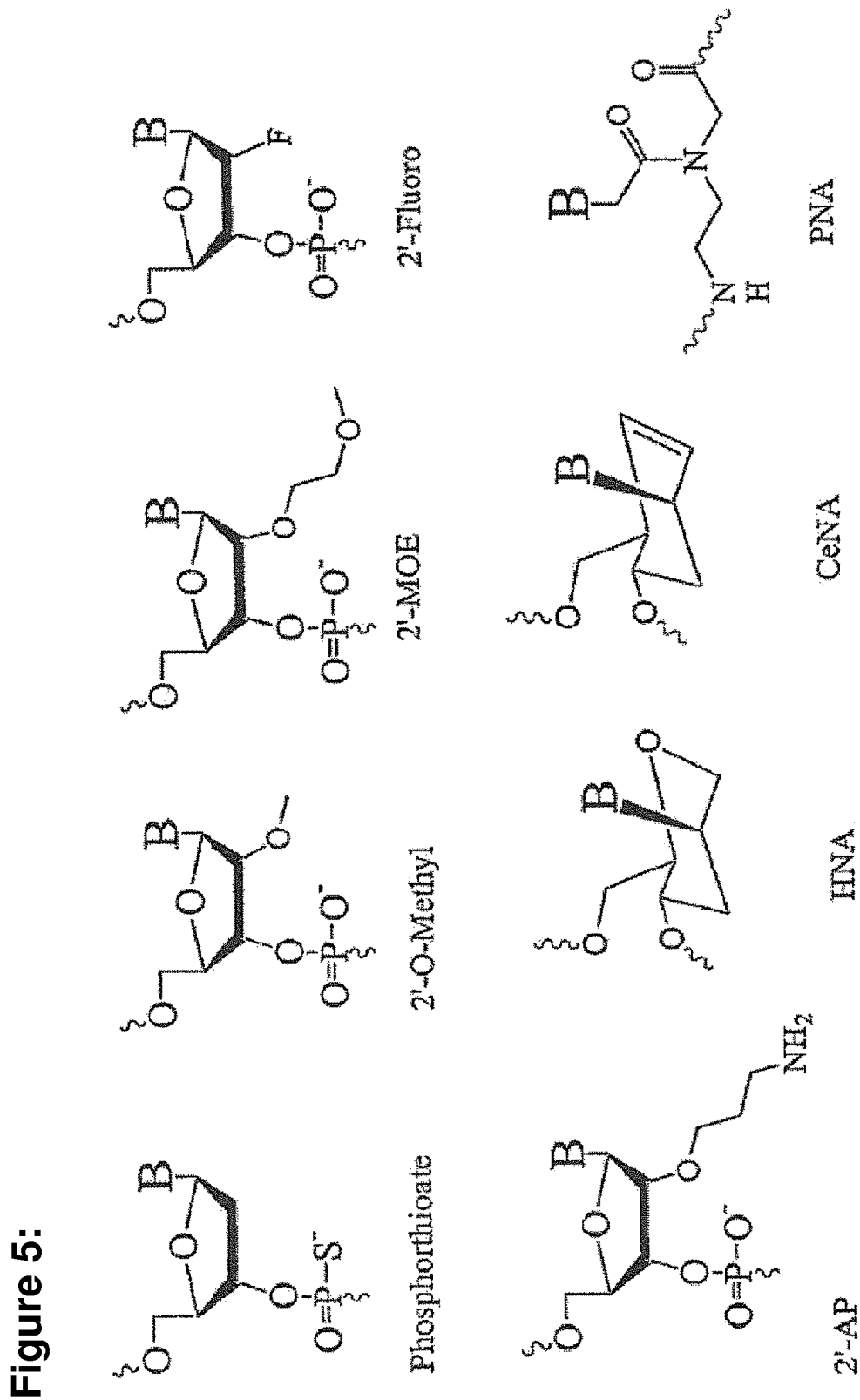
FIG. 5 shows a number of different modified nucleotides that may be used in the context of the present invention.

A nucleotide forms the building block of an oligonucleotide, and is for example composed of a nucleobase (nitrogenous base, e.g., purine or pyrimidine), a five-carbon sugar (e.g., ribose, 2-deoxyribose, arabinose, xylose, lyxose, allose, altrose, glucose, mannose, gulose, idose, galactose, talose or stabilized modifications of those sugars), and one or more phosphate groups. Examples of modified phosphate groups are phosphorothioate or methylphosphonate. Each compound of the nucleotide is modifiable, and is naturally or non-naturally occurring. Examples of the latter are: locked nucleic acid (LNA), 2', 4' constrained ethyl nucleic acids (c-ET), 2'-0,4'-C-ethylene-bridged nucleic acid (ENA), polyalkylene oxide—(such as triethylene glycol (TEG)), 2'-fluoro-, 2'-deoxy-2'-fluoro-beta-D-arabinonucleic acid (FANA), 2'-0-methoxy- and 2'-0-methyl-modified nucleotides. FIG. 5 shows examples of a number of different modified nucleotides that may be used in the context of the present invention.

An "LNA" is a modified RNA nucleotide, wherein the ribose moiety is modified with an extra bridge connecting the 2' oxygen and 4' carbon (2'-4 'ribonucleoside). The bridge locks the ribose in the 3'-endo (North) conformation, which is often found in the A-form duplexes. LNA nucleosides and nucleotides, respectively, comprise for example the forms of thio-LNA, oxy-LNA, or amino-LNA, in alpha-D- or beta-L-configuration, and can be mixed or combined, respectively, with DNA or RNA residues in the oligonucleotide.

A "bridged nucleic acid" is modified RNA nucleotide, sometimes also referred to as constrained or inaccessible RNA molecule, which may contain a five-membered, six-membered or even a seven-membered bridged structure with a "fixed" C3'-endo sugar puckering. The bridge is synthetically incorporated at the 2', 4'-position of the ribose to afford a 2', 4'-BNA monomer. Specific examples are "ENA" nucleotides, wherein the bridge is an ethylene bridge. FIG. 5 shows a number of BNA nucleotides that may be used in the context of the present invention.

In a particular embodiment, one or more nucleotide(s) in said oligonucleotide are modified, wherein the modified nucleotide contains a modified phosphate group, particularly selected from a phosphorothioate and a methylphosphonate, particularly a phosphorothioate. In particular embodiments, all phosphate groups of the oligonucleotide are modified phosphate groups, particularly independently selected from phosphorothioates and methylphosphonates, particularly wherein all phosphate groups are phosphorothioates.

In a particular embodiment, one or more nucleotide(s) in said oligonucleotide are modified, wherein the modified nucleotide is an LNA, a c-ET, an ENA, a polyalkylene oxide-, a 2'-fluoro-, a 2'-O-methoxy-, a FANA and/or a 2'-O-methyl-modified nucleotide.

In particular embodiments, the modified nucleotide(s) is/are located within the stretch of 5 nucleotides at the 5'- and/or 3'-end of the oligonucleotide, particularly at the 5'- and the 3'-end of the oligonucleotide.

In particular embodiments, the oligonucleotides of the present invention comprise at least one modified nucleotide, particularly at least one LNA, c-ET and/or ENA, at the 5'- and/or 3'-end of the oligonucleotide. In a particular embodiment, the oligonucleotide comprises 1, 2, 3, or 4 LNAs or c-ETs or ENAs within the stretch of up to 5 nucleotides at the 5'-end, and 1, 2, 3, or 4 LNAs or c-ETs or ENAs within the stretch of up to 5 nucleotides at the 3 '-end. In another particular embodiment, the oligonucleotide comprises 1, 2, 3, or 4 LNAs, c-ETs, or ENAs at the within the stretch of 5 nucleotides 5'-end or 3'-end, and a polyalkylene oxide such as TEG within the stretch of 5 nucleotides at the 3'- or 5'-end.

In particular embodiments, said oligonucleotide is a Gapmer comprising at least one LNA nucleotide within the stretch of 5 nucleotides at the 5'-end of said oligonucleotide, and at least one LNA nucleotide within the stretch of 5 nucleotides at the 3'-end of said oligonucleotide. In particular embodiments, said Gapmer comprises 2 or 3 LNA nucleotides within the stretch of 5 nucleotides at the 5'-end of said oligonucleotide, and 2 or 3 LNA nucleotides within the stretch of 5 nucleotides at the 3'-end of said oligonucleotide.

In the context of the present invention, the term "Gapmer" refers to a chimeric antisense oligonucleotide that contains a central block of deoxynucleotide monomers sufficiently long to induce RNase H cleavage. The central block of a Gapmer is flanked by blocks of 2'-0 modified ribonucleotides or other artificially modified ribonucleotide monomers such as bridged nucleic acids (BNAs) that protect the internal block from nuclease degradation. In many earlier studies modified DNA analogs were investigated for their stability in biological fluids. In the majority of these experiments phosphorothioate DNA analogs were used. More recently, several types of artificial nucleotide monomers including BNA monomers have been investigated for their usefulness in the design of Gapmers. Gapmers have been used to obtain RNase-H mediated cleavage of target RNAs, while reducing the number of phosphorothioate linkages. Phosphorothioates possess increased resistance to nucleases compared to unmodified DNA. However, they have several disadvantages. These include low binding capacity to complementary nucleic acids and non-specific binding to proteins that cause toxic side-effects limiting their applications. The occurrence of toxic side-effects together with non-specific binding causing off-target effects has stimulated the design of new artificial nucleic acids for the development of modified oligonucleotides that provide efficient and specific antisense activity in vivo without exhibiting toxic side-effects.

LNA Gapmers are powerful tools for loss of function studies of proteins, mRNA and lncRNAs. These single strand antisense oligonucleotides catalyze RNase H-dependent degradation of complementary RNA targets. LNA Gapmers are typically 12-20 nucleotides long enriched with LNA in the flanking regions and DNA in a LNA free central gap—hence the name Gapmer. The LNA-containing flanking regions confers nuclease resistance to the antisense oligo while at the same time increases target binding affinity regardless of the GC content. The central DNA "gap" activates RNase H cleavage of the target RNA upon binding.

In particular embodiments of the present in invention, the oligonucleotide comprises a sequence selected from the group consisting of SEQ ID NO. 42, SEQ ID NO. 106, SEQ ID NO. 86, SEQ ID NO. 28, SEQ ID NO. 110, SEQ ID NO. 74, SEQ ID NO. 94, SEQ ID NO. 108, SEQ ID NO. 88, SEQ ID NO. 56, SEQ ID NO. 46, SEQ ID NO. 96, SEQ ID NO. 48, SEQ ID NO. 50, SEQ ID NO. 62, SEQ ID NO. 114, SEQ ID NO. 34, SEQ ID NO. 98, SEQ ID NO. 84, SEQ ID NO. 82, SEQ ID NO. 4, SEQ ID NO. 12, SEQ ID NO. 92, SEQ ID NO. 102, SEQ ID NO. 100, SEQ ID NO. 58, SEQ ID NO. 16, SEQ ID NO. 76, SEQ ID NO. 72, SEQ ID NO. 54, SEQ ID NO. 66, SEQ ID NO. 68, SEQ ID NO. 112, and SEQ ID NO. 104, particularly from the group consisting of SEQ ID NO. 42, SEQ ID NO. 106, SEQ ID NO. 86, SEQ ID NO. 28, SEQ ID NO. 110, SEQ ID NO. 74, SEQ ID NO. 94, SEQ ID NO. 108, SEQ ID NO. 88, SEQ ID NO. 56, SEQ ID NO. 46, SEQ ID NO. 96, SEQ ID NO. 48, SEQ ID NO. 50, SEQ ID NO. 62, SEQ ID NO. 114, SEQ ID NO. 34, SEQ ID NO. 98, SEQ ID NO. 84, SEQ ID NO. 82, SEQ ID NO. 4, SEQ ID NO. 12, SEQ ID NO. 92, SEQ ID NO. 102, SEQ ID NO. 100, SEQ ID NO. 58, and SEQ ID NO. 16, more particularly from the group consisting of SEQ ID NO. 42, SEQ ID NO. 106, SEQ ID NO. 86, SEQ ID NO. 28, SEQ ID NO. 110, SEQ ID NO. 74, SEQ ID NO. 94, SEQ ID NO. 108, SEQ ID NO. 88, SEQ ID NO. 56, SEQ ID NO. 46, SEQ ID NO. 96, SEQ ID NO. 48, SEQ ID NO. 50, SEQ ID NO. 62, SEQ ID NO. 114, SEQ ID NO. 34, SEQ ID NO. 98, and SEQ ID NO. 84, more particularly from the group consisting of SEQ ID NO. 42, SEQ ID NO. 106, SEQ ID NO. 86, SEQ ID NO. 28, SEQ ID NO. 110, and SEQ ID NO. 74, and more particularly from the group consisting of SEQ ID NO. 42, SEQ ID NO. 106, SEQ ID NO. 86, and SEQ ID NO. 28.

In a particular embodiment, the oligonucleotide is a variant of a sequence selected from the group consisting of SEQ ID NO. 42, SEQ ID NO. 106, SEQ ID NO. 86, SEQ ID NO. 28, SEQ ID NO. 110, SEQ ID NO. 74, SEQ ID NO. 94, SEQ ID NO. 108, SEQ ID NO. 88, SEQ ID NO. 56, SEQ ID NO. 46, SEQ ID NO. 96, SEQ ID NO. 48, SEQ ID NO. 50, SEQ ID NO. 62, SEQ ID NO. 114, SEQ ID NO. 34, SEQ ID NO. 98, SEQ ID NO. 84, SEQ ID NO. 82, SEQ ID NO. 4, SEQ ID NO. 12, SEQ ID NO. 92, SEQ ID NO. 102, SEQ ID NO. 100, SEQ ID NO. 58, SEQ ID NO. 16, SEQ ID NO. 76, SEQ ID NO. 72, SEQ ID NO. 54, SEQ ID NO. 66, SEQ ID NO. 68, SEQ ID NO. 112, and SEQ ID NO. 104, particularly from the group consisting of SEQ ID NO. 42, SEQ ID NO. 106, SEQ ID NO. 86, SEQ ID NO. 28, SEQ ID NO. 110, SEQ ID NO. 74, SEQ ID NO. 94, SEQ ID NO. 108, SEQ ID NO. 88, SEQ ID NO. 56, SEQ ID NO. 46, SEQ ID NO. 96, SEQ ID NO. 48, SEQ ID NO. 50, SEQ ID NO. 62, SEQ ID NO. 114, SEQ ID NO. 34, SEQ ID NO. 98, SEQ ID NO. 84, SEQ ID NO. 82, SEQ ID NO. 4, SEQ ID NO. 12, SEQ ID NO. 92, SEQ ID NO. 102, SEQ ID NO. 100, SEQ ID NO. 58, and SEQ ID NO. 16, more particularly from the group consisting of SEQ ID NO. 42, SEQ ID NO. 106, SEQ ID NO. 86, SEQ ID NO. 28, SEQ ID NO. 110, SEQ ID NO. 74, SEQ ID NO. 94, SEQ ID NO. 108, SEQ ID NO. 88, SEQ ID NO. 56, SEQ ID NO. 46, SEQ ID NO. 96, SEQ ID NO. 48, SEQ ID NO. 50, SEQ ID NO. 62, SEQ ID NO. 114, SEQ ID NO. 34, SEQ ID NO. 98, and SEQ ID NO. 84, more particularly from the group consisting of SEQ ID NO. 42, SEQ ID NO. 106, SEQ ID NO. 86, SEQ ID NO. 28, SEQ ID NO. 110, and SEQ ID NO. 74, and more particularly from the group consisting of SEQ ID NO. 42, SEQ ID NO. 106, SEQ ID NO. 86, and SEQ ID NO. 28, wherein in such variant one or more of the phosphorothioates are independently replaced by an unmodified phosphate of a modified phosphate other than a phosphorothioate, particularly a methylphosphonate.

In a particular embodiment, the oligonucleotide is a variant of a sequence selected from the group consisting of SEQ ID NO. 42, SEQ ID NO. 106, SEQ ID NO. 86, SEQ ID NO. 28, SEQ ID NO. 110, SEQ ID NO. 74, SEQ ID NO. 94, SEQ ID NO. 108, SEQ ID NO. 88, SEQ ID NO. 56, SEQ ID NO. 46, SEQ ID NO. 96, SEQ ID NO. 48, SEQ ID NO. 50, SEQ ID NO. 62, SEQ ID NO. 114, SEQ ID NO. 34, SEQ ID NO. 98, SEQ ID NO. 84, SEQ ID NO. 82, SEQ ID NO. 4, SEQ ID NO. 12, SEQ ID NO. 92, SEQ ID NO. 102, SEQ ID NO. 100, SEQ ID NO. 58, SEQ ID NO. 16, SEQ ID NO. 76, SEQ ID NO. 72, SEQ ID NO. 54, SEQ ID NO. 66, SEQ ID NO. 68, SEQ ID NO. 112, and SEQ ID NO. 104, particularly from the group consisting of SEQ ID NO. 42, SEQ ID NO. 106, SEQ ID NO. 86, SEQ ID NO. 28, SEQ ID NO. 110, SEQ ID NO. 74, SEQ ID NO. 94, SEQ ID NO. 108, SEQ ID NO. 88, SEQ ID NO. 56, SEQ ID NO. 46, SEQ ID NO. 96, SEQ ID NO. 48, SEQ ID NO. 50, SEQ ID NO. 62, SEQ ID NO. 114, SEQ ID NO. 34, SEQ ID NO. 98, SEQ ID NO. 84, SEQ ID NO. 82, SEQ ID NO. 4, SEQ ID NO. 12, SEQ ID NO. 92, SEQ ID NO. 102, SEQ ID NO. 100, SEQ ID NO. 58, and SEQ ID NO. 16, more particularly from the group consisting of SEQ ID NO. 42, SEQ ID NO. 106, SEQ ID NO. 86, SEQ ID NO. 28, SEQ ID NO. 110, SEQ ID NO. 74, SEQ ID NO. 94, SEQ ID NO. 108, SEQ ID NO. 88, SEQ ID NO. 56, SEQ ID NO. 46, SEQ ID NO. 96, SEQ ID NO. 48, SEQ ID NO. 50, SEQ ID NO. 62, SEQ ID NO. 114, SEQ ID NO. 34, SEQ ID NO. 98, and SEQ ID NO. 84, more particularly from the group consisting of SEQ ID NO. 42, SEQ ID NO. 106, SEQ ID NO. 86, SEQ ID NO. 28, SEQ ID NO. 110, and SEQ ID NO. 74, and more particularly from the group consisting of SEQ ID NO. 42, SEQ ID NO. 106, SEQ ID NO. 86, and SEQ ID NO. 28, wherein such variant comprises one or more nucleotide mismatches particularly one or two mismatches, more particularly one mismatch, provided that any such variant including the mismatch(es), when analyzed with the bioinformatic tools described in Example 1, contains at least one mismatch relative to human whole genome screening while maintaining homology to relevant species.

In a second aspect, the present invention relates to a pharmaceutical composition comprising an oligonucleotide according to the present invention.

In particular embodiments, the pharmaceutical composition further comprises a pharmaceutically acceptable carrier.

In particular embodiments, the pharmaceutical composition further comprises at least one additional component selected from: a further anti-sense compound, an antibody, a chemotherapeutic compound, an anti-inflammatory compound, an antiviral compound, an immuno-modulating compound, a pharmaceutically acceptable binding agents and an adjuvant.

In one embodiment, the oligonucleotide and the pharmaceutical composition, respectively, is formulated as dosage unit in form of capsules, tablets and pills etc., respectively, which contain for example the following compounds: microcrystalline cellulose, gum or gelatin as binders; starch or lactose as excipients; stearates as lubricants, various sweetening or flavouring agents. For capsules the dosage unit may contain a liquid carrier like fatty oils. Likewise coatings of sugar or enteric agents may be part of the dosage unit.

The oligonucleotide and/or the pharmaceutical composition is administrable via different routes. These routes of administration include, but are not limited to, electroporation, epidermal, impression into skin, intra-arterial, intra-articular, intracranial, intradermal, intra-lesional, intra-muscular, intranasal, intra-ocular, intrathecal, intracameral, intraperitoneal, intraprostatic, intrapulmonary, intraspinal, intratracheal, intratumoral, intravenous, intravesical, rectal, placement within cavities of the body, nasal inhalation, oral, pulmonary inhalation (e.g., by inhalation or insufflation of powders or aerosols, including by nebulizer), subcutaneous, subdermal, topical (including ophthalmic and to mucous membranes including vaginal and rectal delivery), or transdermal administration.

For parenteral, subcutaneous, intradermal or topical administration the oligonucleotide and/or the pharmaceutical composition include for example a sterile diluent, buffers, regulators of toxicity and antibacterials. In a preferred embodiment, the oligonucleotide or pharmaceutical composition is prepared with carriers that protect against degradation or immediate elimination from the body, including implants or microcapsules with controlled release properties. For intravenous administration the preferred carriers are for example physiological saline or phosphate buffered saline. An oligonucleotide and/or a pharmaceutical composition comprising such oligonucleotide for oral administration includes for example powder or granule, microparticulate, nanoparticulate, suspension or solution in water or non-aqueous media, capsule, gel capsule, sachet, tablet or minitablet. An oligonucleotide and/or a pharmaceutical composition comprising for parenteral, intrathecal, intracameral or intraventricular administration includes for example sterile aqueous solutions which optionally contain buffer, diluent and/or other suitable additive such as penetration enhancer, carrier compound and/or other pharmaceutically acceptable carrier or excipient.

A pharmaceutically acceptable carrier is for example liquid or solid, and is selected with the planned manner of administration in mind so as to provide for the desired bulk, consistency, etc., when combined with a nucleic acid and the other components of a given pharmaceutical composition. Typical pharmaceutically acceptable carriers include, but are not limited to, a binding agent (e.g. pregelatinized maize starch, polyvinylpyrrolidone or hydroxypropyl methylcellulose, etc.); filler (e.g. lactose and other sugars, microcrystalline cellulose, pectin, gelatin, calcium sulfate, ethyl cellulose, polyacrylates or calcium hydrogen phosphate, etc.); lubricant (e.g., magnesium stearate, talcum, silica, colloidal silicon dioxide, stearic acid, metallic stearates, hydrogenated vegetable oils, corn starch, polyethylene glycols, sodium benzoate, sodium acetate, etc.); disintegrate (e.g., starch, sodium starch glycolate, etc.); or wetting agent (e.g., sodium lauryl sulfate, etc.). Sustained release oral delivery systems and/or enteric coatings for orally administered dosage forms are described in U.S. Pat. Nos. 4,704,295; 4,556,552; 4,309,406; and 4,309,404. An adjuvant is included under these phrases.

Besides being used in a method of human disease prevention and/or treatment, the oligonucleotide and/or the pharmaceutical composition according to the present invention is also used in a method for prevention and/or treatment of other subjects including veterinary animals, reptiles, birds, exotic animals and farm animals, including mammals, rodents, and the like. Mammals include for example horses, dogs, pigs, cats, or primates (for example, a monkey, a chimpanzee, or a lemur). Rodents include for example rats, rabbits, mice, squirrels, or guinea pigs.

In a third aspect, the present invention relates to a pharmaceutical composition comprising the oligonucleotide according to the present invention for use in a method of preventing and/or treating a disease or disorder selected from the list of: a malignant tumor and a benign tumor.

In particular other embodiments of the present invention, the tumor is selected from the group consisting of solid tumors, blood born tumors, leukemias, tumor metastasis, hemangiomas, acoustic neuromas, neurofibromas, trachomas, pyogenic granulomas, psoriasis, astrocytoma, acoustic neuroma, blastoma, Ewing's tumor, craniopharyngioma, ependymoma, medulloblastoma, glioma, hemangioblastoma, Hodgkin's lymphoma, medullablastoma, leukaemia, mesothelioma, neuroblastoma, neurofibroma, non-Hodgkin's lymphoma, pinealoma, retinoblastoma, sarcoma, seminoma, trachomas, and Wilms' tumor, or is selected from the group of bile duct carcinoma, bladder carcinoma, brain tumor, breast cancer, bronchogenic carcinoma, carcinoma of the kidney, cervical cancer, choriocarcinoma, choroid carcinoma, cystadenocarcinoma, embryonal carcinoma, epithelial carcinoma, esophageal cancer, cervical carcinoma, colon carcinoma, colorectal carcinoma, endometrial cancer, gallbladder cancer, gastric cancer, head cancer, liver carcinoma, lung carcinoma, medullary carcinoma, neck cancer, non-small-cell bronchogenic/lung carcinoma, ovarian cancer, pancreas carcinoma, papillary carcinoma, papillary adenocarcinoma, prostate cancer, small intestine carcinoma, prostate carcinoma, rectal cancer, renal cell carcinoma, retinoblastoma, skin cancer, small-cell bronchogenic/lung carcinoma, squamous cell carcinoma, sebaceous gland carcinoma, testicular carcinoma, and uterine cancer.

For the purpose of clarity and a concise description, features are described herein as part of the same or separate embodiments, however, it will be appreciated that the scope of the invention may include embodiments having combinations of all or some of the features described.

The following examples will serve to further illustrate the present invention without, at the same time, however, constituting any limitation thereof. On the contrary, it is to be clearly understood that the scope of the present invention refers to various other embodiments, modifications, and equivalents thereof which, after reading the description herein, may suggest themselves to those skilled in the art without departing from the spirit of the invention.

EXAMPLES

Example 1: Sequence Selection and Oligonucleotide Modification Process

At first suitable sequences representing possible target sites were identified using proprietary bioinformatics tools. In a second step the effects of chemical modifications on these sequences were predicted in silico to optimize modification patterns.

Stepwise Sequence Selection Process.

Sequence lengths ranging from 13 mer length to 17 mer length were considered.

In the primary analysis the cross reactivity of potential target sites on the human PD-L1 mRNA (NM 014143.3) and cynomolgus monkey mRNA was investigated. Cross reactivity to non-human primates was considered as important for evaluation of exaggerated pharmacology. From the 16,380 sequences initially analyzed, about 50% showed 100% homology to the cynomolgus PD-L1 mRNA.

These sequences were further analyzed for specificity to the spliced human and cynomolgus transcriptomes applying following filters:
  No sequence should perfectly match (100%) any off-target region in human or monkey.
  By allowing one mismatch, a higher number of off-target mRNA matches were allowed for shorter sequences (e.g. 13 mers and 14 mers) compared to 15 mers and 16 mers.
  No 17 mer should show any predicted off-target binding in human and monkey allowing one mismatch.

Sequences fulfilling these criteria were further analyzed for specificity in the primary unspliced human and monkey transcriptome. Following filters were set:
  No sequence should perfectly match (100%) any pre-mRNA off-target region.
  No 17 mer should show any predicted off-target binding of pre-mRNA allowing one mismatch.

Analysis of the Effects of Chemical Modifications
  The effects of chemical modifications on physicochemical properties such as melting temperature and tendency to form hairpins or dimers were evaluated using available prediction tools. In total, 217 potential oligonucleotides based on the sequences with highest predicted specificity were analyzed using these tools
  Oligonucleotides with the most favorable predicted physicochemical properties were selected for synthesis (see Table 3) and in vitro screening (see Examples 2 to 4).

Example 2: In Vitro Screening of Antisense Oligonucleotides

Material:
  HDLM-2 cell line—DSMZ (Deutsche Sammlung für Mikroorganismen and Zelllinien, Braunschweig, Germany/ACC-17)

TABLE 1

Equipment used in the screening protocol

| | Manufacturer | Serial Number |
|---|---|---|
| Centrifuge | Heraeus Megafuge 16R | 75004270/41826277 |
| Laminar Flow | ThermoFisher | S2020 1.2/41820790 |
| Heracell Vios 16oi Incubator | ThermoFisher | |
| Clariostar BMG | BMG | |
| Novocyte 3000 Flow Cytometer | ACEA | 45-1-1405-1055-1 |

TABLE 2

Reagents used in the screening protocol

| | Manufacturer | Serial Number | Lot Number |
|---|---|---|---|
| RPMI1640 (fully supplemented) | | 20150921 TE Labbook 1 | |
| DMEM (fully supplemented) | | 20150921 TE Labbook 1 | |
| DEPC water | Ambion | AM9922 | 1506114 |
| 96wp flat bottom Nunclone Delta Surface | ThermoFisher | 167008 | 144112 |
| CellTiter Blue Reagent | Promega | G8088 | 152705 |
| Lysis Mixture | Affymetrix | 10093 | 2121507 |
| Proteinase K | Affymetrix | 12731 | 961504 |
| HPRT1 Probeset | Affymetrix | SA-10030 | 172411456 |
| CD274 (PD-L1) Probeset | Affymetrix | SA-17282 | 113575721 |
| PDL-1-PE (Clone 29E.2A3) | BioLegend | Cat. No: 329706 | B196393 |
| Mouse IgG2b, κ-PE (Clone MPC-11) | BioLegend | Cat. No: 400312 | B190187 |
| 7-AAD Viability staining solution | BioLegend | Cat. No: 420404 | B198482 |

TABLE 3

List of antisense oligonucleotides:

| Name | mRNA Sequence 5'-3' | SEQ ID NO: | Antisense Sequence 5'-3', partially with phosphorothioate linkages [*] and LNA modifications [+] | SEQ ID NO: |
|---|---|---|---|---|
| A03001H | GGATTACGTCTCC | 1 | +G*G*A*T*T*A*C*G*T*C*+T*C*+C | 2 |
| A03002H | TAGTTTGGCGACA | 3 | +T*+A*G*T*T*T*G*G*C*G*+A*+C*+A | 4 |
| A03003H | AGAAGCGCGGCTGG | 5 | +A*+G*+A*A*G*C*G*C*G*G*C*T*+G*+G | 6 |
| A03004H | TACCAAGTGAGTCC | 7 | +T*+A*+C*C*A*A*G*T*G*A*G*T*+C*+C | 8 |
| A03005H | GATTACGTCTCCTC | 9 | +G*+A*+T*T*A*C*G*T*C*T*C*+C*+T*+C | 10 |
| A03006H | TTCGCCAGGTTCCA | 11 | +T*+T*+C*G*C*C*A*G*G*T*T*+C*C*+A | 12 |
| A03007H | TTTCGCCAGGTTCC | 13 | +T*+T*+T*C*G*C*C*A*G*G*T*+T*C*+C | 14 |

TABLE 3-continued

List of antisense oligonucleotides:

| Name | mRNA Sequence 5'-3' | SEQ ID NO: | Antisense Sequence 5'-3', partially with phosphorothioate linkages [*] and LNA modifications [+] | SEQ ID NO: |
|---|---|---|---|---|
| A03008H | TTAGTTTGGCGACA | 15 | +T*+T*+A*G*T*T*T*G*C*G*+A*+C*+A | 16 |
| A03009H | GTGGTTACAGCGAT | 17 | +G*+T*+G*T*T*A*C*A*G*C*+G*+A*+T | 18 |
| A03010H | AGGACTAGATTGAC | 19 | +A*+G*+G*A*C*T*A*G*A*T*T*+G*+A*+C | 20 |
| A03011H | TCAAGCACAACGAA | 21 | +T*+C*+A*A*G*C*A*C*A*A*C*+G*+A*+A | 22 |
| A03012H | GAGTAGACTATGTG | 23 | +G*+A*+G*T*A*G*A*C*T*A*T*+G*+T*+G | 24 |
| A03013H | TGGTGCGGAGCCTCG | 25 | +T*G*+G*T*G*C*G*G*A*G*C*C*+T*C*+G | 26 |
| A03014H | GTTGTGTTGATTCTC | 27 | +G*+T*+T*G*T*G*T*T*G*A*T*T*+C*+T*+C | 28 |
| A03015H | GACCAATTCAGCTGT | 29 | +G*+A*+C*C*A*A*T*T*C*A*G*C*+T*+G*+T | 30 |
| A03016H | TTACCAAGTGAGTCC | 31 | +T*+T*+A*C*C*A*A*G*T*G*A*G*+T*+C*+C | 32 |
| A03017H | TGTCAGTGCTACACC | 33 | +T*G*+T*C*A*G*T*G*C*T*A*C*+A*C*+C | 34 |
| A03018H | ATTACGTCTCCTCCA | 35 | +A*+T*+T*A*C*G*T*C*T*C*C*T*+C*+C*+A | 36 |
| A03019H | TCGCCAGGTTCCATT | 37 | +T*+C*G*C*C*A*G*G*T*T*C*C*+A*+T*+T | 38 |
| A03020H | GGATTCTCAACCCGT | 39 | +G*G*+A*T*T*C*T*C*A*A*C*C*+C*+G*+T | 40 |
| A03021H | TTTAGTTTGGCGACA | 41 | +T*+T*+T*A*G*T*T*T*G*C*G*+A*+C*+A | 42 |
| A03022H | AGTTATAGAGGAGAC | 43 | +A*+G*+T*T*A*T*A*G*A*G*G*A*+G*+A*+C | 44 |
| A03023H | GGTGGTTACAGCGAT | 45 | +G*+G*+T*G*T*T*A*C*A*G*C*+G*+A*+T | 46 |
| A03024H | CCTTATGCTATGACA | 47 | +C*+C*+T*T*A*T*G*C*T*A*T*G*+A*+C*+A | 48 |
| A03025H | GGACTAGATTGACTC | 49 | +G*G*+A*C*T*A*G*A*T*T*G*A*+C*+T*+C | 50 |
| A03026H | TAGCAGTCAAGGTAC | 51 | +T*+A*+G*C*A*G*T*C*A*A*G*G*+T*+A*+C | 52 |
| A03027H | CGAATGAGGCTTTTC | 53 | +C*G*+A*A*T*G*A*G*G*C*T*T*+T*+T*+C | 54 |
| A03028H | CTGTGTAGTGATGAC | 55 | +C*+T*+G*T*G*T*A*G*T*G*A*T*+G*+A*+C | 56 |
| A03029H | GACTATGTGCCTTGC | 57 | +G*+A*+C*T*A*T*G*T*G*C*C*T*+T*+G*+C | 58 |
| A03030H | GATAAAGTGCCTTAC | 59 | +G*+A*+T*A*A*A*G*T*G*C*C*T*+T*+A*+C | 60 |
| A03031H | CCTATGCCATTTACG | 61 | +C*+C*+T*A*T*G*C*C*A*T*T*T*+A*+C*+G | 62 |
| A03032H | AGAAGCGCGGCTGGTG | 63 | +A*+G*+A*A*G*C*G*C*G*G*C*T*G*+G*+T*+G | 64 |
| A03033H | TCAGGACTTGATGGTC | 65 | +T*C*+A*G*G*A*C*T*T*G*A*T*G*+G*+T*+C | 66 |
| A03034H | CTCTCTTGGAATTGGT | 67 | +C*+T*+C*T*C*T*T*G*G*A*A*T*T*+G*+G*+T | 68 |
| A03035H | GACCAATTCAGCTGTA | 69 | +G*+A*+C*C*A*A*T*T*C*A*G*C*T*+G*+T*+A | 70 |
| A03036H | TTACCAAGTGAGTCCT | 71 | +T*+T*+A*C*C*A*A*G*T*G*A*G*T*+C*+C*+T | 72 |
| A03037H | TGTCAGTGCTACACCA | 73 | +T*+G*+T*C*A*G*T*G*C*T*A*C*A*+C*+C*+A | 74 |
| A03038H | AATGCTGGATTACGTC | 75 | +A*+A*+T*G*C*T*G*G*A*T*T*A*C*+G*+T*+C | 76 |
| A03039H | TTCGCCAGGTTCCATT | 77 | +T*+T*C*G*C*C*A*G*G*T*T*C*C*+A*+T*+T | 78 |
| A03040H | GCTTTCGCCAGGTTCC | 79 | +G*+C*+T*T*T*C*G*C*C*A*G*G*+T*+T*+C*+C | 80 |
| A03041H | AGTATCAAGGTCTCCC | 81 | +A*+G*+T*A*T*C*A*A*G*G*T*C*T*+C*+C*+C | 82 |
| A03042H | AGTTATAGAGGAGACC | 83 | +A*+G*+T*T*A*T*A*G*A*G*G*A*G*+A*+C*+C | 84 |
| A03043H | GTGGTTACAGCGATGA | 85 | +G*+T*+G*T*T*A*C*A*G*C*G*A*+T*+G*+A | 86 |
| A03044H | GATTGACTCAGTGCAC | 87 | +G*+A*+T*T*G*A*C*T*C*A*G*T*G*C*+A*+C | 88 |

TABLE 3-continued

List of antisense oligonucleotides:

| Name | mRNA Sequence 5'-3' | SEQ ID NO: | Antisense Sequence 5'-3', partially with phosphorothioate linkages [*] and LNA modifications [+] | SEQ ID NO: |
|---|---|---|---|---|
| A03045H | TAGCAGTCAAGGTACA | 89 | +T*+A*+G*C*A*G*T*C*A*A*G*G*T*+A*+C*+A | 90 |
| A03046H | GTTCAAGCACAACGAA | 91 | +G*+T*+T*C*A*A*G*C*A*C*A*A*C*+G*+A*+A | 92 |
| A03047H | GCCTATGCCATTTACG | 93 | +G*+C*+C*T*A*T*G*C*C*A*T*T*T*+A*+C*+G | 94 |
| A03048H | AGAAGCGCGGCTGGTGC | 95 | +A*+G*+A*A*G*C*G*C*G*G*C*T*G*G*+T*G*+C | 96 |
| A03049H | ACCAATTCAGCTGTATG | 97 | +A*+C*+C*A*A*T*T*C*A*G*C*T*G*T*+A*T*+G | 98 |
| A03050H | TGCTGGATTACGTCTCC | 99 | +T*+G*+C*T*G*G*A*T*T*A*C*G*T*C*+T*+C*+C | 100 |
| A03051H | TTTCGCCAGGTTCCATT | 101 | +T*+T*+T*C*G*C*C*A*G*G*T*T*C*C*+A*+T*+T | 102 |
| A03052H | GTATCAAGGTCTCCCTC | 103 | +G*+T*+A*T*C*A*A*G*G*T*C*T*C*C*+C*+T*+C | 104 |
| A03053H | GGTGGTTACAGCGATGA | 105 | +G*+G*+T*G*G*T*T*A*C*A*G*C*G*A*+T*+G*+A | 106 |
| A03054H | GGACTAGATTGACTCAG | 107 | +G*G*+A*C*T*A*G*A*T*T*G*A*C*T*+C*+A*+G | 108 |
| A03055H | ACAACGAATGAGGCTTT | 109 | +A*+C*+A*A*C*G*A*A*T*G*A*G*G*C*+T*+T*+T | 110 |
| A03056H | GACTGAGTAGACTATGT | 111 | +G*+A*+C*T*G*A*G*T*A*G*A*C*T*A*+T*G*+T | 112 |
| A03057H | GCCATTTACGATGAAAC | 113 | +G*+C*+C*A*T*T*T*A*C*G*A*T*G*A*+A*+A*+C | 114 |
| Neg1 | * | | +C*+G*+T*T*T*A*G*G*C*T*A*T*G*T*A*+C*+T*+T | |
| S6 | * | | +T*+C*+T*A*T*C*G*T*G*A*T*G*T*T*+T*+C*+T | |

* Neg1 (described in WO 2014/154843 A1) and S6 were used as control ASO in the experiments and do not hybridize with the human PD-L1 sequence (NM_014143.3)

Protocol:

HDLM-2 cell line was purchased from DSMZ, expanded for master and working cell banks and cultured in supplemented RPMI 1640 medium (5% CO$_2$ and 37° C.) for all further experiments. U-87MG cell line was purchased from ATCC, expanded for master and working cell banks and cultured in supplemented DMEM medium (5% CO$_2$ and 37° C.) for all further experiments. The cultivation periods of every thawed cell batch from the working cell bank were between two and three weeks.

All oligonucleotides were ordered from Exiqon (Vedbaek/Denmark). The lyophilized oligonucleotides were reconstituted with DEPC treated water up to concentration of 1 mM.

The initial screen to determine inhibition of target expression on RNA level was performed at a single concentration of 10 μM for each nucleotide.

Figure 1:
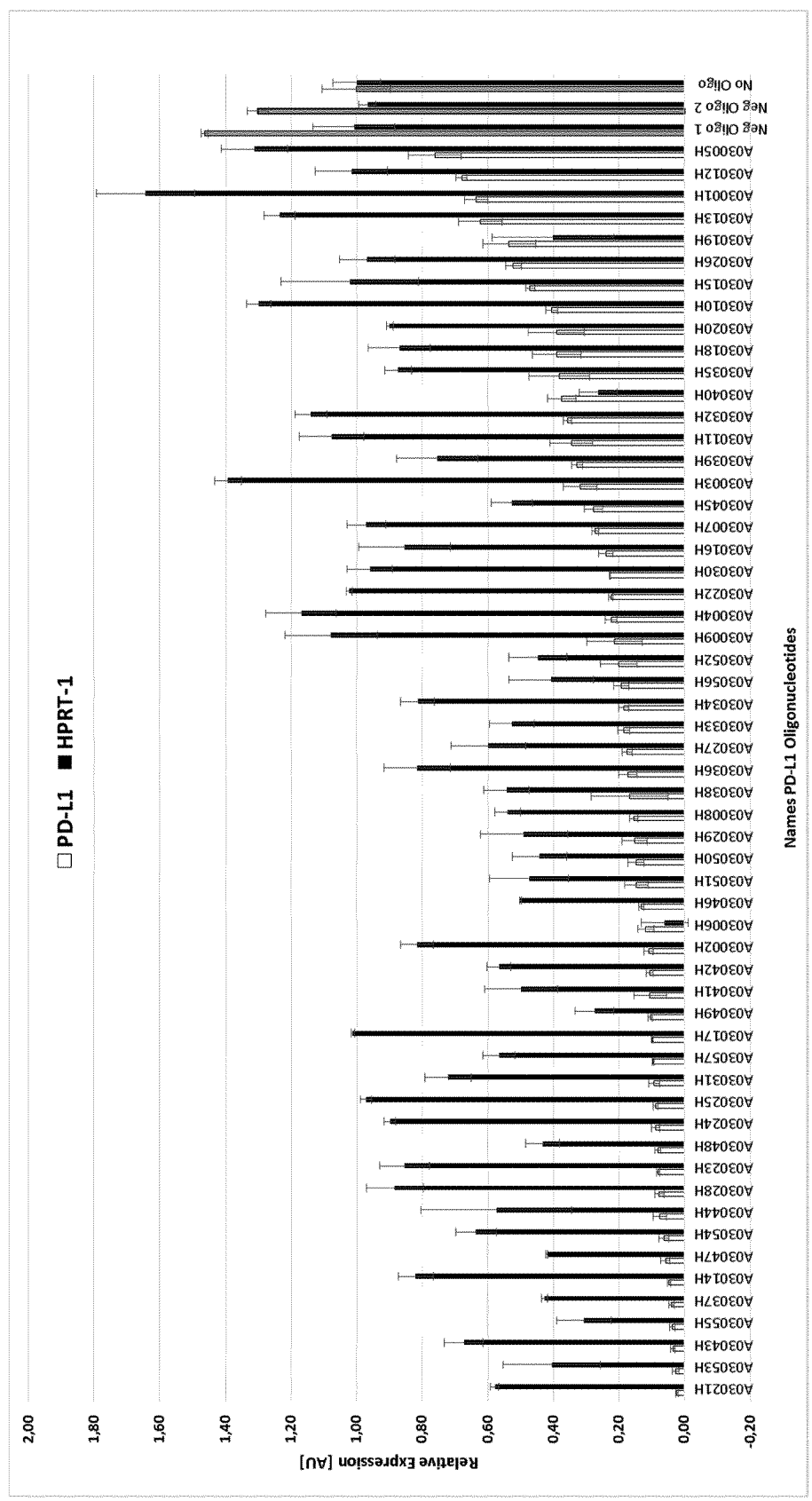
FIG. 1 shows the results of a first oligonucleotide screen for PD-L1 inhibition in HDLM-2 cells, as described in Example 2: for each construct, a pair of bars is shown: left, brighter bar: PD-L1 expression; right, darker bar: HPRT1 expression, including bars for a positive control (third pair from the left), and for a negative control oligonucleotide and a no-oligonucleotide control (two pairs on the right).

Therefore, HDLM-2 cells were seeded in supplemented RPM11640 at 15,000 cells/50 μl/well in 96 round bottom well plate. U-87MG cells were seeded in supplemented DMEM medium at 7,000 cells/50 μl/well in 96 round bottom well plate. Oligonucleotides were diluted in supplemented RPM11640 or DMEM respectively. For the starting concentration of 20 μM, 4 μl of oligonucleotide stock solution were diluted in 196 μl medium. Further, 50 μl of 20 μM (2×) oligonucleotide were added to each well of cells, leading to the final concentration of 10 μM. Each oligonucleotide was screened in triplicates (FIGS. 1/2).

One scrambled (negative) control, Neg1 and cells without oligonucleotide treatment ("no oligo control") were used as controls. "No oligo control" triplicates were set up on each 96 well plate. 50 μl of supplemented medium were added to "No Oligo" controls. All remaining wells were filled with 150 μl medium in order to prevent any evaporation effects.

Cells were incubated for 3 d at 37° C., 5% CO$_2$ without medium exchange. After 3 d, cells were lysed for the mRNA quantification via bDNA assay. For cell lysis each well was supplemented with 50 μl working lysis mixture and incubated 30 min at 50-55° C. The lysates were either used directly in a bDNA assay or frozen and stored. The working lysis mixture consisted of lysis mixture and Proteinase K. bDNA assay for HPRT1 and PD-L1 was performed according to the manufacturer's protocol.

Example 3: Downregulation of PD-L1 Protein Expression by Selected Antisense Oligonucleotides In order to investigate the potential of oligonucleotides towards target downregulation on protein level we selected five of the most active oligonucleotides as determined by the highest efficacy on target inhibition on RNA level in both cell lines. (Selected oligonucleotides: A03021; A03053; A03043; A03037; A03014). Therefore, different concentrations of each selected oligonucleotide and the scrambled (negative) control were used in triplicates starting at 10 μM; 1 μM; 0.5 μM; 0.1 μM; for each nucleotide. As control, cells were left untreated ("No Oligo") as described above. All remaining wells were filled with 150 μl medium in order to prevent any evaporation effects.

Accordingly, HDLM-2 cells were seeded in supplemented RPM11640 at 15,000 cells/50 μl/well in 96 round bottom well plate. For the starting concentration of 20 μM, 8 μl of oligonucleotide stock solution were diluted in 392 μl medium. Furthermore, 50 μl of 20 μM (2×) oligonucleotide were added to each well of cells, leading to the final concentration of 10 µM. To receive a final concentration of 1 µM in each well, 1.6 µL of each oligonucleotide were dissolved in 798.4 µL medium and 50 µl of the 2 µM (2×) solution were added to 50 µl of cells. 400 µl of the 2 µM stock solution were further diluted with 400 µl of medium (c=1 µM) and 50 µl of the 1 µM (2×) solution were added to 50 µl of cells (0.5 µM final concentration). 400 µl of the 1 µM stock solution were further diluted with 1,600 µl of medium (c=0.2 µM) and 50 µl of the 0.2 µM (2×) solution were added to 50 µl of cells (0.1 µM final concentration).

PD-L1 Protein expression levels were determined on HDLM-2 cells at different time points (24 h, 48 h, 72 h and 96 h) after oligonucleotide treatment by flow cytometry using an ACEA Novocyte3000. Therefore, cells were stained with the following antibodies: Anti-Human PDL-1-PE (Clone 29E.2A3); Mouse IgG2b,κ-PE Isotype control (Clone MPC-11); and 7-AAD to exclude dead cells (all from BioLegend). Each well of cells was stained in 50 µl of FACS Buffer (5% FCS; 2 mM EDTA in 1×PBS). Fluorescent antibodies were used at a 1:200; 7_AAD at a 1:100 dilution in FACS buffer.

TABLE 4

Equipment used for investigation of A03043H efficiency in primary human dendritic cells

| | Manufacturer | Serial Number |
| --- | --- | --- |
| Centrifuge | Heraeus Megafuge 16R | 75004270/41826277 |
| Laminar Flow | ThermoFisher | S2020 1.2/41820790 |
| Heracell Vios 16oi Incubator | ThermoFisher | |
| Novocyte 3000 Flow Cytometer | ACEA | 45-1-1405-1055-1 |

TABLE 5

Reagents used for investigation of A03043H efficiency in primary human dendritic cells

| | Manufacturer | Catalog number | Lot Number |
| --- | --- | --- | --- |
| Buffycoat#2 (BC#2) | Blutspendedienst BRK | | 80216137173 |
| RPMIfs | RPMI_160401RK | | |
| Biocoll | Millipore | L6115 | 1342D |
| PBS | Gibco | 1404-133 | 1710584 |
| 80cm2 flask | Nunc | 178905 | 144931 |
| GM-CSF | Peprotech | 300-03 | 011330-1 |
| IL-4 | Peprotech | 200-04 | 111414 |
| IFNg | Peprotech | 300-02 | 71527 |
| LPS | Sigma | L4391-1MG | 115M4090V |
| 80cm2 flask, Nuclon surface | NUNC | 178905 | 144931 |
| 48wp | Thermo | 150687 | 145530 |
| Human True stain FcX | Biolegend | B205592 | 422302 |
| PDL-1-PE (Clone 29E.2A3) | BioLegend | 329706 | B196393 |
| Mouse IgG2b, κ-PE (Clone MPC-11) | BioLegend | 400312 | B190187 |
| Fixable viability Dye eF506 | eBioscience | 65-0866-14 | 4296953 |
| FCS | Gibco | 10270-106 | 41F5243K |

Protocol:

1. Purification of Peripheral Blood Mononucleated Cells (PBMC)

25 ml of BC#2 were diluted with PBS to a final volume of 350 ml. 35 ml of the dilution were layered over 15 ml Biocoll in a 50 ml Falcon tube. After centrifugation at 800 g for 20 min without break (room temperature) the mononuclear cell layer was carefully transferred into a new 50 ml Falcon tube. The tube was filled with PBS to 50 ml and centrifuged for at 500 g for 5 min (room temperature). Washing was repeated once and cell pellets were subsequently pooled and counted.

2. Generation of Immature Dendritic Cells (iDC)

100 Mio PBMC were seeded in 12 ml RPMIfs in an 80 cm² flask for plastic adherence-based monocyte enrichment. After 2 h incubation at 37° C. non-adherent cells were removed and the monocyte layer was carefully washed with RPMIfs two times. Finally, 12 ml RPMIfs supplemented with 10 ng/ml IL-4 and 40 ng/ml GM-CSF were added and cells were incubated at 37° C. for 72 h.

3. Maturation and Antisense Oligonucleotide Treatment of Immature Dendritic Cells iDC (non- and weakly-adherent) were harvested and counted. 50 000 iDC were seeded per well of a 48 well plate in 250 µl RPMIfs supplemented with GM-CSF (final concentration: 40 ng/ml), IL-4 (final concentration: 10 ng/ml), IFN-g (final concentration: 1000 U/ml) and LPS (final concentration: 1 µg/ml). For the untreated control, 250 µl of RPMIfs were added per well, for all other conditions 250 µl were supplemented with the respective antisense oligonucleotide to the final concentrations indicated in Table 9. Cells were incubated at 37° C. for 72 h.

4. Analysis of PD-L1 Protein Expression by Flow Cytometry

Mature DC (mDC) were harvested and washed once in PBS/1% FCS (FACS buffer). Fc receptors were blocked for 5 min in 50 µl PBS supplemented with 1 µl True stain FcX. For staining, the respective antibody and the viability dye were added in 50 µl PBS diluted 1:25 and 1:2000, respectively. After 20 min incubation at 4° C. cells were washed twice in FACS buffer and analyzed by flow cytometry.

Figure 2:
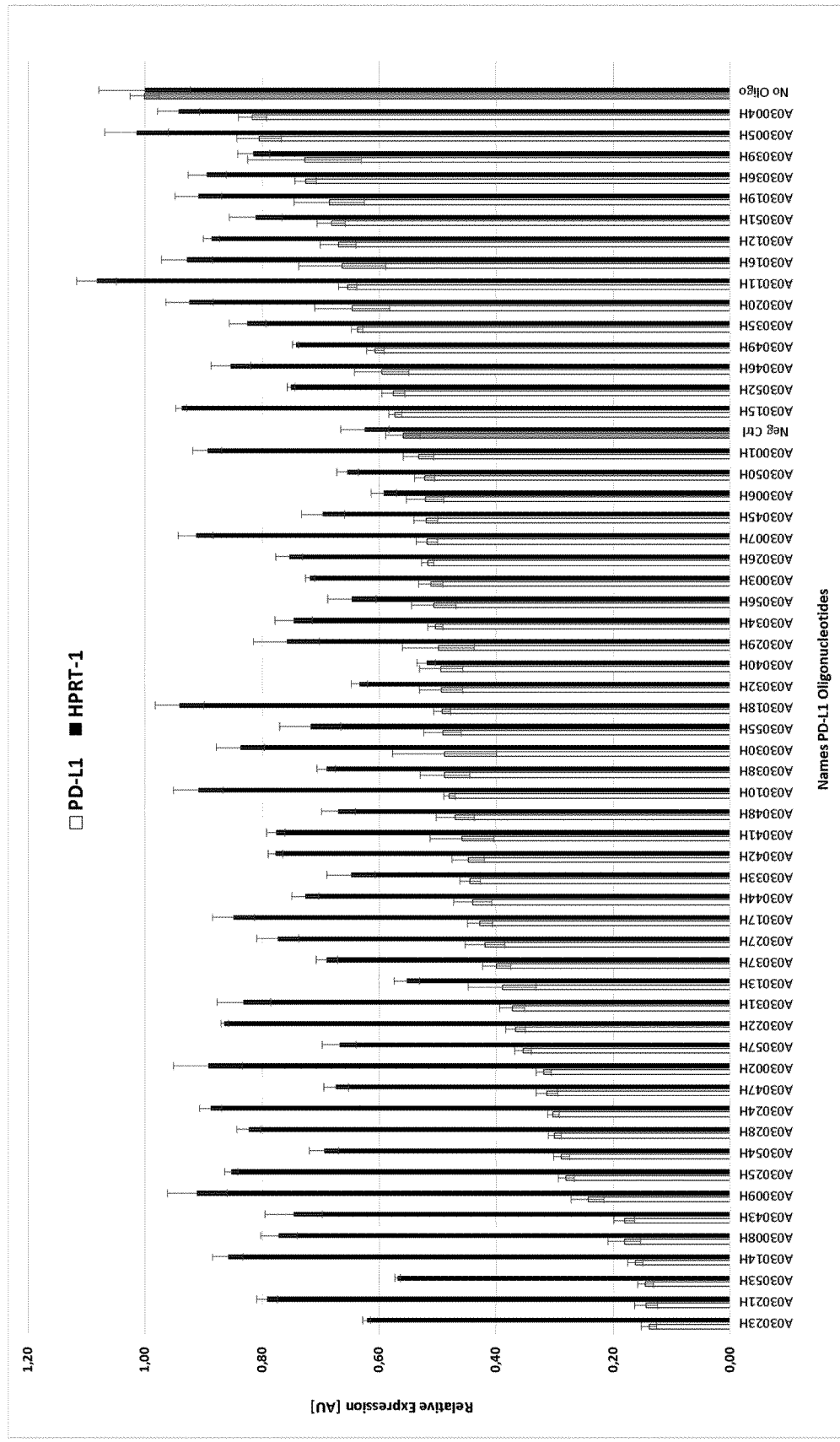
FIG. 2 shows the results of a first oligonucleotide screen for PD-L1 inhibition in U-87MG cells, as described in Example 2: for each construct, a pair of bars is shown: left, brighter bar: PD-L1 expression; right, darker bar: HPRT1 expression, including bars for a positive control ($15^{th}$ pair from the left), and for a negative control oligonucleotide ($17^{th}$ pair from the right, and a no-oligonucleotide control (last pair on the right).

Results:

The initial selection of antisense oligonucleotides in HDLM-2 cells (FIG. 1) and U-87MG cells (FIG. 2) resulted in several highly active molecules. The relative expression levels of HPRT1 (housekeeping gene) and PD-L1 were calculated and plotted for all antisense oligonucleotides and untreated controls in HDLM-2 cells (FIG. 1/Table 6) and U-87MG cells (FIG. 2/Table 7).

TABLE 6

Relative expression of HPRT1 and PD-L1 in HDLM-2 cells

| | Relative Expression [AU] | |
|---|---|---|
| | PD-L1 | HPRT1 |
| A03021H | 0.02 | 0.58 |
| A03053H | 0.03 | 0.40 |
| A03043H | 0.03 | 0.67 |
| A03055H | 0.04 | 0.31 |
| A03037H | 0.04 | 0.43 |
| A03014H | 0.05 | 0.82 |
| A03047H | 0.06 | 0.42 |
| A03054H | 0.06 | 0.64 |
| A03044H | 0.07 | 0.57 |
| A03028H | 0.08 | 0.88 |
| A03023H | 0.08 | 0.85 |
| A03048H | 0.08 | 0.43 |
| A03024H | 0.09 | 0.90 |
| A03025H | 0.09 | 0.97 |
| A03031H | 0.09 | 0.72 |
| A03057H | 0.09 | 0.56 |
| A03017H | 0.10 | 1.01 |
| A03049H | 0.10 | 0.27 |
| A03041H | 0.10 | 0.50 |
| A03042H | 0.11 | 0.57 |
| A03002H | 0.11 | 0.82 |
| A03006H | 0.12 | 0.06 |
| A03046H | 0.13 | 0.50 |
| A03051H | 0.15 | 0.47 |
| A03050H | 0.15 | 0.44 |
| A03029H | 0.15 | 0.49 |
| A03008H | 0.15 | 0.54 |
| A03038H | 0.17 | 0.54 |
| A03036H | 0.17 | 0.81 |
| A03027H | 0.17 | 0.60 |
| A03033H | 0.18 | 0.53 |
| A03034H | 0.18 | 0.81 |
| A03056H | 0.19 | 0.41 |
| A03052H | 0.20 | 0.45 |
| A03009H | 0.21 | 1.08 |
| A03004H | 0.22 | 1.17 |
| A03022H | 0.22 | 1.02 |
| A03030H | 0.23 | 0.96 |
| A03016H | 0.24 | 0.85 |
| A03007H | 0.27 | 0.97 |
| A03045H | 0.28 | 0.53 |
| A03003H | 0.32 | 1.39 |
| A03039H | 0.33 | 0.75 |
| A03011H | 0.34 | 1.07 |
| A03032H | 0.36 | 1.14 |
| A03040H | 0.37 | 0.26 |
| A03035H | 0.38 | 0.87 |
| A03018H | 0.39 | 0.87 |
| A03020H | 0.39 | 0.90 |
| A03010H | 0.41 | 1.30 |
| A03015H | 0.47 | 1.02 |
| A03026H | 0.52 | 0.97 |
| A03019H | 0.53 | 0.40 |
| A03013H | 0.62 | 1.23 |
| A03001H | 0.63 | 1.64 |
| A03012H | 0.68 | 1.01 |
| A03005H | 0.76 | 1.31 |
| Neg. Oligo 1 | 1.46 | 1.01 |
| Neg. Oligo 2 | 1.30 | 0.97 |
| No Oligo | 1.00 | 1.00 |

TABLE 7

Relative expression of HPRT1 and PD-L1 in U-87MG cells

| | Relative Expression [AU] | |
|---|---|---|
| | PD-L1 | HPRT1 |
| A03023H | 0.14 | 0.62 |
| A03021H | 0.14 | 0.79 |
| A03053H | 0.14 | 0.57 |
| A03014H | 0.16 | 0.86 |
| A03008H | 0.18 | 0.77 |
| A03043H | 0.18 | 0.75 |
| A03009H | 0.24 | 0.91 |
| A03025H | 0.28 | 0.85 |
| A03054H | 0.29 | 0.69 |
| A03028H | 0.30 | 0.82 |
| A03024H | 0.30 | 0.89 |
| A03047H | 0.31 | 0.67 |
| A03002H | 0.32 | 0.89 |
| A03057H | 0.35 | 0.67 |
| A03022H | 0.37 | 0.86 |
| A03031H | 0.37 | 0.83 |
| A03013H | 0.39 | 0.55 |
| A03037H | 0.40 | 0.69 |
| A03027H | 0.42 | 0.77 |
| A03017H | 0.43 | 0.85 |
| A03044H | 0.44 | 0.73 |
| A03033H | 0.44 | 0.65 |
| A03042H | 0.45 | 0.78 |
| A03041H | 0.46 | 0.78 |
| A03048H | 0.47 | 0.67 |
| A03010H | 0.48 | 0.91 |
| A03038H | 0.49 | 0.69 |
| A03030H | 0.49 | 0.84 |
| A03055H | 0.49 | 0.72 |
| A03018H | 0.49 | 0.94 |
| A03032H | 0.49 | 0.63 |
| A03040H | 0.49 | 0.52 |
| A03029H | 0.50 | 0.76 |
| A03034H | 0.50 | 0.75 |
| A03056H | 0.51 | 0.65 |
| A03003H | 0.51 | 0.72 |
| A03026H | 0.52 | 0.75 |
| A03007H | 0.52 | 0.91 |
| A03045H | 0.52 | 0.70 |
| A03006H | 0.52 | 0.59 |
| A03050H | 0.52 | 0.65 |
| A03001H | 0.53 | 0.89 |
| Neg Ctrl | 0.56 | 0.62 |
| A03015H | 0.57 | 0.94 |
| A03052H | 0.58 | 0.75 |
| A03046H | 0.60 | 0.85 |
| A03049H | 0.61 | 0.74 |
| A03035H | 0.64 | 0.82 |
| A03020H | 0.65 | 0.92 |
| A03011H | 0.65 | 1.08 |
| A03016H | 0.66 | 0.93 |
| A03012H | 0.67 | 0.89 |
| A03051H | 0.68 | 0.81 |
| A03019H | 0.68 | 0.91 |
| A03036H | 0.72 | 0.89 |
| A03039H | 0.73 | 0.81 |
| A03005H | 0.80 | 1.01 |
| A03004H | 0.82 | 0.94 |
| No Oligo | 1.00 | 1.00 |

Figure 3:
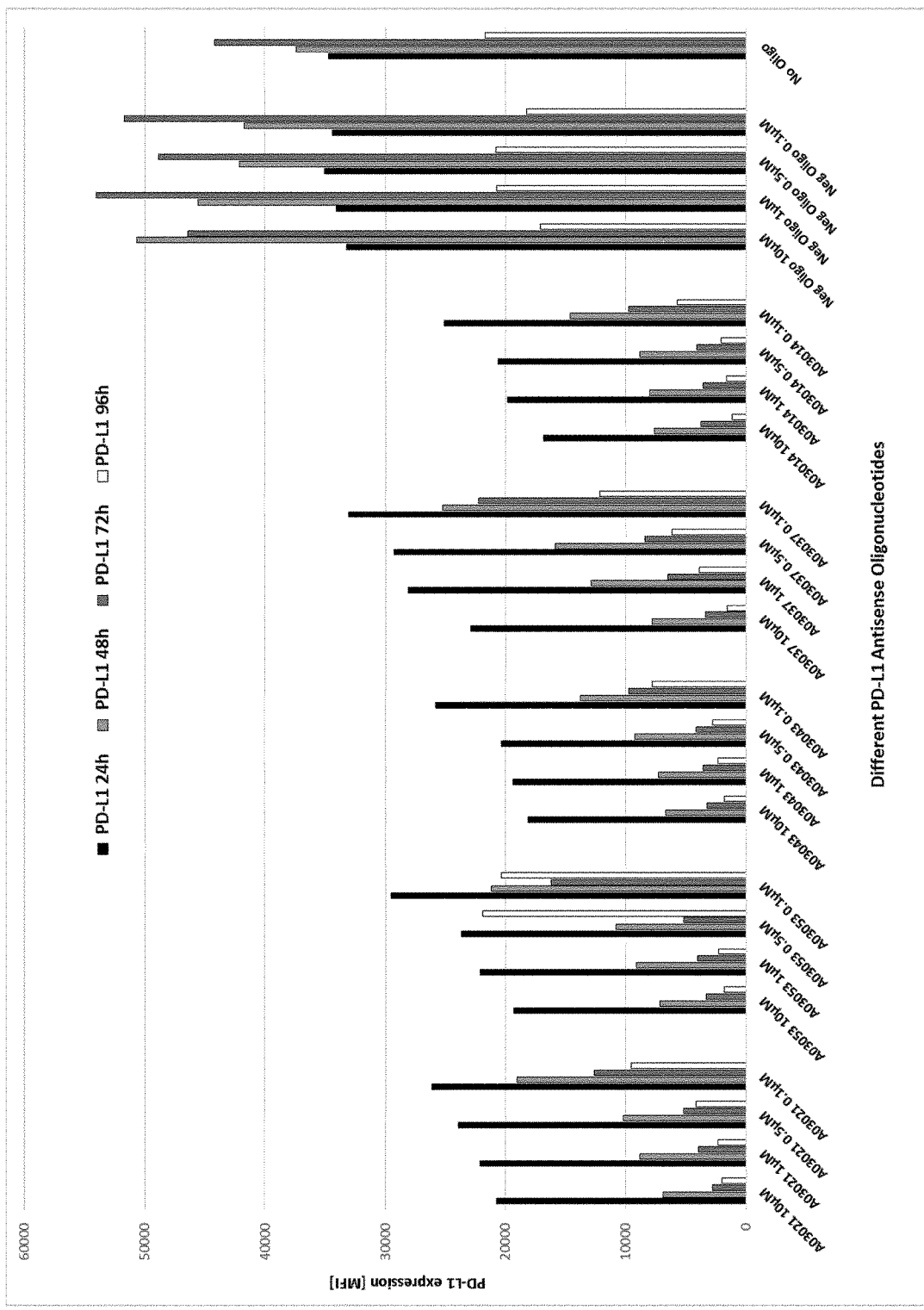
FIG. 3 shows the results of the addition of different concentrations (10 µM; 1 µM; 0.5 µM; 0.1 µM) of selected oligonucleotides (A03021; A03053; A03043; A03037; A03014) to HDLM-2 cells as described in Example 3. PD-L1 protein levels were determined by flow cytometry at different time points (24 h=black bars; 48 h=light grey bars; 72 h=dark grey bars; 96 h=white bars) after oligo treatment. PD-L1 protein expression per cell is depicted as Mean Fluorescence Intensity (MFI).

Five selected Oligonucleotides against PD-L1 RNA (A03021; A03053; A03043; A03037; A03014) showed great potential in downregulating PD-L1 protein, leading to a maximum inhibition of 95%, 72 h after treatment at different concentrations (10-0.5 μM) when compared to "Neg Oligo" or "No Oligo" treated cells (FIG. 3/Tab. 8).

TABLE 8

PD-L1 Protein expression (Mean Fluorescence Intensity [MFI]) per cell on HDLM-2 cells after addition of different concentrations of oligonucleotides after different time points

| Concentration of different Oligonucleotides | PD-L1 24 h [MFI] | PD-L1 48 h [MFI] | PD-L1 72 h [MFI] | PD-L1 96 h [MFI] |
|---|---|---|---|---|
| A03021 10 µM | 20752 | 6884 | 2785 | 2006 |
| A03021 1 µM | 22067 | 8842 | 3936 | 2308 |
| A03021 0.5 µM | 23909 | 10250 | 5198 | 4109 |
| A03021 0.1 µM | 26070 | 19041 | 12605 | 9573 |
| A03053 10 µM | 19268 | 7188 | 3276 | 1793 |
| A03053 1 µM | 22094 | 9150 | 4008 | 2248 |
| A03053 0.5 µM | 23657 | 10797 | 5139 | 21875 |
| A03053 0.1 µM | 29530 | 21195 | 16202 | 20344 |
| A03043 10 µM | 18131 | 6688 | 3215 | 1786 |
| A03043 1 µM | 19353 | 7303 | 3523 | 2323 |
| A03043 0.5 µM | 20333 | 9257 | 4154 | 2757 |
| A03043 0.1 µM | 25758 | 13756 | 9777 | 7834 |
| A03037 10 µM | 22851 | 7826 | 3344 | 1533 |
| A03037 1 µM | 28111 | 12902 | 6461 | 3889 |
| A03037 0.5 µM | 29268 | 15870 | 8403 | 6115 |
| A03037 0.1 µM | 33028 | 25174 | 22219 | 12170 |
| A03014 10 µM | 16828 | 7655 | 3748 | 1138 |
| A03014 1 µM | 19806 | 8032 | 3521 | 1634 |
| A03014 0.5 µM | 20596 | 8829 | 4066 | 2046 |
| A03014 0.1 µM | 25062 | 14653 | 9760 | 5694 |
| Neg Oligo 10 µM | 33209 | 50651 | 46368 | 17064 |
| Neg Oligo 1 µM | 34043 | 45547 | 54028 | 20702 |
| Neg Oligo 0.5 µM | 35051 | 42127 | 48820 | 20815 |
| Neg Oligo 0.1 µM | 34411 | 41741 | 51687 | 18243 |
| No Oligo | 34698 | 37367 | 44209 | 21719 |

Figure 4:
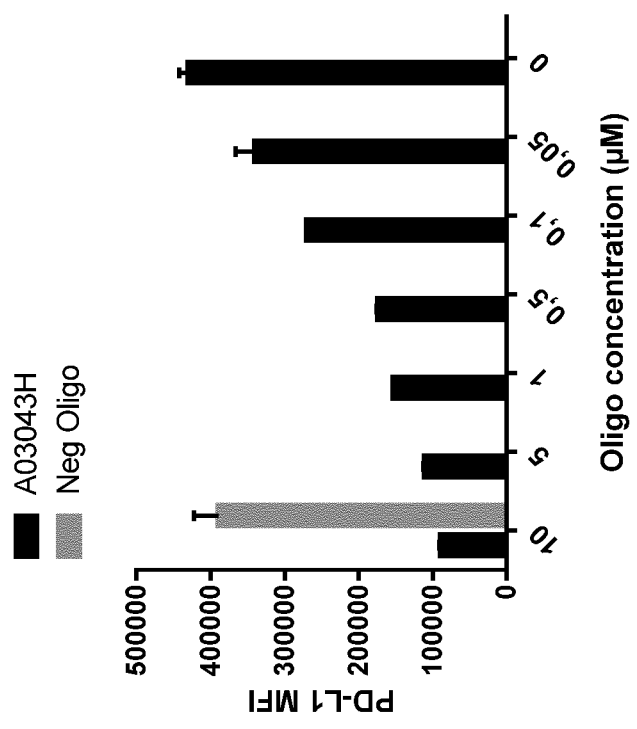
FIG. 4 shows the results of the addition of different concentrations (10 µM; 5 µM; 1 µM; 0.5 µM; 0.1 µM; 0.05 µM) of oligonucleotide A03043H to primary human dendritic cells as described in Example 3. PD-L1 protein levels were determined by flow cytometry 72 h after oligo treatment. PD-L1 protein expression per cell is depicted as Median Fluorescence Intensity (MFI).

The Oligonucleotide A03043 shows great potential in the downregulation of PD-L1 on mature primary dendritic cells as compared to untreated dendritic cells or Neg Oligo-treated dendritic cells (Table 9 and FIG. 4).

TABLE 9

PD-L1 protein expression (Median Fluorescence Intensity) per cell on mature primary human dendritic cells after 72 h

| Concentration of Oligonucleotide | PD-L1 72 h [MFI] (Replicate 1) | PD-L1 72 h [MFI] (Replicate 2) | % PD-L1 down-regulation vs. Neg Oligo (mean) | % PD-L1 down-regulation vs. No Oligo (mean) |
|---|---|---|---|---|
| A03043H 10 µM | 90478 | 87773 | 77 | 79 |
| A03043H 5 µM | 111899 | 110400 | 71 | 74 |
| A03043H 1 µM | 153129 | 153647 | 61 | 64 |
| A03043H 0.5 µM | 175248 | 173483 | 55 | 59 |
| A03043H 0.1 µM | 268960 | 270780 | 31 | 37 |
| A03043H 0.05 µM | 321606 | 358261 | 13 | 21 |
| Neg Oligo 10 µM | 366820 | 413000 | −10 | 0 |
| No Oligo | 421000 | 439000 | 0 | 9 |

Example 4: Determination of $IC_{50}$ Values of Selected Antisense Oligonucleotides Typically target activity of RNase H active antisense oligonucleotides is determined by measurement of target mRNA levels after transfection of the oligonucleotides into the cells using transfection reagents or after electroporation.

For example activity of the Bcl-2-specific LNA-modified oligonucleotide SPC 2996 (Santaris Pharma, now Roche Innovation Center Copenhagen) was demonstrated only after transfection (U.S. Pat. No. 7,622,453 B2).

While target activity of LNA- or c-ET-modified oligonucleotides without transfection reagents has been shown before (so called gymnotic delivery/gymnosis or unassisted transfection), relatively high oligonucleotide concentrations were required for potent target suppression.

For example, the LNA-modified oligonucleotides specific for PCSK9 (U.S. Pat. No. 8,563,528 B2) showed only moderate activity without transfection reagents (U.S. Pat. No. 8,563,528 B2, FIG. 3. The best performing oligonucleotide (SEQ ID NO: 4) only achieved target suppression of approximately 70% at a concentration of 10 µM.

In the literature, $IC_{50}$ values between 300 and 600 nM have been described for LNA-modified oligonucleotides against cancer targets without transfection (Zhang et al. Gene Therapy (2011) 18, 326-333).

Protocol:

$IC_{50}$ values of the most potent PDL-1 oligonucleotides were determined in HDLM-2 cells (15,000 cells/well). Therefore, HDLM-2 cells were treated for 3 days with different concentrations (10; 3.33; 1.11; 0.37; 0.12; 0.041; 0.0045 µM) of selected PD-L1 oligonucleotides as described above. On day 3 after culture, cells were lysed and RNA levels were determined by bDNA assay according to the manufacturer's protocol. Relative $IC_{50}$ values were calculated using GraphPadPrism 6 Software (see Table 10).

TABLE 10

List of human PD-L1 $IC_{50}$ values determined in HDLM-2 cells

| | $IC_{50}$ [nM] |
|---|---|
| A03014H | 13.26 |
| A03043H | 15.31 |
| A03021H | 19.6 |
| A03047H | 48.62 |
| A03053H | 49.45 |
| A03037H | 78.82 |

Results:

In contrast to the prior art discussed above, oligonucleotides described in the present invention show potent and specific target suppression without the requirement of transfection reagents or electroporation. In contrast to prior art reports, a significant proportion of oligonucleotides in the present invention suppressed PD-L1 mRNA by more than 90% at 10 µM.

Furthermore, $IC_{50}$ values of the best-performing oligonucleotides described in the present invention were surprisingly below 20 nM.

Example 5: Generation of Murine Antisense Oligonucleotides

The sequences of human and murine PD-L1 show a rather low degree of homology. Therefore, no cross-reactive antisense oligonucleotides could be generated. In order to be able to show the proof-of-concept of a PD-L1-based antisense approach in a murine in vivo model, antisense oligonucleotides with specificity for murine PD-L1 had to be developed as surrogates for showing in vivo efficacy.

Protocol:

Mouse Renca and 4T1 cell lines were purchased from ATCC, expanded for master and working cell banks and cultured in supplemented DMEM medium (5% $CO_2$ and 37° C.) for all further experiments. The cultivation periods of every thawed cell batch from the working cell bank were between two and three weeks.

All oligonucleotides, which were designed based on the mRNA sequence of murine PD-L1 (CD274) sequence (NM 021893.3); SEQ ID No 116, see Table 16), were ordered from Exiqon (Vedbaek/Denmark). The lyophilized oligonucleotides were reconstituted with DEPC treated water up to concentration of 1 mM.

The initial screen to determine inhibition of target expression on RNA level was performed at a single concentration of 10 µM for each nucleotide.

Figure 6:
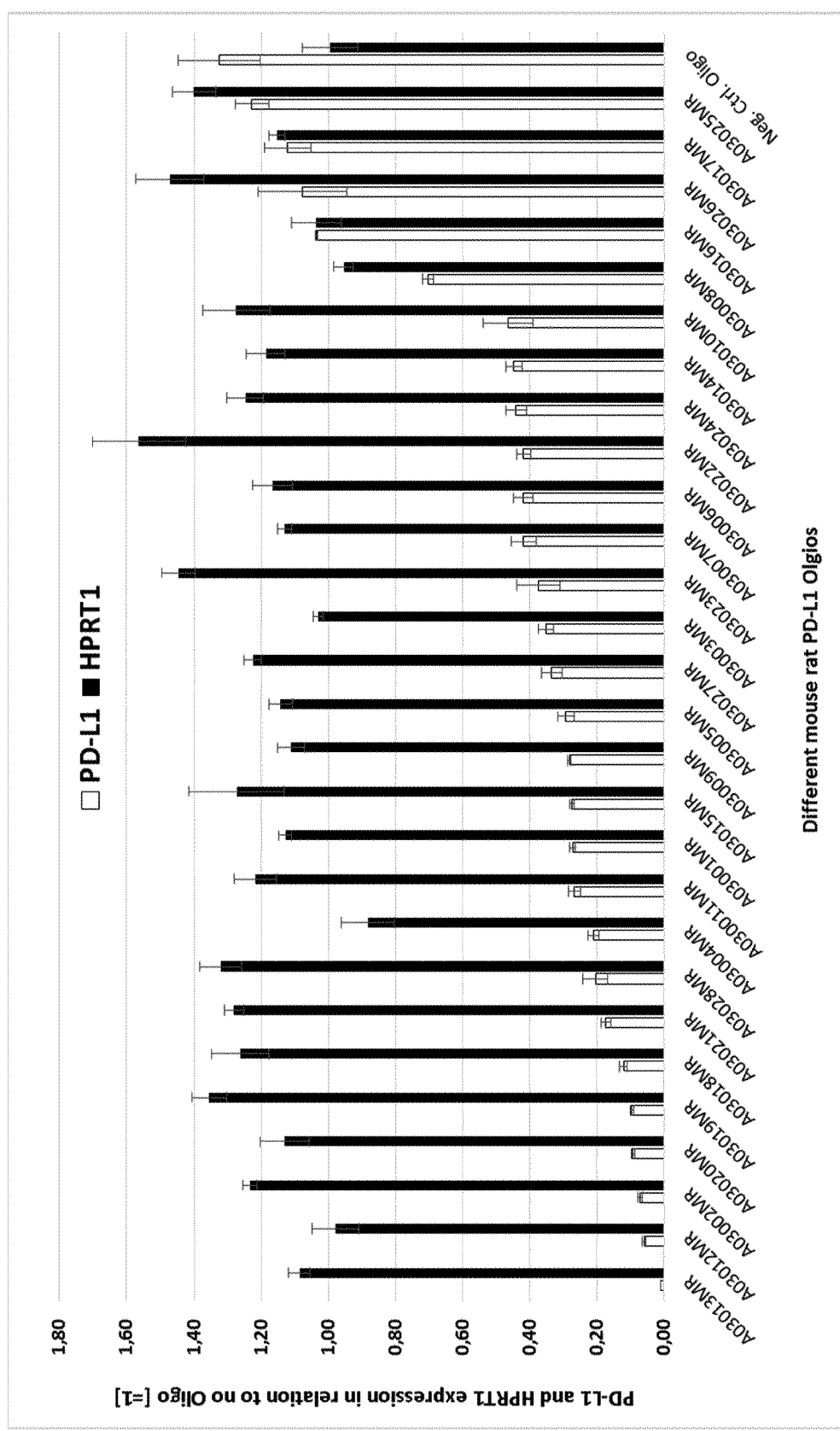
FIG. 6 shows the results of an oligonucleotide screen for murine PD-L1 inhibition in RENCA cells, as described in Example 5: for each construct, a pair of bars is shown: left, brighter bar: murine PD-L1 expression; right, darker bar: murine HPRT1 expression, both in relation to a no oligo control (=1.00), including bars for a negative control oligonucleotide (pair of bars on the right).

Therefore, Renca cells were cultured at 15.000 cells and 4T1 cells were cultured at 6000 cells/50 µl/well in supplemented DMEM in 96 round bottom well plate. For the starting concentration of 20 µM, 4 µl of oligonucleotide stock solution were diluted in 196 µl medium. Further, 50 µl of 20 µM (2×) oligonucleotide were added to each well of cells, leading to the final concentration of 10 µM. Each oligonucleotide was screened in triplicates (FIGS. 6/7).

One scrambled (negative) control, Neg1 and cells without oligonucleotide treatment ("no oligo control") were used as controls. "No oligo control" triplicates were set up on each 96 well plate. 50 µl of supplemented medium were added to "No Oligo" controls. All remaining wells were filled with 150 µl medium in order to prevent any evaporation effects.

Cells were incubated for 3 d at 37° C., 5% $CO_2$ without medium exchange. After 3 d, cells were lysed for the mRNA quantification via bDNA assay. For cell lysis each well was supplemented with 50 µl working lysis mixture and incubated 30 min at 50-55° C. The lysates were either used directly in a bDNA assay or frozen and stored. The working lysis mixture consisted of lysis mixture and Proteinase K. bDNA assay for HPRT1 and PD-L1 was performed according to the manufacturer's protocol.

Figure 7:
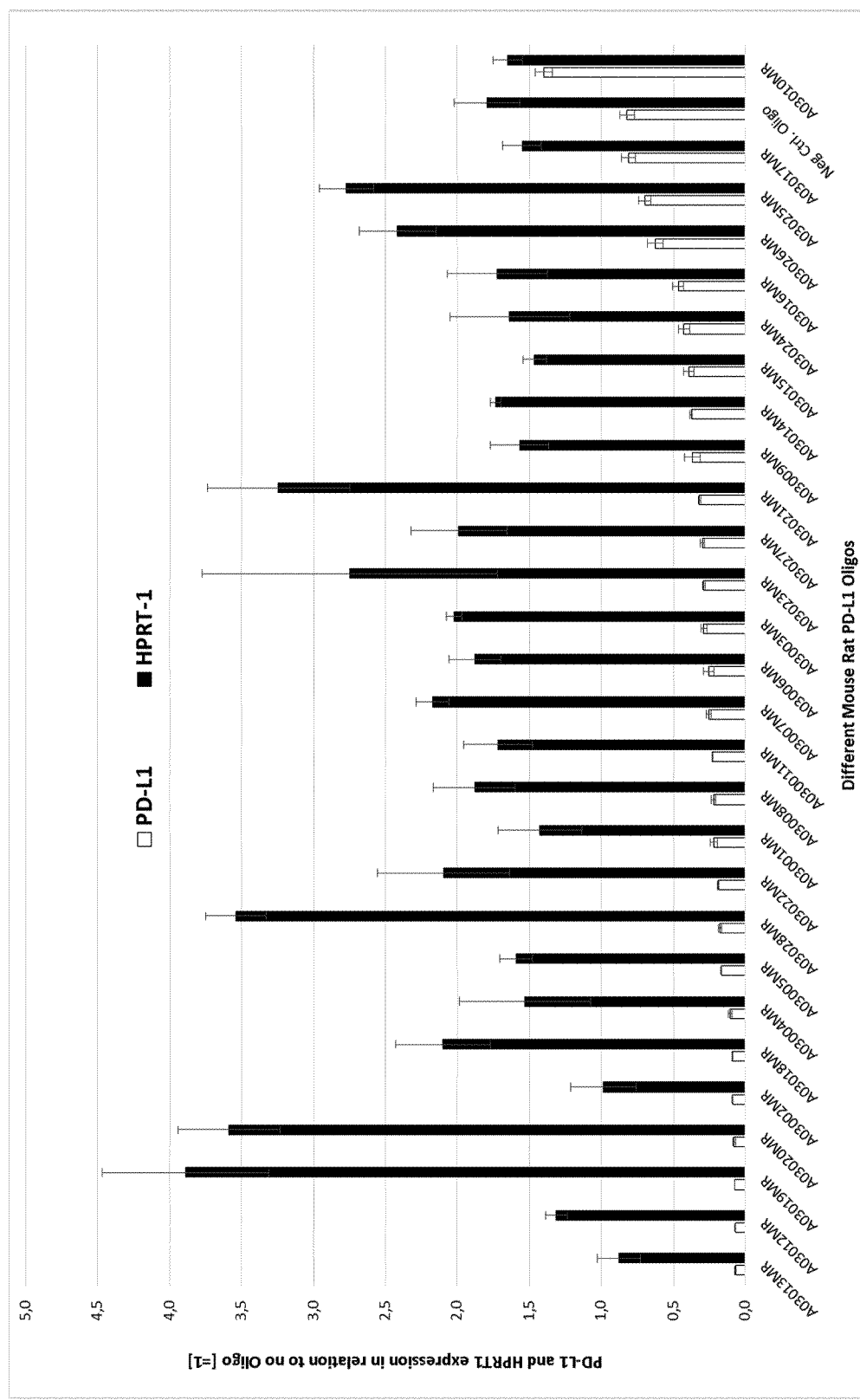
FIG. 7 shows the results of a first oligonucleotide screen for murine PD-L1 inhibition in 4T1 cells, as described in Example 5: for each construct, a pair of bars is shown: right, brighter bar: murine PD-L1 expression; left, darker bar: murine HPRT1 expression, both in relation to a no oligo control (=1.00), including bars for a negative control oligonucleotide (second pair of bars from the right).

Results:

The initial selection of antisense oligonucleotides in RENCA cells (FIG. 6) and 4T1 cells (FIG. 7) resulted in several highly active molecules. The relative expression levels of HPRT1 (housekeeping gene) and PD-L1 were calculated and plotted for all antisense oligonucleotides and untreated controls in RENCA cells (FIG. 6/Table 12) and 4T1 cells (FIG. 7/Table 13).

TABLE 11

List of mouse/rat antisense oligonucleotides:

| Oligo Length | Name | SEQ ID NO | Antisense Sequence 5'-3', partially with phosphorothioate linkages [*] and LNA modifications [+] |
|---|---|---|---|
| 15 | A03001MR | 117 | +A*+T*+A*C*T*C*C*A*C*C*A*C*G*T*+A*+C*+A |
| 15 | A03002MR | 118 | +G*+C*+C*A*T*A*C*T*C*C*A*C*C*A*+C*+G*+T |
| 15 | A03003MR | 119 | +G*+A*+T*T*C*G*C*T*T*G*T*A*G*T*+C*+C*+G |
| 15 | A03004MR | 120 | +G*+C*+T*T*A*C*G*T*C*T*C*C*T*C*+G*+A*+A |
| 15 | A03005MR | 121 | +C*+A*+A*C*A*C*T*G*C*T*T*A*C*G*+T*+C*+T |
| 16 | A03006MR | 122 | +G*+T*+T*C*A*A*C*A*C*T*G*C*T*T*+A*+C*+G |
| 16 | A03007MR | 123 | +G*+G*+T*T*C*A*A*C*A*C*T*G*C*T*+T*+A*+C |
| 16 | A03008MR | 124 | +A*+C*+A*A*A*C*T*C*G*G*T*G*A*G*+T*+A*+C |
| 16 | A03009MR | 125 | +T*+A*+C*T*C*C*A*C*C*A*C*G*T*+A*+C*+A |
| 16 | A03010MR | 126 | +A*+T*+A*C*T*C*C*A*C*C*A*C*G*+T*+A*+C |
| 16 | A03011MR | 127 | +C*+A*+T*A*C*T*C*C*A*C*C*A*C*+G*+T*+A |
| 16 | A03012MR | 128 | +C*+C*+A*T*A*C*T*C*C*A*C*C*A*+C*+G*+T |
| 16 | A03013MR | 129 | +G*+C*+C*A*T*A*C*T*C*C*A*C*C*+A*+C*+G |
| 16 | A03014MR | 130 | +T*+T*+C*G*C*T*T*G*T*A*G*T*C*+C*+G*+C |
| 16 | A03015MR | 131 | +A*+T*+T*C*G*C*T*T*G*T*A*G*T*+C*+C*+G |
| 16 | A03016MR | 132 | +G*+A*T*T*C*G*C*T*T*G*T*A*G*T*+C*+C |
| 16 | A03017MR | 133 | +T*+G*+A*T*T*C*G*C*T*T*G*T*A*+G*+T*+C |
| 16 | A03018MR | 134 | +G*+T*+T*G*A*T*T*T*T*G*C*G*G*+T*+A*+T |
| 16 | A03019MR | 135 | +G*+G*+T*T*G*A*T*T*T*T*G*C*G*+G*+T*+A |
| 16 | A03020MR | 136 | +T*+G*+G*T*T*G*A*T*T*T*T*G*C*+G*+G*+T |
| 16 | A03021MR | 137 | +T*+G*+T*G*T*A*T*C*A*T*T*T*C*+G*+G*+T |
| 16 | A03022MR | 138 | +C*+T*+T*A*C*G*T*C*T*C*C*T*C*+G*+A*+A |
| 16 | A03023MR | 139 | +C*+A*+A*C*A*C*T*G*C*T*T*A*C*+G*+T*+C |
| 15 | A03024MR | 140 | +T*+T*+C*G*C*T*T*G*T*A*G*T*C*+C*+G |
| 15 | A03025MR | 141 | +G*A*+T*T*C*G*C*T*T*G*T*A*G*+T*+C |

TABLE 11-continued

List of mouse/rat antisense oligonucleotides:

| Length | Oligo Name | SEQ ID NO | Antisense Sequence 5'-3', partially with phosphorothioate linkages [*] and LNA modifications [+] |
|---|---|---|---|
| 15 | A03026MR | 142 | +T*+G*+A*T*T*C*G*C*T*T*G*T*+A*+G*+T |
| 15 | A03027MR | 143 | +T*+T*+A*C*G*T*C*T*C*C*T*C*+G*+A*+A |
| 15 | A03028MR | 144 | +C*+T*+T*A*C*G*T*C*T*C*C*T*+C*+G*+A |

TABLE 12

Relative expression of PD-L1 and HPRT1 in RENCA cells

| | Relative Expression [AU] | |
|---|---|---|
| | PD-L1 | HPRT1 |
| A03013MR | 0.01 | 1.09 |
| A03012MR | 0.06 | 0.98 |
| A03002MR | 0.07 | 1.23 |
| A03020MR | 0.09 | 1.13 |
| A03019MR | 0.10 | 1.35 |
| A03018MR | 0.12 | 1.26 |
| A03021MR | 0.17 | 1.28 |
| A03028MR | 0.20 | 1.32 |
| A03004MR | 0.21 | 0.88 |
| A030011MR | 0.27 | 1.22 |
| A03001MR | 0.27 | 1.13 |
| A03015MR | 0.28 | 1.27 |
| A03009MR | 0.28 | 1.11 |
| A03005MR | 0.29 | 1.14 |
| A03027MR | 0.33 | 1.22 |
| A03003MR | 0.35 | 1.03 |
| A03023MR | 0.37 | 1.45 |
| A03007MR | 0.42 | 1.13 |
| A03006MR | 0.42 | 1.17 |
| A03022MR | 0.42 | 1.56 |
| A03024MR | 0.44 | 1.25 |
| A03014MR | 0.45 | 1.19 |
| A03010MR | 0.46 | 1.27 |
| A03008MR | 0.70 | 0.95 |
| A03016MR | 1.03 | 1.03 |
| A03026MR | 1.08 | 1.47 |
| A03017MR | 1.12 | 1.15 |
| A03025MR | 1.23 | 1.40 |
| Neg. Ctrl. Oligo | 1.32 | 0.99 |

TABLE 13

Relative expression of PD-L1 and HPRT1 in 4T1 cells

| | Relative Expression [AU] | |
|---|---|---|
| | PD-L1 | HPRT1 |
| A03013MR | 0.06 | 0.88 |
| A03012MR | 0.07 | 1.31 |
| A03019MR | 0.07 | 3.89 |
| A03020MR | 0.08 | 3.59 |
| A03002MR | 0.09 | 0.98 |
| A03018MR | 0.09 | 2.10 |
| A03004MR | 0.10 | 1.53 |
| A03005MR | 0.16 | 1.59 |
| A03028MR | 0.17 | 3.54 |
| A03022MR | 0.19 | 2.10 |
| A03001MR | 0.22 | 1.43 |
| A03008MR | 0.22 | 1.88 |
| A030011MR | 0.23 | 1.72 |
| A03007MR | 0.25 | 2.17 |
| A03006MR | 0.25 | 1.88 |
| A03003MR | 0.29 | 2.02 |
| A03023MR | 0.29 | 2.75 |
| A03027MR | 0.30 | 1.99 |
| A03021MR | 0.32 | 3.24 |
| A03009MR | 0.37 | 1.57 |
| A03014MR | 0.37 | 1.73 |
| A03015MR | 0.39 | 1.46 |
| A03024MR | 0.43 | 1.63 |
| A03016MR | 0.46 | 1.72 |
| A03026MR | 0.62 | 2.41 |
| A03025MR | 0.70 | 2.77 |
| A03017MR | 0.81 | 1.55 |
| Neg Ctrl. Oligo | 0.82 | 1.79 |
| A03010MR | 1.40 | 1.65 |

Figure 8:
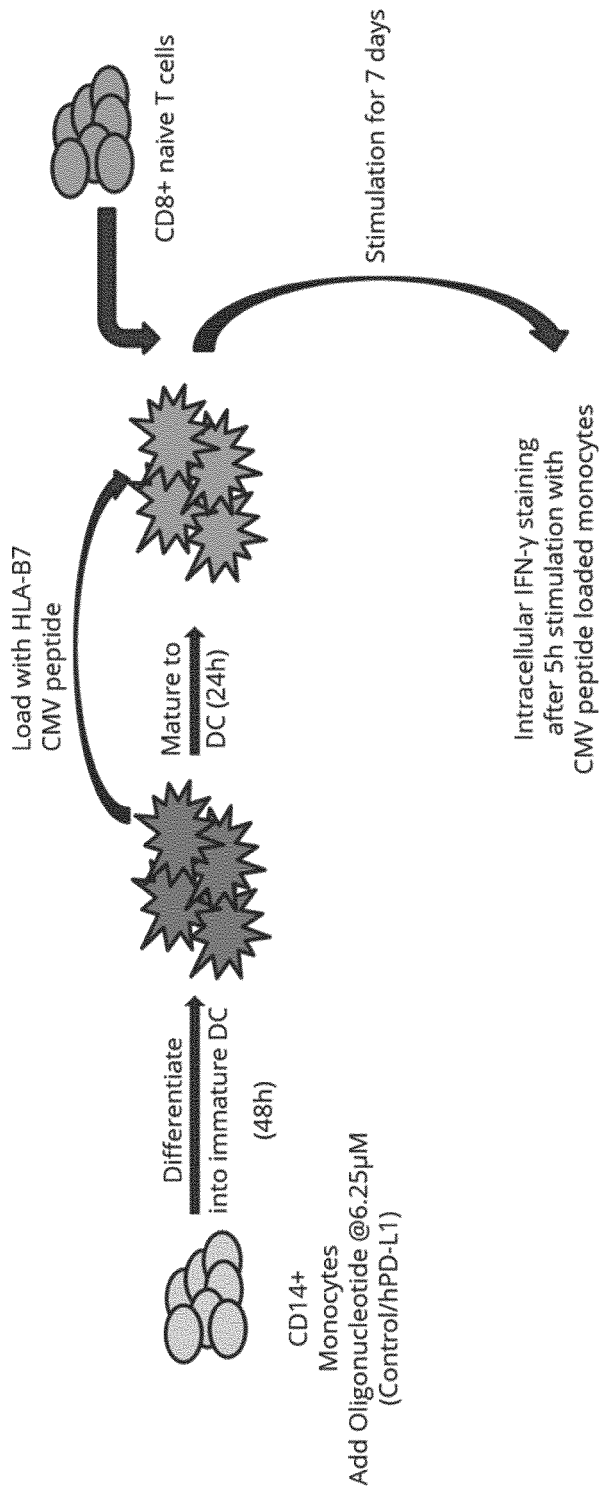
FIG. 8 shows that the antigen-specific stimulation of T cells with PD-L1 oligonucleotide-treated dendritic cells increases the frequency of antigen-specific T cells.

Example 6: Antigen-Specific Stimulation of T Cells with PD-L1 Oligonucleotide-Treated Dendritic Cells In order to investigate the effect of PD-L1 knockdown in dendritic cells (DC) on their priming capacity, we used a cytomegalovirus model-system (Experimental scheme: FIG. 8 A)).

Therefore, CD14+ monocytes of an HLA-B07 positive healthy blood donor were isolated out of peripheral blood mononuclear cells (PBMC) and differentiated into immature DC for 48 h in medium containing granulocyte-macrophage colony stimulating factor (GM-CSF, final concentration: 20 ng/ml) and interleukin-4 (IL-4, final concentration: 100 ng/ml). Maturation of DC was induced after 48 h by the addition of a cytokine cocktail consisting of:

| Cytokine/toll like receptor ligand | Final concentration |
|---|---|
| Tumor necrosis factor alpha (TNF-α) | 55 ng/ml |
| Interleukin-1 beta (IL-1β) | 2 ng/ml |
| Interferon gamma (IFN-γ) | 250 ng/ml |
| Prostaglandin E2 (PGE2) | 250 ng/ml |
| R848 | 1000 ng/ml |

DC were incubated for 24 h with the maturation cocktail and the HLA-B07-restricted CMV peptide "TPRVTGG-GAM" at a final concentration of 1 µM. Cells were either treated during the whole period with 6.25 µM of the control oligonucleotide S6 or the PD-L1 specific oligonucleotide A03014H) or left untreated.

Mature, CMV peptide loaded dendritic cells were harvested and co-cultured with nave CD8+ T cells from the same healthy donor for 7 days in medium containing interleukin-21 (IL-21, final concentration: 30 ng/ml), interleukin-7 (IL-7, final concentration: 5 ng/ml) and interleukin-15 (IL-15, final concentration: 5 ng/ml). To maintain knockdown of PD-L1 in DC during the co-culture, fresh oligonucleotide was added at a final concentration of 5 µM.

In order to measure the frequency of CMV peptide-specific T cells, T cells were harvested at the end of the priming period and co-incubated with CD14+ monocytes from the same donor that had been loaded with the CMV peptide "TPRVTGGGAM" at a concentration of 1 µM. After 1 hour, the golgi inhibitor brefeldin A was added to the co-culture and cells were incubated for an additional 4 h. Cells were stained with antibodies specific for the T cell markers CD3 and CD8 followed by intracellular staining with an IFN-γ specific antibody. Strikingly, as shown in FIG. 8 B), priming of nave T cells with CMV peptide-loaded, PD-L1 oligonucleotide-treated DC resulted in an over two-fold increase in the frequency of IFN-γ producing, CMV peptide-specific CD8+ T cells (mean frequency: 3.79%) as compared to untreated DC (mean frequency: 1.48%). Importantly, treatment of DC with the control oligonucleotide S6 had no influence on the frequency of CMV peptide-specific T cells (mean frequency: 1.84%).

Example 7: Knockdown of Human PD-L1 in Human Myeloid Derived Suppressor Cells (MDSC)

Figure 9:
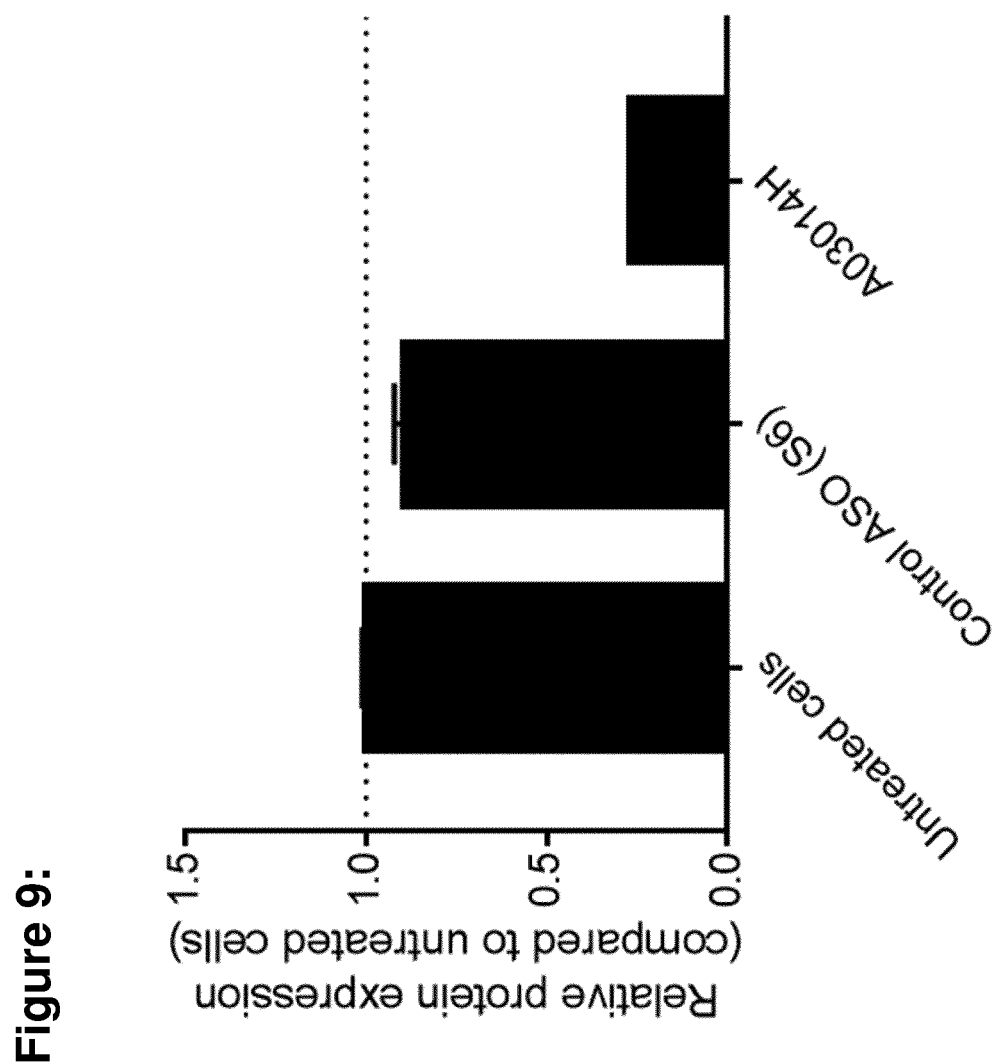
FIG. 9 shows the results of a knockdown of human PD-L1 in human myeloid derived suppressor cells (MDSC).

MDSC play an important role in the suppression of anti-tumor effector cells by the production of suppressive cytokines, suppressive enzymes but importantly also by direct interaction with effector cells, e.g. via the PD-1/PD-L1 axis. We therefore generated monocyte-derived MDSC in vitro. CD14 positive monocytes were isolated from human peripheral blood mononuclear cells (PBMC) and differentiated into MDSC by treatment with granulocyte-macrophage colony stimulating factor (GM-CSF, final concentration: 100 ng/ml), interleukin-4 (IL-4, final concentration: 200 ng/ml) and prostaglandin E2 (PGE2, final concentration: 1 µM) for seven days. Cells were treated during the differentiation period either with 2.5 OA of the control oligonucleotide S6 or the human PD-L1 specific oligonucleotide A03014H or left untreated. Cells were harvested and stained with a PD-L1 specific antibody and analyzed by flow cytometry. As shown in FIG. 9, treatment of MDSC with the PD-L1 specific oligonucleotide A03014H resulted in a suppression of PD-L1 protein expression by 83% compared to untreated cells. Importantly, the control oligonucleotide S6 had only a minimal influence on PD-L1 protein expression (10% suppression compared to untreated cells).

Example 8: Investigation of Effects of hPD-L1-Specific ASO on PD-L1 Protein Expression in Cancer Cells and Investigation of Persistence of Effects after Oligonucleotide Removal The antisense oligonucleotides A03014H, A03021 H, A03037H, A03043H, A03047H, and A03053H that were highly potent in reducing PD-L1 mRNA expression were further characterized in detail with regard to their knockdown efficacy on PD-L1 protein expression (FIG. 10, Table 14). Furthermore, the persistence of the effects after antisense oligonucleotide removal was examined. Therefore, HDLM-2 (Hodgkin lymphoma) cells were treated for a total treatment time of 3 days with 5 µM of selected PD-L1 specific antisense oligonucleotides or the control oligonucleotide neg 1, which is not complementary to any human mRNA. Thereafter, oligonucleotides were removed and hPD-L1 protein expression was analyzed 1, 2, 3, and 4 days after oligonucleotide removal by flow cytometry (FIG. 10, Table 14).

Strikingly, as depicted in FIG. 10 and Table 14, the oligonucleotides A03014H, A03021H, A03037H, A03043H, A03047H, and A03053H significantly suppressed hPD-L1 protein expression for a duration of at least four days after removal of antisense oligonucleotides, whereas treatment with neg 1 had no inhibitory effect on PD-L1 protein expression when compared to untreated control cells. (FIG. 10, Table 14).

In summary, these results show that suppression of PD-L1 protein expression continues even after oligonucleotide removal. Therefore, PD-L1 antisense oligonucleotides are suitable compounds for in vivo and ex vivo therapeutic applications.

TABLE 14

Protein knockdown efficiency of selected human PD-L1 antisense oligonucleotides in HDLM-2 cells

| | inhibition of PD-L1 protein expression [%] Time after ASO removal | | | | | | | | | |
|---|---|---|---|---|---|---|---|---|---|---|
| | D0 | | 24 h | | 48 h | | 72 h | | 96 h | |
| Compound ID | Mean | ±SD | Mean | ±SD | Mean | ±SD | Mean | ±SD | Mean | ±SD |
| A04014HM | 82.58 | 0.27 | 83.86 | 2.69 | 75.26 | 0.94 | 83.21 | 0.77 | 91.89 | 0.14 |
| A04021HM | 79.95 | 1.55 | 80.26 | 2.69 | 73.61 | 1.92 | 74.47 | 1.39 | 85.74 | 1.22 |
| A04037HM | 80.74 | 2.33 | 86.05 | 1.08 | 71.47 | 3.91 | 87.85 | 2.22 | 89.61 | 0.53 |
| A04043HM | 82.76 | 0.65 | 80.35 | 3.94 | 73.96 | 0.28 | 78.86 | 2.89 | 84.34 | 0.72 |
| A04047HM | 63.52 | 0.97 | 65.33 | 3.13 | 63.01 | 7.86 | 57.01 | 2.94 | 63.14 | 5.71 |
| A04053HM | 79.72 | 0.82 | 81.28 | 1.13 | 68.46 | 2.32 | 80.23 | 1.59 | 81.44 | 1.85 |
| neg1 | −0.72 | 1.57 | −8.18 | 3.19 | −0.03 | 0.08 | −7.40 | 0.62 | −7.10 | 1.51 |
| untreated control | 0.00 | 0.62 | 0.00 | 1.82 | 0.00 | 3.26 | 0.00 | 4.68 | 0.00 | 1.07 |

TABLE 15

| complete human PD-L1 mRNA sequence (NM_014143.3); SEQ ID No 115 |
| --- |
|    1 ggcgcaacgc tgagcagctg gcgcgtcccg cgcggcccca gttctgcgca gcttcccgag |
|   61 gctccgcacc agccgcgctt ctgtccgcct gcagggcatt ccagaaagat gaggatattt |
|  121 gctgtcttta tattcatgac ctactggcat ttgctgaacg catttactgt cacggttccc |
|  181 aaggacctat atgtggtaga gtatggtagc aatatgacaa ttgaatgcaa attcccagta |
|  241 gaaaaacaat agacctggc tgcactaatt gtctattggg aaatggagga taagaacatt |
|  301 attcaatttg tgcatggaga ggaagacctg aaggttcagc atagtagcta cagacagagg |
|  361 gcccggctgt tgaaggacca gctctccctg gaaatgctg cacttcagat cacagatgtg |
|  421 aaattgcagg atgcagggt gtaccgctgc atgatcagct atggtggtgc cgactacaag |
|  481 cgaattactg tgaaagtcaa tgcccccatac aacaaaatca ccaaagaat tttggttgtg |
|  541 gatccagtca cctctgaaca tgaactgaca tgtcaggctg agggctaccc caaggccgaa |
|  601 gtcatctgga caagcagtga ccatcaagtc ctgagtggta agaccaccac caccaattcc |
|  661 aagagagagg agaagctttt caatgtgacc agcacactga gaatcaacac aacaactaat |
|  721 gagatttcct actgcacttt taggagatta gatcctgagg aaaaccatac agctgaattg |
|  781 gtcatcccag aactacctct ggcacatcct ccaaatgaaa ggactcactt ggtaattctg |
|  841 ggagccatct tattatgcct tggtgtagca ctgacattca tcttccgttt aagaaaaggg |
|  901 agaatgatgg atgtgaaaaa atgtggcatc caagatacaa actcaaagaa gcaaagtgat |
|  961 acacatttgg aggagacgta atccagcatt ggaacttctg atcttcaagc agggattctc |
| 1021 aacctgtggt ttaggggttc atcggggctg agcgtgacaa gaggaaggaa tgggcccgtg |
| 1081 ggatgcaggc aatgtgggac ttaaaaggcc caagcactga aaatggaacc tggcgaaagc |
| 1141 agaggaggag aatgaagaaa gatggagtca acagggagc ctggagggag accttgatac |
| 1201 tttcaaatgc ctgaggggct catcgacgcc tgtgacaggg agaaaggata cttctgaaca |
| 1261 aggagcctcc aagcaaatca tccattgctc atcctaggaa gacgggttga gaatccctaa |
| 1321 tttgagggtc agttcctgca gaagtgccct tgcctccac tcaatgcctc aatttgtttt |
| 1381 ctgcatgact gagagtctca gtgttggaac gggacagtat tatgtatga gtttttccta |
| 1441 tttattttga gtctgtgagg tcttcttgtc atgtgagtgt ggttgtgaat gatttctttt |
| 1501 gaagatatat tgtagtagat gttacaattt gtcgccaaa ctaaacttgc tgcttaatga |
| 1561 tttgctcaca tctagtaaaa catggagtat ttgtaaggtg cttggtctcc tctataacta |
| 1621 caagtataca ttggaagcat aaagatcaaa ccgttggttg cataggatgt cacctttatt |
| 1681 taacccatta atactctggt tgacctaatc ttattctcag acctcaagtg tctgtgcagt |
| 1741 atctgttcca tttaaatatc agctttacaa ttatgtggta gcctacacac ataatctcat |
| 1801 ttcatcgctg taaccaccct gttgtgataa ccactattat tttacccatc gtacagctga |
| 1861 ggaagcaaac agattaagta acttgcccaa accagtaaat agcagacctc agactgccac |
| 1921 ccactgtcct tttataatac aatttacagc tatattttac tttaagcaat tcttttattc |
| 1981 aaaaaccatt tattaagtgc ccttgcaata tcaatcgctg tgccaggcat tgaatctaca |
| 2041 gatgtgagca agacaaagta cctgtcctca aggagctcat agtataatga ggagattaac |
| 2101 aagaaaatgt attattacaa tttagtccag tgtcatagca taaggatgat gcgaggggaa |
| 2161 aacccgagca gtgttgccaa gaggaggaaa taggccaatg tggtctggga cggttggata |
| 2221 tacttaaaca tcttaataat cagagtaatt ttcatttaca aagagaggtc ggtacttaaa |
| 2281 ataaccctga aaaataacac tggaattcct tttctagcat tatatttatt cctgatttgc |

TABLE 15-continued complete human PD-L1 mRNA sequence (NM_014143.3); SEQ ID No 115

```
2341 ctttgccata taatctaatg cttgtttata tagtgtctgg tattgtttaa cagttctgtc
2401 ttttctattt aaatgccact aaattttaaa ttcatacctt tccatgattc aaaattcaaa
2461 agatcccatg ggagatggtt ggaaaatctc cacttcatcc tccaagccat tcaagtttcc
2521 tttccagaag caactgctac tgcctttcat tcatatgttc ttctaaagat agtctacatt
2581 tggaaatgta tgttaaaagc acgtattttt aaaatttttt tcctaaatag taacacattg
2641 tatgtctgct gtgtactttg ctatttttat ttattttagt gtttcttata tagcagatgg
2701 aatgaatttg aagttcccag ggctgaggat ccatgccttc tttgtttcta agttatcttt
2761 cccatagctt ttcattatct ttcatatgat ccagtatatg ttaaatatgt cctacatata
2821 catttagaca accaccattt gttaagtatt tgctctagga cagagtttgg atttgtttat
2881 gtttgctcaa aaggagaccc atgggctctc cagggtgcac tgagtcaatc tagtcctaaa
2941 aagcaatctt attattaact ctgtatgaca gaatcatgtc tggaactttt gttttctgct
3001 ttctgtcaag tataaacttc actttgatgc tgtacttgca aaatcacatt ttctttctgg
3061 aaattccggc agtgtacctt gactgctagc taccctgtgc cagaaaagcc tcattcgttg
3121 tgcttgaacc cttgaatgcc accagctgtc atcactacac agccctccta agaggcttcc
3181 tggaggtttc gagattcaga tgccctggga gatcccagag tttcctttcc ctcttggcca
3241 tattctggtg tcaatgacaa ggagtacctt ggctttgcca catgtcaagg ctgaagaaac
3301 agtgtctcca acagagctcc ttgtgttatc tgtttgtaca tgtgcatttg tacagtaatt
3361 ggtgtgacag tgttctttgt gtgaattaca ggcaagaatt gtggctgagc aaggcacata
3421 gtctactcag tctattccta agtcctaact cctccttgtg gtgttggatt tgtaaggcac
3481 tttatccctt ttgtctcatg tttcatcgta aatggcatag gcagagatga tacctaattc
3541 tgcatttgat tgtcactttt tgtacctgca ttaatttaat aaaatattct tatttatttt
3601 gttacttggt acaccagcat gtccatttc ttgtttattt tgtgtttaat aaaatgttca
3661 gtttaacatc ccagtggaga aagttaaaaa a
```

TABLE 16 complete mRNA sequence of murine PD-L1 (CD274) sequence (NM_021893.3); SEQ ID No 116

```
  1 gaaatcgtgg tccccaagcc tcatgccagg ctgcacttgc acgtcgcggg ccagtctcct
 61 cgcctgcaga tagttcccaa aacatgagga tatttgctgg cattatattc acagcctgct
121 gtcacttgct acgggcgttt actatcacgg ctccaaagga cttgtacgtg gtggagtatg
181 gcagcaacgt cacgatggag tgcagattcc ctgtagaacg ggagctggac ctgcttgcgt
241 tagtggtgta ctgggaaaag gaagatgagc aagtgattca gtttgtggca ggagaggagg
301 accttaagcc tcagcacagc aacttcaggg ggagagcctc gctgccaaag gaccagcttt
361 tgaagggaaa tgctgcccct tcagatcacag acgtcaagct gcaggacgca ggcgtttact
421 gctgcataat cagctacggt ggtgcggact acaagcgaat cacgctgaaa gtcaatgccc
481 cataccgcaa aatcaaccag agaatttccg tggatccagc cacttctgag catgaactaa
541 tatgtcaggc cgagggttat ccagaagctg aggtaatctg acaaacagt gaccaccaac
601 ccgtgagtgg gaagagaagt gtcaccactt cccggacaga ggggatgctt ctcaatgtga
661 ccagcagtct gagggtcaac gccacagcga atgatgtttt ctactgtacg ttttggagat
```

TABLE 16-continued complete mRNA sequence of murine PD-L1 (CD274)
sequence (NM_021893.3); SEQ ID No 116

```
 721 cacagccagg gcaaaaccac acagcggagc tgatcatccc agaactgcct gcaacacatc
 781 ctccacagaa caggactcac tgggtgcttc tgggatccat cctgttgttc ctcattgtag
 841 tgtccacggt cctcctcttc ttgagaaaac aagtgagaat gctagatgtg gagaaatgtg
 901 gcgttgaaga tacaagctca aaaaaccgaa atgatacaca attcgaggag acgtaagcag
 961 tgttgaaccc tctgatcgtc gattggcagc ttgtggtctg tgaaagaaag ggcccatggg
1021 acatgagtcc aaagactcaa gatggaacct gagggagaga accaagaaag tgttgggaga
1081 ggagcctgga acaacggaca ttttttccag ggagacactg ctaagcaagt tgcccatcag
1141 tcgtcttggg aaatggattg agggttcctg gcttagcagc tggtccttgc acagtgacct
1201 tttcctctgc tcagtgccgg gatgagagat ggagtcatga gtgttgaaga ataagtgcct
1261 tctatttatt ttgagtctgt gtgttctcac tttgggcatg taattatgac tggtgaattc
1321 tgacgacatg atagatctta agatgtagtc accaaactca actgctgctt agcatcctcc
1381 gtaactactg atacaagcag ggaacacaga ggtcacctgc ttggtttgac aggctcttgc
1441 tgtctgactc aaataatctt tattttttcag tcctcaaggc tcttcgatag cagttgttct
1501 gtatcagcct tataggtgtc aggtatagca ctcaacatct catctcatta caatagcaac
1561 cctcatcacc atagcaacag ctaacctctg ttatcctcac ttcatagcca ggaagctgag
1621 cgactaagtc acttgcccac agagtatcag ctctcagatt tctgttcttc agccactgtc
1681 ctttcaggat agaatttgtc gttaagaaat taatttaaaa actgattatt gagtagcatt
1741 gtatatcaat cacaacatgc cttgtgcact gtgctggcct ctgagcataa agatgtacgc
1801 cggagtaccg gtcggacatg tttatgtgtg ttaaatactc agagaaatgt tcattaacaa
1861 ggagcttgca ttttagagac actggaaagt aactccagtt cattgtctag cattacattt
1921 acctcatttg ctatccttgc catacagtct cttgttctcc atgaagtgtc atgaatcttg
1981 ttgaatagtt cttttatttt ttaaatgttt ctatttaaat gatattgaca tctgaggcga
2041 tagctcagtt ggtaaaaccc tttcctcaca agtgtgaaac cctgagtctt atccctagaa
2101 cccacataaa aaacagttgc gtatgtttgt gcatgctttt gatcccagca ctagggaggc
2161 agaggcaggc agatcctgag ctctcattga ccacccagcc tagcctacat ggttagctcc
2221 aggcctacag gagctggcag agcctgaaaa acgatgccta gacacacaca cacacacaca
2281 cacacacaca cacacacaca caccatgt actcatagac ctaagtgcac cctcctacac
2341 atgcacacac atacaattca aacacaaatc aacagggaat tgtctcagaa tggtccccaa
2401 gacaagaag aagaaaaaca ccaaaccagc tctattccct cagcctatcc tctctactcc
2461 ttcctagaag caactactat tgtttttgta tataaattta cccaacgaca gttaatatgt
2521 agaatatata ttaaagtgtc tgtcaatata tattatctct ttctttcttt cttcctttct
2581 ttctttcttt ctttctttct ttctttcttt ctttctttct ttcttccttc cttccttcct
2641 tccttccttc cttccttcct ttctttcttt ctttctttt ttctgtctat ctgtacctaa
2701 atggttgctc actatgcatt ttctgtgctc ttcgcccttt ttatttaatg tatggatatt
2761 tatgctgctt ccagaatgga tctaaagctc tttgtttcta ggttttctcc cccatccttc
2821 taggcatctc tcacactgtc taggccagac accatgtctg ctgcctgaat ctgtagacac
2881 catttataaa gcacgtactc accgagtttg tatttggctt gttctgtgtc tgattaaagg
2941 gagaccatga gtccccaggg tacactgagt taccccagta ccaaggggga gccttgtttg
3001 tgtctccatg gcagaagcag gcctggagcc attttggttt cttccttgac ttctctcaaa
```

TABLE 16-continued complete mRNA sequence of murine PD-L1 (CD274)
sequence (NM_021893.3); SEQ ID No 116

```
3061 cacagacgcc tcacttgctc attacaggtt ctcctttggg aatgtcagca ttgctccttg 3121 actgctggct gccctggaag gagcccatta gctctgtgtg agcccttgac agctactgcc 3181 tctccttacc acaggggcct ctaagatact gttacctaga ggtcttgagg atctgtgttc 3241 tctgggggga ggaaggagg aggaacccag aactttctta cagttttcct tgttctgtca 3301 catgtcaaga ctgaaggaac aggctgggct acgtagtgag atcctgtctc aaaggaaaga 3361 cgagcatagc cgaaccccg gtggaacccc ctctgttacc tgttcacaca agcttattga 3421 tgagtctcat gttaatgtct tgtttgtatg aagtttaaga aaatatcggg ttgggcaaca 3481 cattctattt attcatttta tttgaaatct taatgccatc tcatggtgtt ggattggtgt 3541 ggcactttat tcttttgtgt tgtgtataac cataaatttt attttgcatc agattgtcaa 3601 tgtattgcat taatttaata aatattttta tttattaaaa aaaaaaaaa aaa
```

---

The invention claimed is:

1. An oligonucleotide consisting of 17 nucleotides, wherein the nucleobase sequence of the oligonucleotide is that of SEQ ID NO:107, wherein said oligonucleotide is a gapmer comprising at least one LNA nucleotide within the stretch of 5 nucleotides at the 5'-end of said oligonucleotide, and at least one LNA nucleotide within the stretch of 5 nucleotides at the 3'-end of said oligonucleotide.

2. A pharmaceutical composition comprising the oligonucleotide according to claim 1.

3. A method of treating a disease or disorder selected from the list of: a malignant tumor, and a benign tumor, the method comprising administering the oligonucleotide according to claim 1 to a subject in need thereof.

4. The method according to claim 3, wherein the tumor is selected from the group consisting of solid tumors, blood born tumors, leukemias, tumor metastasis, hemangiomas, acoustic neuromas, neurofibromas, trachomas, pyogenic granulomas, psoriasis, astrocytoma, acoustic neuroma, blastoma, Ewing's tumor, craniopharyngioma, ependymoma, medulloblastoma, glioma, hemangioblastoma, Hodgkin's lymphoma, medullablastoma, leukaemia, mesothelioma, neuroblastoma, neurofibroma, non-Hodgkin's lymphoma, pinealoma, retinoblastoma, sarcoma, seminoma, trachomas, and Wilms' tumor, or is selected from the group consisting of bile duct carcinoma, bladder carcinoma, brain tumor, breast cancer, bronchogenic carcinoma, carcinoma of the kidney, cervical cancer, choriocarcinoma, choroid carcinoma, cystadenocarcinoma, embryonal carcinoma, epithelial carcinoma, esophageal cancer, cervical carcinoma, colon carcinoma, colorectal carcinoma, endometrial cancer, gallbladder cancer, gastric cancer, head cancer, liver carcinoma, lung carcinoma, medullary carcinoma, neck cancer, non-small-cell bronchogenic/lung carcinoma, ovarian cancer, pancreas carcinoma, papillary carcinoma, papillary adenocarcinoma, prostate cancer, small intestine carcinoma, prostate carcinoma, rectal cancer, renal cell carcinoma, retinoblastoma, skin cancer, small-cell bronchogenic/lung carcinoma, squamous cell carcinoma, sebaceous gland carcinoma, testicular carcinoma, and uterine cancer.

5. The oligonucleotide of claim 1 comprising LNA modifications according to SEQ ID NO:108.

* * * * *

SEQUENCE LISTING

<160> NUMBER OF SEQ ID NOS: 146

<210> SEQ ID NO 1
<211> LENGTH: 13
<212> TYPE: DNA
<213> ORGANISM: Homo sapiens

<400> SEQUENCE: 1
ggattacgtc tcc                                                        13

<210> SEQ ID NO 2
<211> LENGTH: 13
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(1)
<223> OTHER INFORMATION: LNA_modification
<220> FEATURE:
<221> NAME/KEY: misc_feature
<222> LOCATION: (1)..(13)
<223> OTHER INFORMATION: phosphorothioate_linkages
<220> FEATURE:
<221> NAME/KEY: misc_feature
<222> LOCATION: (11)..(11)
<223> OTHER INFORMATION: LNA_modification
<220> FEATURE:
<221> NAME/KEY: misc_feature
<222> LOCATION: (13)..(13)
<223> OTHER INFORMATION: LNA_modification

<400> SEQUENCE: 2
ggattacgtc tcc                                                        13

<210> SEQ ID NO 3
<211> LENGTH: 13
<212> TYPE: DNA
<213> ORGANISM: Homo sapiens

<400> SEQUENCE: 3

```
tagtttggcg aca                                                          13

<210> SEQ ID NO 4
<211> LENGTH: 13
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(2)
<223> OTHER INFORMATION: LNA_modification
<220> FEATURE:
<221> NAME/KEY: misc_feature
<222> LOCATION: (1)..(13)
<223> OTHER INFORMATION: phosphorothioate_linkages
<220> FEATURE:
<221> NAME/KEY: misc_feature
<222> LOCATION: (11)..(13)
<223> OTHER INFORMATION: LNA_modification

<400> SEQUENCE: 4
tagtttggcg aca                                                          13

<210> SEQ ID NO 5
<211> LENGTH: 14
<212> TYPE: DNA
<213> ORGANISM: Homo sapiens

<400> SEQUENCE: 5
agaagcgcgg ctgg                                                         14

<210> SEQ ID NO 6
<211> LENGTH: 14
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(14)
<223> OTHER INFORMATION: phosphorothioate_linkages
<220> FEATURE:
<221> NAME/KEY: misc_feature
<222> LOCATION: (13)..(14)
<223> OTHER INFORMATION: LNA_modification

<400> SEQUENCE: 6
agaagcgcgg ctgg                                                         14

<210> SEQ ID NO 7
<211> LENGTH: 14
<212> TYPE: DNA
<213> ORGANISM: Homo sapiens

<400> SEQUENCE: 7
taccaagtga gtcc                                                         14

<210> SEQ ID NO 8
<211> LENGTH: 14
<212> TYPE: DNA
<213> ORGANISM: Artificial Sequence
```

```
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(14)
<223> OTHER INFORMATION: phosphorothioate_linkages
<220> FEATURE:
<221> NAME/KEY: misc_feature
<222> LOCATION: (13)..(14)
<223> OTHER INFORMATION: LNA_modification

<400> SEQUENCE: 8
taccaagtga gtcc                                                           14

<210> SEQ ID NO 9
<211> LENGTH: 14
<212> TYPE: DNA
<213> ORGANISM: Homo sapiens

<400> SEQUENCE: 9
gattacgtct cctc                                                           14

<210> SEQ ID NO 10
<211> LENGTH: 14
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(14)
<223> OTHER INFORMATION: phosphorothioate_linkages
<220> FEATURE:
<221> NAME/KEY: misc_feature
<222> LOCATION: (12)..(14)
<223> OTHER INFORMATION: LNA_modification

<400> SEQUENCE: 10
gattacgtct cctc                                                           14

<210> SEQ ID NO 11
<211> LENGTH: 14
<212> TYPE: DNA
<213> ORGANISM: Homo sapiens

<400> SEQUENCE: 11
ttcgccaggt tcca                                                           14

<210> SEQ ID NO 12
<211> LENGTH: 14
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
```

```
<223> OTHER INFORMATION: LNA_modification
<220> FEATURE:
<221> NAME/KEY: misc_feature
<222> LOCATION: (1)..(14)
<223> OTHER INFORMATION: phosphorothioate_linkages
<220> FEATURE:
<221> NAME/KEY: misc_feature
<222> LOCATION: (12)..(12)
<223> OTHER INFORMATION: LNA_modification
<220> FEATURE:
<221> NAME/KEY: misc_feature
<222> LOCATION: (14)..(14)
<223> OTHER INFORMATION: LNA_modification

<400> SEQUENCE: 12
ttcgccaggt tcca                                                      14

<210> SEQ ID NO 13
<211> LENGTH: 14
<212> TYPE: DNA
<213> ORGANISM: Homo sapiens

<400> SEQUENCE: 13
tttcgccagg ttcc                                                      14

<210> SEQ ID NO 14
<211> LENGTH: 14
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(14)
<223> OTHER INFORMATION: phosphorothioate_linkages
<220> FEATURE:
<221> NAME/KEY: misc_feature
<222> LOCATION: (12)..(12)
<223> OTHER INFORMATION: LNA_modification
<220> FEATURE:
<221> NAME/KEY: misc_feature
<222> LOCATION: (14)..(14)
<223> OTHER INFORMATION: LNA_modification

<400> SEQUENCE: 14
tttcgccagg ttcc                                                      14

<210> SEQ ID NO 15
<211> LENGTH: 14
<212> TYPE: DNA
<213> ORGANISM: Homo sapiens

<400> SEQUENCE: 15
ttagtttggc gaca                                                      14

<210> SEQ ID NO 16
<211> LENGTH: 14
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
```

```
<222> LOCATION: (1)..(3)
<223> OTHER INFORMATION: LNA_modification
<220> FEATURE:
<221> NAME/KEY: misc_feature
<222> LOCATION: (1)..(14)
<223> OTHER INFORMATION: phosphorothioate_linkages
<220> FEATURE:
<221> NAME/KEY: misc_feature
<222> LOCATION: (12)..(14)
<223> OTHER INFORMATION: LNA_modification

<400> SEQUENCE: 16
ttagtttggc gaca                                                         14

<210> SEQ ID NO 17
<211> LENGTH: 14
<212> TYPE: DNA
<213> ORGANISM: Homo sapiens

<400> SEQUENCE: 17
gtggttacag cgat                                                         14

<210> SEQ ID NO 18
<211> LENGTH: 14
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(14)
<223> OTHER INFORMATION: phosphorothioate_linkages
<220> FEATURE:
<221> NAME/KEY: misc_feature
<222> LOCATION: (12)..(14)
<223> OTHER INFORMATION: LNA_modification

<400> SEQUENCE: 18
gtggttacag cgat                                                         14

<210> SEQ ID NO 19
<211> LENGTH: 14
<212> TYPE: DNA
<213> ORGANISM: Homo sapiens

<400> SEQUENCE: 19
aggactagat tgac                                                         14

<210> SEQ ID NO 20
<211> LENGTH: 14
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(14)
<223> OTHER INFORMATION: phosphorothioate_linkages
<220> FEATURE:
```

```
<221> NAME/KEY: misc_feature
<222> LOCATION: (12)..(14)
<223> OTHER INFORMATION: LNA_modification

<400> SEQUENCE: 20
aggactagat tgac                                                   14

<210> SEQ ID NO 21
<211> LENGTH: 14
<212> TYPE: DNA
<213> ORGANISM: Homo sapiens

<400> SEQUENCE: 21
tcaagcacaa cgaa                                                   14

<210> SEQ ID NO 22
<211> LENGTH: 14
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(14)
<223> OTHER INFORMATION: phosphorothioate_linkages
<220> FEATURE:
<221> NAME/KEY: misc_feature
<222> LOCATION: (12)..(14)
<223> OTHER INFORMATION: LNA_modification

<400> SEQUENCE: 22
tcaagcacaa cgaa                                                   14

<210> SEQ ID NO 23
<211> LENGTH: 14
<212> TYPE: DNA
<213> ORGANISM: Homo sapiens

<400> SEQUENCE: 23
gagtagacta tgtg                                                   14

<210> SEQ ID NO 24
<211> LENGTH: 14
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(14)
<223> OTHER INFORMATION: phosphorothioate_linkages
<220> FEATURE:
<221> NAME/KEY: misc_feature
<222> LOCATION: (12)..(14)
<223> OTHER INFORMATION: LNA_modification

<400> SEQUENCE: 24
gagtagacta tgtg                                                   14
```

```
<210> SEQ ID NO 25
<211> LENGTH: 15
<212> TYPE: DNA
<213> ORGANISM: Homo sapiens

<400> SEQUENCE: 25
tggtgcggag cctcg                                                    15

<210> SEQ ID NO 26
<211> LENGTH: 15
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(1)
<223> OTHER INFORMATION: LNA_modification
<220> FEATURE:
<221> NAME/KEY: misc_feature
<222> LOCATION: (1)..(15)
<223> OTHER INFORMATION: phosphorothioate_linkages
<220> FEATURE:
<221> NAME/KEY: misc_feature
<222> LOCATION: (3)..(3)
<223> OTHER INFORMATION: LNA_modification
<220> FEATURE:
<221> NAME/KEY: misc_feature
<222> LOCATION: (13)..(13)
<223> OTHER INFORMATION: LNA_modification
<220> FEATURE:
<221> NAME/KEY: misc_feature
<222> LOCATION: (15)..(15)
<223> OTHER INFORMATION: LNA_modification

<400> SEQUENCE: 26
tggtgcggag cctcg                                                    15

<210> SEQ ID NO 27
<211> LENGTH: 15
<212> TYPE: DNA
<213> ORGANISM: Homo sapiens

<400> SEQUENCE: 27
gttgtgttga ttctc                                                    15

<210> SEQ ID NO 28
<211> LENGTH: 15
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(15)
<223> OTHER INFORMATION: phosphorothioate_linkages
<220> FEATURE:
<221> NAME/KEY: misc_feature
<222> LOCATION: (13)..(15)
<223> OTHER INFORMATION: LNA_modification

<400> SEQUENCE: 28
```

```
gttgtgttga ttctc                                                      15
```

<210> SEQ ID NO 29
<211> LENGTH: 15
<212> TYPE: DNA
<213> ORGANISM: Homo sapiens

<400> SEQUENCE: 29

```
gaccaattca gctgt                                                      15
```

<210> SEQ ID NO 30
<211> LENGTH: 15
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(15)
<223> OTHER INFORMATION: phosphorothioate_linkages
<220> FEATURE:
<221> NAME/KEY: misc_feature
<222> LOCATION: (13)..(15)
<223> OTHER INFORMATION: LNA_modification

<400> SEQUENCE: 30

```
gaccaattca gctgt                                                      15
```

<210> SEQ ID NO 31
<211> LENGTH: 15
<212> TYPE: DNA
<213> ORGANISM: Homo sapiens

<400> SEQUENCE: 31

```
ttaccaagtg agtcc                                                      15
```

<210> SEQ ID NO 32
<211> LENGTH: 15
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(15)
<223> OTHER INFORMATION: phosphorothioate_linkages
<220> FEATURE:
<221> NAME/KEY: misc_feature
<222> LOCATION: (13)..(15)
<223> OTHER INFORMATION: LNA_modification

<400> SEQUENCE: 32

```
ttaccaagtg agtcc                                                      15
```

<210> SEQ ID NO 33
<211> LENGTH: 15
<212> TYPE: DNA
<213> ORGANISM: Homo sapiens

```
<400> SEQUENCE: 33
tgtcagtgct acacc                                                        15

<210> SEQ ID NO 34
<211> LENGTH: 15
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(1)
<223> OTHER INFORMATION: LNA_modification
<220> FEATURE:
<221> NAME/KEY: misc_feature
<222> LOCATION: (1)..(15)
<223> OTHER INFORMATION: phosphorothioate_linkages
<220> FEATURE:
<221> NAME/KEY: misc_feature
<222> LOCATION: (3)..(3)
<223> OTHER INFORMATION: LNA_modification
<220> FEATURE:
<221> NAME/KEY: misc_feature
<222> LOCATION: (13)..(13)
<223> OTHER INFORMATION: LNA_modification
<220> FEATURE:
<221> NAME/KEY: misc_feature
<222> LOCATION: (15)..(15)
<223> OTHER INFORMATION: LNA_modification

<400> SEQUENCE: 34
tgtcagtgct acacc                                                        15

<210> SEQ ID NO 35
<211> LENGTH: 15
<212> TYPE: DNA
<213> ORGANISM: Homo sapiens

<400> SEQUENCE: 35
attacgtctc ctcca                                                        15

<210> SEQ ID NO 36
<211> LENGTH: 15
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(15)
<223> OTHER INFORMATION: phosphorothioate_linkages
<220> FEATURE:
<221> NAME/KEY: misc_feature
<222> LOCATION: (13)..(15)
<223> OTHER INFORMATION: LNA_modification

<400> SEQUENCE: 36
attacgtctc ctcca                                                        15

<210> SEQ ID NO 37
<211> LENGTH: 15
<212> TYPE: DNA
```

<213> ORGANISM: Homo sapiens

<400> SEQUENCE: 37
tcgccaggtt ccatt                                                    15

<210> SEQ ID NO 38
<211> LENGTH: 15
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(15)
<223> OTHER INFORMATION: phosphorothioate_linkages
<220> FEATURE:
<221> NAME/KEY: misc_feature
<222> LOCATION: (13)..(15)
<223> OTHER INFORMATION: LNA_modification

<400> SEQUENCE: 38
tcgccaggtt ccatt                                                    15

<210> SEQ ID NO 39
<211> LENGTH: 15
<212> TYPE: DNA
<213> ORGANISM: Homo sapiens

<400> SEQUENCE: 39
ggattctcaa cccgt                                                    15

<210> SEQ ID NO 40
<211> LENGTH: 15
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(1)
<223> OTHER INFORMATION: LNA_modification
<220> FEATURE:
<221> NAME/KEY: misc_feature
<222> LOCATION: (1)..(15)
<223> OTHER INFORMATION: phosphorothioate_linkages
<220> FEATURE:
<221> NAME/KEY: misc_feature
<222> LOCATION: (13)..(15)
<223> OTHER INFORMATION: LNA_modification

<400> SEQUENCE: 40
ggattctcaa cccgt                                                    15

<210> SEQ ID NO 41
<211> LENGTH: 15
<212> TYPE: DNA
<213> ORGANISM: Homo sapiens

<400> SEQUENCE: 41
tttagtttgg cgaca                                                    15

```
<210> SEQ ID NO 42
<211> LENGTH: 15
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(15)
<223> OTHER INFORMATION: phosphorothioate_linkages
<220> FEATURE:
<221> NAME/KEY: misc_feature
<222> LOCATION: (13)..(15)
<223> OTHER INFORMATION: LNA_modification

<400> SEQUENCE: 42
tttagtttgg cgaca                                                  15

<210> SEQ ID NO 43
<211> LENGTH: 15
<212> TYPE: DNA
<213> ORGANISM: Homo sapiens

<400> SEQUENCE: 43
agttatagag gagac                                                  15

<210> SEQ ID NO 44
<211> LENGTH: 15
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(15)
<223> OTHER INFORMATION: phosphorothioate_linkages
<220> FEATURE:
<221> NAME/KEY: misc_feature
<222> LOCATION: (13)..(15)
<223> OTHER INFORMATION: LNA_modification

<400> SEQUENCE: 44
agttatagag gagac                                                  15

<210> SEQ ID NO 45
<211> LENGTH: 15
<212> TYPE: DNA
<213> ORGANISM: Homo sapiens

<400> SEQUENCE: 45
ggtggttaca gcgat                                                  15

<210> SEQ ID NO 46
<211> LENGTH: 15
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
```

```
        Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(15)
<223> OTHER INFORMATION: phosphorothioate_linkages
<220> FEATURE:
<221> NAME/KEY: misc_feature
<222> LOCATION: (13)..(15)
<223> OTHER INFORMATION: LNA_modification

<400> SEQUENCE: 46
ggtggttaca gcgat                                                        15

<210> SEQ ID NO 47
<211> LENGTH: 15
<212> TYPE: DNA
<213> ORGANISM: Homo sapiens

<400> SEQUENCE: 47
ccttatgcta tgaca                                                        15

<210> SEQ ID NO 48
<211> LENGTH: 15
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(15)
<223> OTHER INFORMATION: phosphorothioate_linkages
<220> FEATURE:
<221> NAME/KEY: misc_feature
<222> LOCATION: (13)..(15)
<223> OTHER INFORMATION: LNA_modification

<400> SEQUENCE: 48
ccttatgcta tgaca                                                        15

<210> SEQ ID NO 49
<211> LENGTH: 15
<212> TYPE: DNA
<213> ORGANISM: Homo sapiens

<400> SEQUENCE: 49
ggactagatt gactc                                                        15

<210> SEQ ID NO 50
<211> LENGTH: 15
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(1)
<223> OTHER INFORMATION: LNA_modification
<220> FEATURE:
<221> NAME/KEY: misc_feature
```

```
<222> LOCATION: (1)..(15)
<223> OTHER INFORMATION: phosphorothioate_linkages
<220> FEATURE:
<221> NAME/KEY: misc_feature
<222> LOCATION: (3)..(3)
<223> OTHER INFORMATION: LNA_modification
<220> FEATURE:
<221> NAME/KEY: misc_feature
<222> LOCATION: (13)..(15)
<223> OTHER INFORMATION: LNA_modification

<400> SEQUENCE: 50
ggactagatt gactc                                                     15

<210> SEQ ID NO 51
<211> LENGTH: 15
<212> TYPE: DNA
<213> ORGANISM: Homo sapiens

<400> SEQUENCE: 51
tagcagtcaa ggtac                                                     15

<210> SEQ ID NO 52
<211> LENGTH: 15
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(15)
<223> OTHER INFORMATION: phosphorothioate_linkages
<220> FEATURE:
<221> NAME/KEY: misc_feature
<222> LOCATION: (13)..(15)
<223> OTHER INFORMATION: LNA_modification

<400> SEQUENCE: 52
tagcagtcaa ggtac                                                     15

<210> SEQ ID NO 53
<211> LENGTH: 15
<212> TYPE: DNA
<213> ORGANISM: Homo sapiens

<400> SEQUENCE: 53
cgaatgaggc ttttc                                                     15

<210> SEQ ID NO 54
<211> LENGTH: 15
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(1)
<223> OTHER INFORMATION: LNA_modification
<220> FEATURE:
<221> NAME/KEY: misc_feature
<222> LOCATION: (1)..(15)
<223> OTHER INFORMATION: phosphorothioate_linkages
<220> FEATURE:
```

```
<221> NAME/KEY: misc_feature
<222> LOCATION: (3)..(3)
<223> OTHER INFORMATION: LNA_modification
<220> FEATURE:
<221> NAME/KEY: misc_feature
<222> LOCATION: (13)..(15)
<223> OTHER INFORMATION: LNA_modification

<400> SEQUENCE: 54
cgaatgaggc ttttc                                                  15

<210> SEQ ID NO 55
<211> LENGTH: 15
<212> TYPE: DNA
<213> ORGANISM: Homo sapiens

<400> SEQUENCE: 55
ctgtgtagtg atgac                                                  15

<210> SEQ ID NO 56
<211> LENGTH: 15
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(15)
<223> OTHER INFORMATION: phosphorothioate_linkages
<220> FEATURE:
<221> NAME/KEY: misc_feature
<222> LOCATION: (13)..(15)
<223> OTHER INFORMATION: LNA_modification

<400> SEQUENCE: 56
ctgtgtagtg atgac                                                  15

<210> SEQ ID NO 57
<211> LENGTH: 15
<212> TYPE: DNA
<213> ORGANISM: Homo sapiens

<400> SEQUENCE: 57
gactatgtgc cttgc                                                  15

<210> SEQ ID NO 58
<211> LENGTH: 15
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(15)
<223> OTHER INFORMATION: phosphorothioate_linkages
<220> FEATURE:
<221> NAME/KEY: misc_feature
<222> LOCATION: (13)..(15)
<223> OTHER INFORMATION: LNA_modification
```

<400> SEQUENCE: 58
gactatgtgc cttgc                                                    15

<210> SEQ ID NO 59
<211> LENGTH: 15
<212> TYPE: DNA
<213> ORGANISM: Homo sapiens

<400> SEQUENCE: 59
gataaagtgc cttac                                                    15

<210> SEQ ID NO 60
<211> LENGTH: 15
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(15)
<223> OTHER INFORMATION: phosphorothioate_linkages
<220> FEATURE:
<221> NAME/KEY: misc_feature
<222> LOCATION: (13)..(15)
<223> OTHER INFORMATION: LNA_modification

<400> SEQUENCE: 60
gataaagtgc cttac                                                    15

<210> SEQ ID NO 61
<211> LENGTH: 15
<212> TYPE: DNA
<213> ORGANISM: Homo sapiens

<400> SEQUENCE: 61
cctatgccat ttacg                                                    15

<210> SEQ ID NO 62
<211> LENGTH: 15
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(15)
<223> OTHER INFORMATION: phosphorothioate_linkages
<220> FEATURE:
<221> NAME/KEY: misc_feature
<222> LOCATION: (13)..(15)
<223> OTHER INFORMATION: LNA_modification

<400> SEQUENCE: 62
cctatgccat ttacg                                                    15

<210> SEQ ID NO 63

```
<211> LENGTH: 16
<212> TYPE: DNA
<213> ORGANISM: Homo sapiens

<400> SEQUENCE: 63
agaagcgcgg ctggtg                                                   16

<210> SEQ ID NO 64
<211> LENGTH: 16
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(16)
<223> OTHER INFORMATION: phosphorothioate_linkages
<220> FEATURE:
<221> NAME/KEY: misc_feature
<222> LOCATION: (14)..(16)
<223> OTHER INFORMATION: LNA_modification

<400> SEQUENCE: 64
agaagcgcgg ctggtg                                                   16

<210> SEQ ID NO 65
<211> LENGTH: 16
<212> TYPE: DNA
<213> ORGANISM: Homo sapiens

<400> SEQUENCE: 65
tcaggacttg atggtc                                                   16

<210> SEQ ID NO 66
<211> LENGTH: 16
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(1)
<223> OTHER INFORMATION: LNA_modification
<220> FEATURE:
<221> NAME/KEY: misc_feature
<222> LOCATION: (1)..(16)
<223> OTHER INFORMATION: phosphorothioate_linkages
<220> FEATURE:
<221> NAME/KEY: misc_feature
<222> LOCATION: (3)..(3)
<223> OTHER INFORMATION: LNA_modification
<220> FEATURE:
<221> NAME/KEY: misc_feature
<222> LOCATION: (14)..(16)
<223> OTHER INFORMATION: LNA_modification

<400> SEQUENCE: 66
tcaggacttg atggtc                                                   16

<210> SEQ ID NO 67
<211> LENGTH: 16
<212> TYPE: DNA
<213> ORGANISM: Homo sapiens
```

-continued

<400> SEQUENCE: 67
ctctcttgga attggt                                                         16

<210> SEQ ID NO 68
<211> LENGTH: 16
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(16)
<223> OTHER INFORMATION: phosphorothioate_linkages
<220> FEATURE:
<221> NAME/KEY: misc_feature
<222> LOCATION: (14)..(16)
<223> OTHER INFORMATION: LNA_modification

<400> SEQUENCE: 68
ctctcttgga attggt                                                         16

<210> SEQ ID NO 69
<211> LENGTH: 16
<212> TYPE: DNA
<213> ORGANISM: Homo sapiens

<400> SEQUENCE: 69
gaccaattca gctgta                                                         16

<210> SEQ ID NO 70
<211> LENGTH: 16
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(16)
<223> OTHER INFORMATION: phosphorothioate_linkages
<220> FEATURE:
<221> NAME/KEY: misc_feature
<222> LOCATION: (14)..(16)
<223> OTHER INFORMATION: LNA_modification

<400> SEQUENCE: 70
gaccaattca gctgta                                                         16

<210> SEQ ID NO 71
<211> LENGTH: 16
<212> TYPE: DNA
<213> ORGANISM: Homo sapiens

<400> SEQUENCE: 71
ttaccaagtg agtcct                                                         16

<210> SEQ ID NO 72

```
<211> LENGTH: 16
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(16)
<223> OTHER INFORMATION: phosphorothioate_linkages
<220> FEATURE:
<221> NAME/KEY: misc_feature
<222> LOCATION: (14)..(16)
<223> OTHER INFORMATION: LNA_modification

<400> SEQUENCE: 72
ttaccaagtg agtcct                                                   16

<210> SEQ ID NO 73
<211> LENGTH: 16
<212> TYPE: DNA
<213> ORGANISM: Homo sapiens

<400> SEQUENCE: 73
tgtcagtgct acacca                                                   16

<210> SEQ ID NO 74
<211> LENGTH: 16
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(16)
<223> OTHER INFORMATION: phosphorothioate_linkages
<220> FEATURE:
<221> NAME/KEY: misc_feature
<222> LOCATION: (14)..(16)
<223> OTHER INFORMATION: LNA_modification

<400> SEQUENCE: 74
tgtcagtgct acacca                                                   16

<210> SEQ ID NO 75
<211> LENGTH: 16
<212> TYPE: DNA
<213> ORGANISM: Homo sapiens

<400> SEQUENCE: 75
aatgctggat tacgtc                                                   16

<210> SEQ ID NO 76
<211> LENGTH: 16
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
```

```
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(16)
<223> OTHER INFORMATION: phosphorothioate_linkages
<220> FEATURE:
<221> NAME/KEY: misc_feature
<222> LOCATION: (14)..(16)
<223> OTHER INFORMATION: LNA_modification

<400> SEQUENCE: 76
aatgctggat tacgtc                                                    16

<210> SEQ ID NO 77
<211> LENGTH: 16
<212> TYPE: DNA
<213> ORGANISM: Homo sapiens

<400> SEQUENCE: 77
ttcgccaggt tccatt                                                    16

<210> SEQ ID NO 78
<211> LENGTH: 16
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(2)
<223> OTHER INFORMATION: LNA_modification
<220> FEATURE:
<221> NAME/KEY: misc_feature
<222> LOCATION: (1)..(16)
<223> OTHER INFORMATION: phosphorothioate_linkages
<220> FEATURE:
<221> NAME/KEY: misc_feature
<222> LOCATION: (14)..(16)
<223> OTHER INFORMATION: LNA_modification

<400> SEQUENCE: 78
ttcgccaggt tccatt                                                    16

<210> SEQ ID NO 79
<211> LENGTH: 16
<212> TYPE: DNA
<213> ORGANISM: Homo sapiens

<400> SEQUENCE: 79
gctttcgcca ggttcc                                                    16

<210> SEQ ID NO 80
<211> LENGTH: 16
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(16)
```

```
<223> OTHER INFORMATION: phosphorothioate_linkages
<220> FEATURE:
<221> NAME/KEY: misc_feature
<222> LOCATION: (14)..(16)
<223> OTHER INFORMATION: LNA_modification

<400> SEQUENCE: 80
gctttcgcca ggttcc                                                    16

<210> SEQ ID NO 81
<211> LENGTH: 16
<212> TYPE: DNA
<213> ORGANISM: Homo sapiens

<400> SEQUENCE: 81
agtatcaagg tctccc                                                    16

<210> SEQ ID NO 82
<211> LENGTH: 16
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(16)
<223> OTHER INFORMATION: phosphorothioate_linkages
<220> FEATURE:
<221> NAME/KEY: misc_feature
<222> LOCATION: (14)..(16)
<223> OTHER INFORMATION: LNA_modification

<400> SEQUENCE: 82
agtatcaagg tctccc                                                    16

<210> SEQ ID NO 83
<211> LENGTH: 16
<212> TYPE: DNA
<213> ORGANISM: Homo sapiens

<400> SEQUENCE: 83
agttatagag gagacc                                                    16

<210> SEQ ID NO 84
<211> LENGTH: 16
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(16)
<223> OTHER INFORMATION: phosphorothioate_linkages
<220> FEATURE:
<221> NAME/KEY: misc_feature
<222> LOCATION: (14)..(16)
<223> OTHER INFORMATION: LNA_modification

<400> SEQUENCE: 84
```
agttatagag gagacc    16

<210> SEQ ID NO 85
<211> LENGTH: 16
<212> TYPE: DNA
<213> ORGANISM: Homo sapiens

<400> SEQUENCE: 85
gtggttacag cgatga    16

<210> SEQ ID NO 86
<211> LENGTH: 16
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(2)
<223> OTHER INFORMATION: LNA_modification
<220> FEATURE:
<221> NAME/KEY: misc_feature
<222> LOCATION: (1)..(16)
<223> OTHER INFORMATION: phosphorothioate_linkages
<220> FEATURE:
<221> NAME/KEY: misc_feature
<222> LOCATION: (14)..(16)
<223> OTHER INFORMATION: LNA_modification

<400> SEQUENCE: 86
gtggttacag cgatga    16

<210> SEQ ID NO 87
<211> LENGTH: 16
<212> TYPE: DNA
<213> ORGANISM: Homo sapiens

<400> SEQUENCE: 87
gattgactca gtgcac    16

<210> SEQ ID NO 88
<211> LENGTH: 16
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(16)
<223> OTHER INFORMATION: phosphorothioate_linkages
<220> FEATURE:
<221> NAME/KEY: misc_feature
<222> LOCATION: (15)..(16)
<223> OTHER INFORMATION: LNA_modification

<400> SEQUENCE: 88
gattgactca gtgcac    16

<210> SEQ ID NO 89
<211> LENGTH: 16
<212> TYPE: DNA

<213> ORGANISM: Homo sapiens

<400> SEQUENCE: 89
tagcagtcaa ggtaca                                                    16

<210> SEQ ID NO 90
<211> LENGTH: 16
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(16)
<223> OTHER INFORMATION: phosphorothioate_linkages
<220> FEATURE:
<221> NAME/KEY: misc_feature
<222> LOCATION: (14)..(16)
<223> OTHER INFORMATION: LNA_modification

<400> SEQUENCE: 90
tagcagtcaa ggtaca                                                    16

<210> SEQ ID NO 91
<211> LENGTH: 16
<212> TYPE: DNA
<213> ORGANISM: Homo sapiens

<400> SEQUENCE: 91
gttcaagcac aacgaa                                                    16

<210> SEQ ID NO 92
<211> LENGTH: 16
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(16)
<223> OTHER INFORMATION: phosphorothioate_linkages
<220> FEATURE:
<221> NAME/KEY: misc_feature
<222> LOCATION: (14)..(16)
<223> OTHER INFORMATION: LNA_modification

<400> SEQUENCE: 92
gttcaagcac aacgaa                                                    16

<210> SEQ ID NO 93
<211> LENGTH: 16
<212> TYPE: DNA
<213> ORGANISM: Homo sapiens

<400> SEQUENCE: 93
gcctatgcca tttacg                                                    16

```
<210> SEQ ID NO 94
<211> LENGTH: 16
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(16)
<223> OTHER INFORMATION: phosphorothioate_linkages
<220> FEATURE:
<221> NAME/KEY: misc_feature
<222> LOCATION: (14)..(16)
<223> OTHER INFORMATION: LNA_modification

<400> SEQUENCE: 94
gcctatgcca tttacg                                               16

<210> SEQ ID NO 95
<211> LENGTH: 17
<212> TYPE: DNA
<213> ORGANISM: Homo sapiens

<400> SEQUENCE: 95
agaagcgcgg ctggtgc                                              17

<210> SEQ ID NO 96
<211> LENGTH: 17
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(17)
<223> OTHER INFORMATION: phosphorothioate_linkages
<220> FEATURE:
<221> NAME/KEY: misc_feature
<222> LOCATION: (15)..(15)
<223> OTHER INFORMATION: LNA_modification
<220> FEATURE:
<221> NAME/KEY: misc_feature
<222> LOCATION: (17)..(17)
<223> OTHER INFORMATION: LNA_modification

<400> SEQUENCE: 96
agaagcgcgg ctggtgc                                              17

<210> SEQ ID NO 97
<211> LENGTH: 17
<212> TYPE: DNA
<213> ORGANISM: Homo sapiens

<400> SEQUENCE: 97
accaattcag ctgtatg                                              17

<210> SEQ ID NO 98
<211> LENGTH: 17
<212> TYPE: DNA
```

```
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(17)
<223> OTHER INFORMATION: phosphorothioate_linkages
<220> FEATURE:
<221> NAME/KEY: misc_feature
<222> LOCATION: (15)..(15)
<223> OTHER INFORMATION: LNA_modification
<220> FEATURE:
<221> NAME/KEY: misc_feature
<222> LOCATION: (17)..(17)
<223> OTHER INFORMATION: LNA_modification

<400> SEQUENCE: 98
accaattcag ctgtatg                                                    17

<210> SEQ ID NO 99
<211> LENGTH: 17
<212> TYPE: DNA
<213> ORGANISM: Homo sapiens

<400> SEQUENCE: 99
tgctggatta cgtctcc                                                    17

<210> SEQ ID NO 100
<211> LENGTH: 17
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(17)
<223> OTHER INFORMATION: phosphorothioate_linkages
<220> FEATURE:
<221> NAME/KEY: misc_feature
<222> LOCATION: (15)..(17)
<223> OTHER INFORMATION: LNA_modification

<400> SEQUENCE: 100
tgctggatta cgtctcc                                                    17

<210> SEQ ID NO 101
<211> LENGTH: 17
<212> TYPE: DNA
<213> ORGANISM: Homo sapiens

<400> SEQUENCE: 101
tttcgccagg ttccatt                                                    17

<210> SEQ ID NO 102
<211> LENGTH: 17
<212> TYPE: DNA
<213> ORGANISM: Artificial Sequence
<220> FEATURE:
<223> OTHER INFORMATION: antisense_sequence_5'-3'_partially_with_
```

```
                                                                -continued phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(17)
<223> OTHER INFORMATION: phosphorothioate_linkages
<220> FEATURE:
<221> NAME/KEY: misc_feature
<222> LOCATION: (15)..(17)
<223> OTHER INFORMATION: LNA_modification

<400> SEQUENCE: 102
tttcgccagg ttccatt                                                  17

<210> SEQ ID NO 103
<211> LENGTH: 17
<212> TYPE: DNA
<213> ORGANISM: Homo sapiens

<400> SEQUENCE: 103
gtatcaaggt ctccctc                                                  17

<210> SEQ ID NO 104
<211> LENGTH: 17
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(17)
<223> OTHER INFORMATION: phosphorothioate_linkages
<220> FEATURE:
<221> NAME/KEY: misc_feature
<222> LOCATION: (15)..(17)
<223> OTHER INFORMATION: LNA_modification

<400> SEQUENCE: 104
gtatcaaggt ctccctc                                                  17

<210> SEQ ID NO 105
<211> LENGTH: 17
<212> TYPE: DNA
<213> ORGANISM: Homo sapiens

<400> SEQUENCE: 105
ggtggttaca gcgatga                                                  17

<210> SEQ ID NO 106
<211> LENGTH: 17
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
```

```
<221> NAME/KEY: misc_feature
<222> LOCATION: (1)..(17)
<223> OTHER INFORMATION: phosphorothioate_linkages
<220> FEATURE:
<221> NAME/KEY: misc_feature
<222> LOCATION: (15)..(17)
<223> OTHER INFORMATION: LNA_modification

<400> SEQUENCE: 106
ggtggttaca gcgatga                                                17

<210> SEQ ID NO 107
<211> LENGTH: 17
<212> TYPE: DNA
<213> ORGANISM: Homo sapiens

<400> SEQUENCE: 107
ggactagatt gactcag                                                17

<210> SEQ ID NO 108
<211> LENGTH: 17
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(1)
<223> OTHER INFORMATION: LNA_modification
<220> FEATURE:
<221> NAME/KEY: misc_feature
<222> LOCATION: (1)..(17)
<223> OTHER INFORMATION: phosphorothioate_linkages
<220> FEATURE:
<221> NAME/KEY: misc_feature
<222> LOCATION: (3)..(3)
<223> OTHER INFORMATION: LNA_modification
<220> FEATURE:
<221> NAME/KEY: misc_feature
<222> LOCATION: (15)..(17)
<223> OTHER INFORMATION: LNA_modification

<400> SEQUENCE: 108
ggactagatt gactcag                                                17

<210> SEQ ID NO 109
<211> LENGTH: 17
<212> TYPE: DNA
<213> ORGANISM: Homo sapiens

<400> SEQUENCE: 109
acaacgaatg aggcttt                                                17

<210> SEQ ID NO 110
<211> LENGTH: 17
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(17)
<223> OTHER INFORMATION: phosphorothioate_linkages
```

```
<220> FEATURE:
<221> NAME/KEY: misc_feature
<222> LOCATION: (15)..(17)
<223> OTHER INFORMATION: LNA_modification

<400> SEQUENCE: 110
acaacgaatg aggcttt                                                 17

<210> SEQ ID NO 111
<211> LENGTH: 17
<212> TYPE: DNA
<213> ORGANISM: Homo sapiens

<400> SEQUENCE: 111
gactgagtag actatgt                                                 17

<210> SEQ ID NO 112
<211> LENGTH: 17
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(17)
<223> OTHER INFORMATION: phosphorothioate_linkages
<220> FEATURE:
<221> NAME/KEY: misc_feature
<222> LOCATION: (15)..(15)
<223> OTHER INFORMATION: LNA_modification
<220> FEATURE:
<221> NAME/KEY: misc_feature
<222> LOCATION: (17)..(17)
<223> OTHER INFORMATION: LNA_modification

<400> SEQUENCE: 112
gactgagtag actatgt                                                 17

<210> SEQ ID NO 113
<211> LENGTH: 17
<212> TYPE: DNA
<213> ORGANISM: Homo sapiens

<400> SEQUENCE: 113
gccatttacg atgaaac                                                 17

<210> SEQ ID NO 114
<211> LENGTH: 17
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(17)
<223> OTHER INFORMATION: phosphorothioate_linkages
<220> FEATURE:
<221> NAME/KEY: misc_feature
<222> LOCATION: (15)..(17)
```

<223> OTHER INFORMATION: LNA_modification

<400> SEQUENCE: 114
gccatttacg atgaaac                                                        17

<210> SEQ ID NO 115
<211> LENGTH: 3691
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)

<400> SEQUENCE: 115

| | | | | | |
|---|---|---|---|---|---|
| ggcgcaacgc | tgagcagctg | gcgcgtcccg | cgcggcccca | gttctgcgca | gcttcccgag | 60 |
| gctccgcacc | agccgcgctt | ctgtccgcct | gcagggcatt | ccagaaagat | gaggatattt | 120 |
| gctgtcttta | tattcatgac | ctactggcat | ttgctgaacg | catttactgt | cacggttccc | 180 |
| aaggacctat | atgtggtaga | gtatggtagc | aatatgacaa | ttgaatgcaa | attcccagta | 240 |
| gaaaaacaat | tagacctggc | tgcactaatt | gtctattggg | aaatggagga | taagaacatt | 300 |
| attcaatttg | tgcatggaga | ggaagacctg | aaggttcagc | atagtagcta | cagacagagg | 360 |
| gcccggctgt | tgaaggacca | gctctccctg | ggaaatgctg | cacttcagat | cacagatgtg | 420 |
| aaattgcagg | atgcagggnt | gtaccgctgc | atgatcagct | atggtggtgc | cgactacaag | 480 |
| cgaattactg | tgaaagtcaa | tgccccatac | aacaaaatca | ccaaagaat | tttggttgtg | 540 |
| gatccagtca | cctctgaaca | tgaactgaca | tgtcaggctg | agggctaccc | caaggccgaa | 600 |
| gtcatctgga | caagcagtga | ccatcaagtc | ctgagtggta | agaccaccac | caccaattcc | 660 |
| aagagagagg | agaagctttt | caatgtgacc | agcacactga | gatcaacac | aacaactaat | 720 |
| gagattttct | actgcacttt | taggagatta | gatcctgagg | aaaaccatac | agctgaattg | 780 |
| gtcatcccag | aactacctct | ggcacatcct | ccaaatgaaa | ggactcactt | ggtaattctg | 840 |
| ggagccatct | tattatgcct | tggtgtagca | ctgacattca | tcttccgttt | aagaaaaggg | 900 |
| agaatgatga | tgtgaaaaa | atgtggcatc | caagatacaa | actcaaagaa | gcaaagtgat | 960 |
| acacatttgg | aggagacgta | atccagcatt | ggaacttctg | atcttcaagc | agggattctc | 1020 |
| aacctgtggt | ttaggggttc | atcggggctg | agcgtgacaa | gaggaaggaa | tgggcccgtg | 1080 |
| ggatgcaggc | aatgtgggac | ttaaaaggcc | caagcactga | aaatggaacc | tggcgaaagc | 1140 |
| agaggaggag | aatgaagaaa | gatggagtca | acagggagc | ctggagggag | accttgatac | 1200 |
| tttcaaatgc | ctgaggggct | catcgacgcc | tgtgacaggg | agaaaggata | cttctgaaca | 1260 |
| aggagcctcc | aagcaaatca | tccattgctc | atcctaggaa | gacgggttga | gaatccctaa | 1320 |
| tttgagggtc | agttcctgca | gaagtgccct | ttgcctccac | tcaatgcctc | aatttgtttt | 1380 |
| ctgcatgact | gagagtctca | gtgttggaac | gggacagtat | ttatgtatga | gttttcctta | 1440 |
| tttattttga | gtctgtgagg | tcttcttgtc | atgtgagtgt | ggttgtgaat | gatttctttt | 1500 |
| gaagatatat | tgtagtagat | gttacaattt | tgtcgccaaa | ctaaacttgc | tgcttaatga | 1560 |
| tttgctcaca | tctagtaaaa | catggagtat | ttgtaaggtg | cttggtctcc | tctataacta | 1620 |
| caagtataca | ttggaagcat | aaagatcaaa | ccgttggttg | cataggatgt | cacctttatt | 1680 |
| taacccatta | atactctggt | tgacctaatc | ttattctcag | acctcaagtg | tctgtgcagt | 1740 |
| atctgttcca | tttaaatatc | agctttacaa | ttatgtggta | gcctacacac | ataatctcat | 1800 |
| ttcatcgctg | taaccaccct | gttgtgataa | ccactattat | tttacccatc | gtacagctga | 1860 |

```
ggaagcaaac agattaagta acttgcccaa accagtaaat agcagacctc agactgccac    1920
ccactgtcct tttataatac aatttacagc tatattttac tttaagcaat tcttttattc    1980
aaaaaccatt tattaagtgc ccttgcaata tcaatcgctg tgccaggcat tgaatctaca    2040
gatgtgagca agacaaagta cctgtcctca aggagctcat agtataatga ggagattaac    2100
aagaaaatgt attattacaa tttagtccag tgtcatagca taaggatgat gcgaggggaa    2160
aacccgagca gtgttgccaa gaggaggaaa taggccaatg tggtctggga cggttggata    2220
tacttaaaca tcttaataat cagagtaatt ttcatttaca agagaggtc ggtacttaaa     2280 ataaccctga aaataacac tggaattcct tttctagcat tatatttatt cctgatttgc     2340
ctttgccata taatctaatg cttgtttata tagtgtctgg tattgtttaa cagttctgtc    2400
ttttctattt aaatgccact aaattttaaa ttcatacctt tccatgattc aaaattcaaa    2460
agatcccatg ggagatggtt ggaaaatctc cacttcatcc tccaagccat tcaagtttcc    2520
tttccagaag caactgctac tgcctttcat tcatatgttc ttctaaagat agtctacatt    2580
tggaaatgta tgttaaaagc acgtattttt aaaattttt tcctaaatag taacacattg     2640
tatgtctgct gtgtactttg ctattttat ttattttagt gtttcttata tagcagatgg     2700
aatgaatttg aagttcccag ggctgaggat ccatgccttc tttgtttcta agttatcttt    2760
cccatagctt ttcattatct ttcatatgat ccagtatatg ttaaatatgt cctacatata    2820
catttagaca accaccattt gttaagtatt tgctctagga cagagtttgg atttgtttat    2880
gtttgctcaa aaggagaccc atgggctctc cagggtgcac tgagtcaatc tagtcctaaa    2940
aagcaatctt attattaact ctgtatgaca gaatcatgtc tggaactttt gttttctgct    3000
ttctgtcaag tataaacttc actttgatgc tgtacttgca aaatcacatt ttctttctgg    3060
aaattccggc agtgtaccctt gactgctagc taccctgtgc cagaaaagcc tcattcgttg    3120
tgcttgaacc cttgaatgcc accagctgtc atcactacac agccctccta agaggcttcc    3180
tggaggtttc gagattcaga tgccctggga gatcccagag tttcctttcc ctcttggcca    3240
tattctggtg tcaatgacaa ggagtaccctt ggctttgcca catgtcaagg ctgaagaaac   3300
agtgtctcca acagagctcc ttgtgttatc tgtttgtaca tgtgcatttg tacagtaatt    3360
ggtgtgacag tgttctttgt gtgaattaca ggcaagaatt gtggctgagc aaggcacata    3420
gtctactcag tctattccta agtcctaact cctccttgtg gtgttggatt tgtaaggcac    3480
tttatccctt ttgtctcatg tttcatcgta aatggcatag gcagagatga tacctaattc    3540
tgcatttgat tgtcactttt tgtacctgca ttaatttaat aaaatattct tatttatttt    3600
gttacttggt acaccagcat gtccattttc ttgtttattt tgtgtttaat aaaatgttca    3660
gtttaacatc ccagtggaga aagttaaaaa a                                   3691

<210> SEQ ID NO 116
<211> LENGTH: 3653
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)

<400> SEQUENCE: 116
gaaatcgtgg tccccaagcc tcatgccagg ctgcacttgc acgtcgcggg ccagtctcct      60
cgcctgcaga tagttcccaa aacatgagga tatttgctgg cattatattc acagcctgct     120
```

```
gtcacttgct acgggcgttt actatcacgg ctccaaagga cttgtacgtg gtggagtatg    180
gcagcaacgt cacgatggag tgcagattcc ctgtagaacg ggagctggac ctgcttgcgt    240
tagtggtgta ctgggaaaag gaagatgagc aagtgattca gtttgtggca ggagaggagg    300
accttaagcc tcagcacagc aacttcaggg ggagagcctc gctgccaaag gaccagcttt    360
tgaagggaaa tgctgccctt cagatcacag acgtcaagct gcaggacgca ggcgtttact    420
gctgcataat cagctacggt ggtgcggact acaagcgaat cacgctgaaa gtcaatgccc    480
cataccgcaa aatcaaccag agaatttccg tggatccagc cacttctgag catgaactaa    540
tatgtcaggc cgagggttat ccagaagctg aggtaatctg gacaaacagt gaccaccaac    600
ccgtgagtgg gaagagaagt gtcaccactt cccggacaga ggggatgctt ctcaatgtga    660
ccagcagtct gagggtcaac gccacagcga atgatgtttt ctactgtacg ttttggagat    720
cacagccagg gcaaaaccac acagcggagc tgatcatccc agaactgcct gcaacacatc    780
ctccacagaa caggactcac tgggtgcttc tgggatccat cctgttgttc ctcattgtag    840
tgtccacggt cctcctcttc ttgagaaaac aagtgagaat gctagatgtg gagaaatgtg    900
gcgttgaaga tacaagctca aaaaaccgaa atgatacaca attcgaggag acgtaagcag    960
tgttgaaccc tctgatcgtc gattggcagc ttgtggtctg tgaaagaaag ggcccatggg   1020
acatgagtcc aaagactcaa gatggaacct gagggagaga accaagaaag tgttgggaga   1080
ggagcctgga acaacggaca ttttttccag ggagacactg ctaagcaagt tgcccatcag   1140
tcgtcttggg aaatggattg agggttcctg gcttagcagc tggtccttgc acagtgacct   1200
tttcctctgc tcagtgccgg gatgagagat ggagtcatga gtgttgaaga ataagtgcct   1260
tctatttatt ttgagtctgt gtgttctcac tttgggcatg taattatgac tggtgaattc   1320
tgacgacatg atagatctta agatgtagtc accaaactca actgctgctt agcatcctcc   1380
gtaactactg atacaagcag ggaacacaga ggtcacctgc ttggtttgac aggctcttgc   1440
tgtctgactc aaataatctt tatttttcag tcctcaaggc tcttcgatag cagttgttct   1500
gtatcagcct tataggtgtc aggtatagca ctcaacatct catctcatta caatagcaac   1560
cctcatcacc atagcaacag ctaacctctg ttatcctcac ttcatagcca ggaagctgag   1620
cgactaagtc acttgcccac agagtatcag ctctcagatt tctgttcttc agccactgtc   1680
ctttcaggat agaatttgtc gttaagaaat taatttaaaa actgattatt gagtagcatt   1740
gtatatcaat cacaacatgc cttgtgcact gtgctggcct ctgagcataa agatgtacgc   1800
cggagtaccg gtcggacatg tttatgtgtg ttaaatactc agagaaatgt tcattaacaa   1860
ggagcttgca ttttagagac actggaaagt aactccagtt cattgtctag cattacattt   1920
acctcatttg ctatccttgc catacagtct cttgttctcc atgaagtgtc atgaatcttg   1980
ttgaatagtt cttttatttt ttaaatgttt ctatttaaat gatattgaca tctgaggcga   2040
tagctcagtt ggtaaaaccc tttcctcaca agtgtgaaac cctgagtctt atccctagaa   2100
cccacataaa aaacagttgc gtatgtttgt gcatgctttt gatcccagca ctagggaggc   2160
agaggcaggc agatcctgag ctctcattga ccacccagcc tagcctacat ggttagctcc   2220
aggcctacag gagctggcag agcctgaaaa acgatgccta gacacacaca cacacacaca   2280
cacacacaca cacacacaca caccatgt actcatagac ctaagtgcac cctcctacac   2340
atgcacacac atacaattca aacacaaatc aacagggaat tgtctcagaa tggtccccaa   2400
gacaaagaag aagaaaaaca ccaaaccagc tctattccct cagcctatcc tctctactcc   2460
ttcctagaag caactactat tgttttttgta tataaattta cccaacgaca gttaatatgt   2520
```

```
agaatatata ttaaagtgtc tgtcaatata tattatctct ttctttcttt cttcctttct    2580
ttctttcttt ctttctttct ttctttcttt ctttctttct ttcttccttc cttccttcct    2640
tccttccttc cttccttcct ttctttcttt ctttctttt  ttctgtctat ctgtacctaa    2700
atggttgctc actatgcatt ttctgtgctc ttcgcccttt ttatttaatg tatggatatt    2760
tatgctgctt ccagaatgga tctaaagctc tttgtttcta ggttttctcc cccatccttc    2820
taggcatctc tcacactgtc taggccagac accatgtctg ctgcctgaat ctgtagacac    2880
catttataaa gcacgtactc accgagtttg tatttggctt gttctgtgtc tgattaaagg    2940
gagaccatga gtccccaggg tacactgagt taccccagta ccaaggggga gccttgtttg    3000
tgtctccatg gcagaagcag gcctggagcc attttggttt cttccttgac ttctctcaaa    3060
cacagacgcc tcacttgctc attacaggtt ctcctttggg aatgtcagca ttgctccttg    3120
actgctggct gccctggaag gagcccatta gctctgtgtg agcccttgac agctactgcc    3180
tctccttacc acaggggcct ctaagatact gttacctaga ggtcttgagg atctgtgttc    3240
tctgggggga ggaaaggagg aggaacccag aactttctta cagttttcct tgttctgtca    3300
catgtcaaga ctgaaggaac aggctgggct acgtagtgag atcctgtctc aaaggaaaga    3360
cgagcatagc cgaacccccg gtggaacccc ctctgttacc tgttcacaca agcttattga    3420
tgagtctcat gttaatgtct tgtttgtatg aagtttaaga aaatatcggg ttgggcaaca    3480
cattctattt attcatttta tttgaaatct taatgccatc tcatggtgtt ggattggtgt    3540
ggcactttat tcttttgtgt tgtgtataac cataaatttt attttgcatc agattgtcaa    3600
tgtattgcat taatttaata aatatttta  tttattaaaa aaaaaaaaa  aaa           3653

<210> SEQ ID NO 117
<211> LENGTH: 17
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(15)
<223> OTHER INFORMATION: phosphorothioate_linkages
<220> FEATURE:
<221> NAME/KEY: misc_feature
<222> LOCATION: (13)..(15)
<223> OTHER INFORMATION: LNA_modification

<400> SEQUENCE: 117
atactccacc acgtaca                                                    17

<210> SEQ ID NO 118
<211> LENGTH: 17
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
```

```
<221> NAME/KEY: misc_feature
<222> LOCATION: (1)..(15)
<223> OTHER INFORMATION: phosphorothioate_linkages
<220> FEATURE:
<221> NAME/KEY: misc_feature
<222> LOCATION: (13)..(15)
<223> OTHER INFORMATION: LNA_modification

<400> SEQUENCE: 118
gccatactcc accacgt                                                17

<210> SEQ ID NO 119
<211> LENGTH: 17
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(15)
<223> OTHER INFORMATION: phosphorothioate_linkages
<220> FEATURE:
<221> NAME/KEY: misc_feature
<222> LOCATION: (13)..(15)
<223> OTHER INFORMATION: LNA_modification

<400> SEQUENCE: 119
gattcgcttg tagtccg                                                17

<210> SEQ ID NO 120
<211> LENGTH: 17
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(15)
<223> OTHER INFORMATION: phosphorothioate_linkages
<220> FEATURE:
<221> NAME/KEY: misc_feature
<222> LOCATION: (13)..(15)
<223> OTHER INFORMATION: LNA_modification

<400> SEQUENCE: 120
gcttacgtct cctcgaa                                                17

<210> SEQ ID NO 121
<211> LENGTH: 17
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
```

<222> LOCATION: (1)..(15)
<223> OTHER INFORMATION: phosphorothioate_linkages
<220> FEATURE:
<221> NAME/KEY: misc_feature
<222> LOCATION: (13)..(15)
<223> OTHER INFORMATION: LNA_modification

<400> SEQUENCE: 121
caacactgct tacgtct                                                17

<210> SEQ ID NO 122
<211> LENGTH: 17
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(16)
<223> OTHER INFORMATION: phosphorothioate_linkages
<220> FEATURE:
<221> NAME/KEY: misc_feature
<222> LOCATION: (14)..(16)
<223> OTHER INFORMATION: LNA_modification

<400> SEQUENCE: 122
gttcaacact gcttacg                                                17

<210> SEQ ID NO 123
<211> LENGTH: 17
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(16)
<223> OTHER INFORMATION: phosphorothioate_linkages
<220> FEATURE:
<221> NAME/KEY: misc_feature
<222> LOCATION: (14)..(16)
<223> OTHER INFORMATION: LNA_modification

<400> SEQUENCE: 123
ggttcaacac tgcttac                                                17

<210> SEQ ID NO 124
<211> LENGTH: 17
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(16)

```
<223> OTHER INFORMATION: phosphorothioate_linkages
<220> FEATURE:
<221> NAME/KEY: misc_feature
<222> LOCATION: (14)..(16)
<223> OTHER INFORMATION: LNA_modification

<400> SEQUENCE: 124
acaaactcgg tgagtac                                                        17

<210> SEQ ID NO 125
<211> LENGTH: 16
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(16)
<223> OTHER INFORMATION: phosphorothioate_linkages
<220> FEATURE:
<221> NAME/KEY: misc_feature
<222> LOCATION: (14)..(16)
<223> OTHER INFORMATION: LNA_modification

<400> SEQUENCE: 125
tactccacca cgtaca                                                         16

<210> SEQ ID NO 126
<211> LENGTH: 16
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(16)
<223> OTHER INFORMATION: phosphorothioate_linkages
<220> FEATURE:
<221> NAME/KEY: misc_feature
<222> LOCATION: (14)..(16)
<223> OTHER INFORMATION: LNA_modification

<400> SEQUENCE: 126
atactccacc acgtac                                                         16

<210> SEQ ID NO 127
<211> LENGTH: 16
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(16)
<223> OTHER INFORMATION: phosphorothioate_linkages
```

```
<220> FEATURE:
<221> NAME/KEY: misc_feature
<222> LOCATION: (14)..(16)
<223> OTHER INFORMATION: LNA_modification

<400> SEQUENCE: 127
catactccac cacgta                                                        16

<210> SEQ ID NO 128
<211> LENGTH: 16
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(16)
<223> OTHER INFORMATION: phosphorothioate_linkages
<220> FEATURE:
<221> NAME/KEY: misc_feature
<222> LOCATION: (14)..(16)
<223> OTHER INFORMATION: LNA_modification

<400> SEQUENCE: 128
ccatactcca ccacgt                                                        16

<210> SEQ ID NO 129
<211> LENGTH: 16
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(16)
<223> OTHER INFORMATION: phosphorothioate_linkages
<220> FEATURE:
<221> NAME/KEY: misc_feature
<222> LOCATION: (14)..(16)
<223> OTHER INFORMATION: LNA_modification

<400> SEQUENCE: 129
gccatactcc accacg                                                        16

<210> SEQ ID NO 130
<211> LENGTH: 16
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(16)
<223> OTHER INFORMATION: phosphorothioate_linkages
<220> FEATURE:
```

```
<221> NAME/KEY: misc_feature
<222> LOCATION: (14)..(16)
<223> OTHER INFORMATION: LNA_modification

<400> SEQUENCE: 130
ttcgcttgta gtccgc                                                    16

<210> SEQ ID NO 131
<211> LENGTH: 16
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(16)
<223> OTHER INFORMATION: phosphorothioate_linkages
<220> FEATURE:
<221> NAME/KEY: misc_feature
<222> LOCATION: (14)..(16)
<223> OTHER INFORMATION: LNA_modification

<400> SEQUENCE: 131
attcgcttgt agtccg                                                    16

<210> SEQ ID NO 132
<211> LENGTH: 16
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(2)
<223> OTHER INFORMATION: LNA_modification
<220> FEATURE:
<221> NAME/KEY: misc_feature
<222> LOCATION: (1)..(16)
<223> OTHER INFORMATION: phosphorothioate_linkages
<220> FEATURE:
<221> NAME/KEY: misc_feature
<222> LOCATION: (15)..(16)
<223> OTHER INFORMATION: LNA_modification

<400> SEQUENCE: 132
gattcgcttg tagtcc                                                    16

<210> SEQ ID NO 133
<211> LENGTH: 16
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(16)
<223> OTHER INFORMATION: phosphorothioate_linkages
<220> FEATURE:
<221> NAME/KEY: misc_feature
```

-continued

```
<222> LOCATION: (14)..(16)
<223> OTHER INFORMATION: LNA_modification

<400> SEQUENCE: 133
tgattcgctt gtagtc                                                   16

<210> SEQ ID NO 134
<211> LENGTH: 16
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(16)
<223> OTHER INFORMATION: phosphorothioate_linkages
<220> FEATURE:
<221> NAME/KEY: misc_feature
<222> LOCATION: (14)..(16)
<223> OTHER INFORMATION: LNA_modification

<400> SEQUENCE: 134
gttgattttg cggtat                                                   16

<210> SEQ ID NO 135
<211> LENGTH: 16
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(16)
<223> OTHER INFORMATION: phosphorothioate_linkages
<220> FEATURE:
<221> NAME/KEY: misc_feature
<222> LOCATION: (14)..(16)
<223> OTHER INFORMATION: LNA_modification

<400> SEQUENCE: 135
ggttgatttt gcggta                                                   16

<210> SEQ ID NO 136
<211> LENGTH: 16
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(16)
<223> OTHER INFORMATION: phosphorothioate_linkages
<220> FEATURE:
<221> NAME/KEY: misc_feature
<222> LOCATION: (14)..(16)
```

<223> OTHER INFORMATION: LNA_modification

<400> SEQUENCE: 136
tggttgattt tgcggt                                                                   16

<210> SEQ ID NO 137
<211> LENGTH: 16
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(17)
<223> OTHER INFORMATION: phosphorothioate_linkages
<220> FEATURE:
<221> NAME/KEY: misc_feature
<222> LOCATION: (15)..(17)
<223> OTHER INFORMATION: LNA_modification

<400> SEQUENCE: 137
tgtgtatcat ttcggt                                                                   16

<210> SEQ ID NO 138
<211> LENGTH: 16
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(17)
<223> OTHER INFORMATION: phosphorothioate_linkages
<220> FEATURE:
<221> NAME/KEY: misc_feature
<222> LOCATION: (15)..(17)
<223> OTHER INFORMATION: LNA_modification

<400> SEQUENCE: 138
cttacgtctc ctcgaa                                                                   16

<210> SEQ ID NO 139
<211> LENGTH: 16
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(17)
<223> OTHER INFORMATION: phosphorothioate_linkages
<220> FEATURE:
<221> NAME/KEY: misc_feature
<222> LOCATION: (15)..(17)
<223> OTHER INFORMATION: LNA_modification

```
<400> SEQUENCE: 139
caacactgct tacgtc                                                    16

<210> SEQ ID NO 140
<211> LENGTH: 15
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(17)
<223> OTHER INFORMATION: phosphorothioate_linkages
<220> FEATURE:
<221> NAME/KEY: misc_feature
<222> LOCATION: (16)..(17)
<223> OTHER INFORMATION: LNA_modification

<400> SEQUENCE: 140
ttcgcttgta gtccg                                                     15

<210> SEQ ID NO 141
<211> LENGTH: 15
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(1)
<223> OTHER INFORMATION: LNA_modification
<220> FEATURE:
<221> NAME/KEY: misc_feature
<222> LOCATION: (1)..(17)
<223> OTHER INFORMATION: phosphorothioate_linkages
<220> FEATURE:
<221> NAME/KEY: misc_feature
<222> LOCATION: (3)..(3)
<223> OTHER INFORMATION: LNA_modification
<220> FEATURE:
<221> NAME/KEY: misc_feature
<222> LOCATION: (15)..(17)
<223> OTHER INFORMATION: LNA_modification

<400> SEQUENCE: 141
gattcgcttg tagtc                                                     15

<210> SEQ ID NO 142
<211> LENGTH: 15
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(17)
<223> OTHER INFORMATION: phosphorothioate_linkages
<220> FEATURE:
```

```
<221> NAME/KEY: misc_feature
<222> LOCATION: (15)..(17)
<223> OTHER INFORMATION: LNA_modification

<400> SEQUENCE: 142
tgattcgctt gtagt                                                    15

<210> SEQ ID NO 143
<211> LENGTH: 15
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(17)
<223> OTHER INFORMATION: phosphorothioate_linkages
<220> FEATURE:
<221> NAME/KEY: misc_feature
<222> LOCATION: (15)..(17)
<223> OTHER INFORMATION: LNA_modification

<400> SEQUENCE: 143
ttacgtctcc tcgaa                                                    15

<210> SEQ ID NO 144
<211> LENGTH: 15
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(17)
<223> OTHER INFORMATION: phosphorothioate_linkages
<220> FEATURE:
<221> NAME/KEY: misc_feature
<222> LOCATION: (15)..(17)
<223> OTHER INFORMATION: LNA_modification

<400> SEQUENCE: 144
cttacgtctc ctcga                                                    15

<210> SEQ ID NO 145
<211> LENGTH: 17
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(18)
<223> OTHER INFORMATION: phosphorothioate_linkages
<220> FEATURE:
<221> NAME/KEY: misc_feature
```

```
<222> LOCATION: (16)..(18)
<223> OTHER INFORMATION: LNA_modification

<400> SEQUENCE: 145
tctatcgtga tgtttct                                                    17

<210> SEQ ID NO 146
<211> LENGTH: 17
<212> TYPE: DNA
<213> ORGANISM: Artificial Sequence
<220> FEATURE:
<223> OTHER INFORMATION: antisense_sequence_5'-3'_partially_with_
      phosphorothioate_linkages_ [*]_and_LNA_modifications_[+] (see
      Misc_Features)
<220> FEATURE:
<221> NAME/KEY: misc_feature
<222> LOCATION: (1)..(3)
<223> OTHER INFORMATION: LNA_modification
<220> FEATURE:
<221> NAME/KEY: misc_feature
<222> LOCATION: (1)..(17)
<223> OTHER INFORMATION: phosphorothioate_linkages
<220> FEATURE:
<221> NAME/KEY: misc_feature
<222> LOCATION: (15)..(17)
<223> OTHER INFORMATION: LNA_modification

<400> SEQUENCE: 146
tctatcgtga tgtttct                                                    17
```